US012195741B2

(12) United States Patent
Gao et al.

(10) Patent No.: US 12,195,741 B2
(45) Date of Patent: Jan. 14, 2025

(54) CREATION OF HERBICIDE RESISTANT GENE AND USE THEREOF

(71) Applicants: INSTITUTE OF GENETICS AND DEVELOPMENTAL BIOLOGY, CHINESE ACADEMY OF SCIENCES, Beijing (CN); CHINA AGRICULTURAL UNIVERSITY, Beijing (CN)

(72) Inventors: Caixia Gao, Beijing (CN); Linjian Jiang, Beijing (CN)

(73) Assignees: INSTITUTE OF GENETICS AND DEVELOPMENTAL BIOLOGY, CHINESE ACADEMY OF SCIENCES, Beijing (CN); CHINA AGRICULTURAL UNIVERSITY, Beijing (CN)

(*) Notice: Subject to any disclaimer, the term of this patent is extended or adjusted under 35 U.S.C. 154(b) by 0 days.

(21) Appl. No.: 17/733,123

(22) Filed: Apr. 29, 2022

(65) Prior Publication Data

US 2022/0267788 A1 Aug. 25, 2022

Related U.S. Application Data

(62) Division of application No. 16/612,158, filed as application No. PCT/CN2018/086501 on May 11, 2018, now Pat. No. 11,345,924.

(30) Foreign Application Priority Data

May 11, 2017 (CN) .......................... 201710329242.9

(51) Int. Cl.
 C12N 15/82 (2006.01)
 C12N 9/22 (2006.01)
 C12N 15/113 (2010.01)

(52) U.S. Cl.
 CPC ........... *C12N 15/8274* (2013.01); *C12N 9/22* (2013.01); *C12N 15/113* (2013.01); *C12Y 604/01002* (2013.01)

(58) Field of Classification Search
 None
 See application file for complete search history.

(56) References Cited

U.S. PATENT DOCUMENTS

| 6,919,619 B2 | 7/2005 | Sylvester et al. | |
| 2012/0060243 A1* | 3/2012 | Beetham ............ | C12N 15/8278 800/300 |
| 2014/0304853 A1* | 10/2014 | Ainley ................ | C12N 15/8274 800/300 |
| 2016/0208271 A1 | 7/2016 | Cigan et al. | |
| 2016/0208277 A1* | 7/2016 | Ruiter ................. | C12N 15/8274 |
| 2017/0073670 A1 | 3/2017 | Nishida et al. | |
| 2017/0121693 A1 | 5/2017 | Liu et al. | |
| 2018/0216128 A1* | 8/2018 | Bernacchi ............. | A01N 43/50 |
| 2019/0292553 A1 | 9/2019 | Gao et al. | |

FOREIGN PATENT DOCUMENTS

| CN | 103796507 A | 5/2014 | |
| CN | 1058295536 A | 8/2016 | |
| CN | 106467909 A | 3/2017 | |
| JP | 2016-182120 A | 10/2016 | |
| WO | WO-2007149069 A2 * | 12/2007 | ......... C12N 15/8274 |
| WO | 2011/028832 A2 | 3/2011 | |
| WO | WO-2013074524 A1 * | 5/2013 | ......... C12N 15/8274 |
| WO | 2014/186686 | 11/2014 | |
| WO | 2015/159068 A1 | 10/2015 | |
| WO | 2017/070029 A1 | 4/2017 | |
| WO | WO-2017139304 A1 * | 8/2017 | ............... A01H 5/10 |

OTHER PUBLICATIONS

Kawai et al 2007 (J. Pestic. Sci. 33:2 p. 128-137) (Year: 2007).*
Jiang, S.C. et al., "Application of CRISPR/Cas9 gene editing technique in cancer drug resistance: research advances", Journal of International Pharmaceutical Reseach, vol. 44, No. 4, Apr. 30, 2017, pp. 299-305. with English Abstract.
International Search Report and Written Opinion mailed on Aug. 7, 2018, issued in corresponding Application No. PCT/CN2018/086501.
Wang et al., "Simultaneous editing of three homoeoalleles in hexaploid bread wheat confers heritable resistance to powdery mildew", Nature Biotechnology, 2014, vol. 32, No. 9, pp. 947-951.
Shan et al., "Targeted genome modification of crop plants using a CRISPR-Cas system", Nature Biotechnology, 2013, vol. 31, No. 8, pp. 686-688.
Liang et al., "Targeted mutagenesis in *Zea mays* using TALENs and the CRISPR/Cas system", Journal of Genetics and Genomics, 2014, vol. 41, pp. 63-68.
Shan et al., "Genome editing in rice and wheat using the CRISPR/Cas system", Nature Protocols, 2014, vol. 9, No. 10, pp. 2395-2410.
Zong et al., "Precise base editing in rice, wheat and maize with a Cas9- cytidine deaminase fusion", Nature Biotechnology, 2017, vol. 35, No. 5, pp. 438-440, doi: 10.1038/nbt.3811.
Zhang et al., "Biolistic genetic transformation of a wide range of Chinese elite wheat (*Triticum aestivum* L.) varieties", Journal of Genetics and Genomics, 2015, vol. 42, pp. 39-42.

(Continued)

*Primary Examiner* — Matthew R Keogh

(74) *Attorney, Agent, or Firm* — Troutman Pepper Hamilton Sanders LLP

(57) ABSTRACT

The present invention belongs to the field of plant genetic engineering. Specifically, the invention relates to a method for creating novel herbicide resistant plants by base editing techniques and a method for screening endogenous gene mutation sites capable of conferring herbicide resistance in plants. The invention also relates to the use of the identified endogenous gene mutantation sites in crop breeding.

16 Claims, 3 Drawing Sheets

Specification includes a Sequence Listing.

(56) References Cited

OTHER PUBLICATIONS

Svitashev et al., "Genome editing in maize directed by CRISPR-Cas9 ribonucleoprotein complexes", Nature Communications, 2016, vol. 7, p. 13274.

Ungerer et al., Cpf1 is a Versatile Tool for CRISPR Genome Editing Across Diverse Species of Cyanobacteria, Scientific Reports, 2016, vol. 6, No. 1, pp. 1-9.

Sauer et al., "Oligonucleotide—Mediated Genome Editing Provides Precision and Function to Engineered Nucleases and Antibiotics in Plants", Plant Physiology, 2016, vol. 170, No. 4, pp. 1917-1928.

Sun et al., "Engineering herbicide-resistant plants through CRISPR/Cas9-mediated homologous recombination in acetolactate synthase", Molecular Plant, 2016, vol. 9, pp. 628-631.

Liu et al. 2008, (GenBank: EU977181.1).

Shimatani et al., "Targeted base editing in rice and tomato using a CRISPR-Cas9 cytidine deaminase fusion", Nature Biotechnology, 2017, vol. 35, No. 5, pp. 441-443.

Zhang et al., "Generation of herbicide tolerance traits and a new selectable marker in wheat using base editing", Nature Plants, 2019, vol. 5, pp. 480-485.

Zhang et al., "Generating broad-spectrum tolerance to ALS-inhibiting herbicides in rice by base editing", Science China Life Sci, 2020, vol. 63, 10 pages.

Li et al., "Targeted, random mutagenesis of plant genes with dual cytosine and adenine base editors", Nature Biotechnology, 2020, vol. 38, pp. 875-882.

Li et al., "Expanded base editing in rice and wheat using a Cas9-adenosine deaminase fusion", Genome Biology, 2018, vol. 19, 9 pages.

Office Action issued in CN Application No. 201810447924.4 dated Feb. 23, 2021.

Komor et al., "Programmable editing of a target base in genomic DNA without double-stranded DNA cleavage", Nature, 2016, vol. 533, Issue 7603, pp. 420-424.

Chen et al., "CRISPR/Cas9-Mediated Base-Editing System Efficiently Generates Gain-of-Function Mutations in Arabidopsis", Sci China Life Sci, 2017, vol. 47, No. 11, pp. 1196-1199. (with English translation).

Xueling et al., "Herbicide Resistance Based on Altered Target Sites", Chemistry, 2006, No. 1, pp. 9-15. (with English Abstract and translation).

Pollegioni et al., "Molecular basis of glyphosate resistance: Different approaches through protein engineering", FEBS Journal, 2011, vol. 278, No. 16, pp. 2753-2766.

\* cited by examiner

SEQUENCE LISTING

<160> NUMBER OF SEQ ID NOS: 93

<210> SEQ ID NO 1
<211> LENGTH: 2320
<212> TYPE: PRT
<213> ORGANISM: Alopecurus myosuroides

<400> SEQUENCE: 1

Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly

```
            130                 135                 140
Met Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
            195                 200                 205

Leu Ile Val Glu Ile Ala Glu Arg Thr Gly Val Ser Ala Val Trp Pro
210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
            275                 280                 285

Cys Leu Asp Ser Ile Pro Glu Glu Met Tyr Arg Lys Ala Cys Val Thr
290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
            355                 360                 365

His Leu Glu Val Gln Leu Leu Cys Asp Glu Tyr Gly Asn Val Ala Ala
370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
            435                 440                 445

Leu Glu Leu Asn Pro Arg Leu Gln Val Glu His Pro Val Thr Glu Ser
450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
            515                 520                 525

Val Ala Val Arg Ile Thr Ser Glu Asn Pro Asp Asp Gly Phe Lys Pro
530                 535                 540

Thr Gly Gly Lys Val Lys Glu Ile Ser Phe Lys Ser Lys Pro Asn Val
545                 550                 555                 560
```

```
Trp Gly Tyr Phe Ser Val Lys Ser Gly Gly Ile His Glu Phe Ala
            565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
            595                 600                 605

Glu Ile His Thr Asn Val Asp Tyr Thr Val Asp Leu Leu Asn Ala Pro
            610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
            645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
            675                 680                 685

Ser Leu Val His Ser Thr Ile Ser Leu Asn Ile Glu Glu Ser Lys Tyr
            690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
            725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
            755                 760                 765

Gln Asn Asp His Asp Pro Ser Arg Leu Leu Ala Glu Thr Pro Cys Lys
            770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
            805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
            835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
            885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
            915                 920                 925

Arg Leu Lys Ser Glu Leu Glu Gly Lys Tyr Asn Glu Tyr Lys Leu Asn
            930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Lys Glu Met Val Thr
            965                 970                 975
```

Ile Glu Arg Leu Val Asp Pro Leu Met Ser Leu Leu Lys Ser Tyr Glu
            980                 985                 990

Gly Gly Arg Glu Ser His Ala His Phe Ile Val Lys Ser Leu Phe Glu
        995                 1000                1005

Glu Tyr Leu Ser Val Glu Glu Leu Phe Ser Asp Gly Ile Gln Ser
    1010                1015                1020

Asp Val Ile Glu Arg Leu Arg Leu Gln Tyr Ser Lys Asp Leu Gln
    1025                1030                1035

Lys Val Val Asp Ile Val Leu Ser His Gln Gly Val Arg Asn Lys
    1040                1045                1050

Thr Lys Leu Ile Leu Ala Leu Met Glu Lys Leu Val Tyr Pro Asn
    1055                1060                1065

Pro Ala Ala Tyr Arg Asp Gln Leu Ile Arg Phe Ser Ser Leu Asn
    1070                1075                1080

His Lys Arg Tyr Tyr Lys Leu Ala Leu Lys Ala Ser Glu Leu Leu
    1085                1090                1095

Glu Gln Thr Lys Leu Ser Glu Leu Arg Thr Ser Ile Ala Arg Asn
    1100                1105                1110

Leu Ser Ala Leu Asp Met Phe Thr Glu Glu Lys Ala Asp Phe Ser
    1115                1120                1125

Leu Gln Asp Arg Lys Leu Ala Ile Asn Glu Ser Met Gly Asp Leu
    1130                1135                1140

Val Thr Ala Pro Leu Pro Val Glu Asp Ala Leu Val Ser Leu Phe
    1145                1150                1155

Asp Cys Thr Asp Gln Thr Leu Gln Gln Arg Val Ile Gln Thr Tyr
    1160                1165                1170

Ile Ser Arg Leu Tyr Gln Pro Gln Leu Val Lys Asp Ser Ile Gln
    1175                1180                1185

Leu Lys Tyr Gln Asp Ser Gly Val Ile Ala Leu Trp Glu Phe Thr
    1190                1195                1200

Glu Gly Asn His Glu Lys Arg Leu Gly Ala Met Val Ile Leu Lys
    1205                1210                1215

Ser Leu Glu Ser Val Ser Thr Ala Ile Gly Ala Ala Leu Lys Asp
    1220                1225                1230

Ala Ser His Tyr Ala Ser Ser Ala Gly Asn Thr Val His Ile Ala
    1235                1240                1245

Leu Leu Asp Ala Asp Thr Gln Leu Asn Thr Thr Glu Asp Ser Gly
    1250                1255                1260

Asp Asn Asp Gln Ala Gln Asp Lys Met Asp Lys Leu Ser Phe Val
    1265                1270                1275

Leu Lys Gln Asp Val Val Met Ala Asp Leu Arg Ala Ala Asp Val
    1280                1285                1290

Lys Val Val Ser Cys Ile Val Gln Arg Asp Gly Ala Ile Met Pro
    1295                1300                1305

Met Arg Arg Thr Phe Leu Leu Ser Glu Glu Lys Leu Cys Tyr Glu
    1310                1315                1320

Glu Glu Pro Ile Leu Arg His Val Glu Pro Leu Ser Ala Leu
    1325                1330                1335

Leu Glu Leu Asp Lys Leu Lys Val Lys Gly Tyr Asn Glu Met Lys
    1340                1345                1350

Tyr Thr Pro Ser Arg Asp Arg Gln Trp His Ile Tyr Thr Leu Arg
    1355                1360                1365

Asn Thr Glu Asn Pro Lys Met Leu His Arg Val Phe Phe Arg Thr

-continued

```
            1370              1375              1380
Leu Val Arg Gln Pro Ser Ala Gly Asn Arg Phe Thr Ser Asp His
    1385              1390              1395
Ile Thr Asp Val Glu Val Gly His Ala Glu Pro Leu Ser Phe
    1400              1405              1410
Thr Ser Ser Ser Ile Leu Lys Ser Leu Lys Ile Ala Lys Glu Glu
    1415              1420              1425
Leu Glu Leu His Ala Ile Arg Thr Gly His Ser His Met Tyr Leu
    1430              1435              1440
Cys Ile Leu Lys Glu Gln Lys Leu Leu Asp Leu Val Pro Val Ser
    1445              1450              1455
Gly Asn Thr Val Val Asp Val Gly Gln Asp Glu Ala Thr Ala Cys
    1460              1465              1470
Ser Leu Leu Lys Glu Met Ala Leu Lys Ile His Glu Leu Val Gly
    1475              1480              1485
Ala Arg Met His His Leu Ser Val Cys Gln Trp Glu Val Lys Leu
    1490              1495              1500
Lys Leu Val Ser Asp Gly Pro Ala Ser Gly Ser Trp Arg Val Val
    1505              1510              1515
Thr Thr Asn Val Thr Gly His Thr Cys Thr Val Asp Ile Tyr Arg
    1520              1525              1530
Glu Val Glu Asp Thr Glu Ser Gln Lys Leu Val Tyr His Ser Thr
    1535              1540              1545
Ala Leu Ser Ser Gly Pro Leu His Gly Val Ala Leu Asn Thr Ser
    1550              1555              1560
Tyr Gln Pro Leu Ser Val Ile Asp Leu Lys Arg Cys Ser Ala Arg
    1565              1570              1575
Asn Asn Lys Thr Thr Tyr Cys Tyr Asp Phe Pro Leu Thr Phe Glu
    1580              1585              1590
Ala Ala Val Gln Lys Ser Trp Ser Asn Ile Ser Ser Glu Asn Asn
    1595              1600              1605
Gln Cys Tyr Val Lys Ala Thr Glu Leu Val Phe Ala Glu Lys Asn
    1610              1615              1620
Gly Ser Trp Gly Thr Pro Ile Ile Pro Met Gln Arg Ala Ala Gly
    1625              1630              1635
Leu Asn Asp Ile Gly Met Val Ala Trp Ile Leu Asp Met Ser Thr
    1640              1645              1650
Pro Glu Phe Pro Ser Gly Arg Gln Ile Ile Val Ile Ala Asn Asp
    1655              1660              1665
Ile Thr Phe Arg Ala Gly Ser Phe Gly Pro Arg Glu Asp Ala Phe
    1670              1675              1680
Phe Glu Ala Val Thr Asn Leu Ala Cys Glu Lys Lys Leu Pro Leu
    1685              1690              1695
Ile Tyr Leu Ala Ala Asn Ser Gly Ala Arg Ile Gly Ile Ala Asp
    1700              1705              1710
Glu Val Lys Ser Cys Phe Arg Val Gly Trp Thr Asp Asp Ser Ser
    1715              1720              1725
Pro Glu Arg Gly Phe Arg Tyr Ile Tyr Met Thr Asp Glu Asp His
    1730              1735              1740
Asp Arg Ile Gly Ser Ser Val Ile Ala His Lys Met Gln Leu Asp
    1745              1750              1755
Ser Gly Glu Ile Arg Trp Val Ile Asp Ser Val Val Gly Lys Glu
    1760              1765              1770
```

```
Asp Gly Leu Gly Val Glu Asn Ile His Gly Ser Ala Ala Ile Ala
    1775                1780                1785

Ser Ala Tyr Ser Arg Ala Tyr Glu Glu Thr Phe Thr Leu Thr Phe
    1790                1795                1800

Val Thr Gly Arg Thr Val Gly Ile Gly Ala Tyr Leu Ala Arg Leu
    1805                1810                1815

Gly Ile Arg Cys Ile Gln Arg Ile Asp Gln Pro Ile Ile Leu Thr
    1820                1825                1830

Gly Phe Ser Ala Leu Asn Lys Leu Leu Gly Arg Glu Val Tyr Ser
    1835                1840                1845

Ser His Met Gln Leu Gly Gly Pro Lys Ile Met Ala Thr Asn Gly
    1850                1855                1860

Val Val His Leu Thr Val Pro Asp Asp Leu Glu Gly Val Ser Asn
    1865                1870                1875

Ile Leu Arg Trp Leu Ser Tyr Val Pro Ala Asn Ile Gly Gly Pro
    1880                1885                1890

Leu Pro Ile Thr Lys Ser Leu Asp Pro Ile Asp Arg Pro Val Ala
    1895                1900                1905

Tyr Ile Pro Glu Asn Thr Cys Asp Pro Arg Ala Ala Ile Ser Gly
    1910                1915                1920

Ile Asp Asp Ser Gln Gly Lys Trp Leu Gly Gly Met Phe Asp Lys
    1925                1930                1935

Asp Ser Phe Val Glu Thr Phe Glu Gly Trp Ala Lys Thr Val Val
    1940                1945                1950

Thr Gly Arg Ala Lys Leu Gly Gly Ile Pro Val Gly Val Ile Ala
    1955                1960                1965

Val Glu Thr Gln Thr Met Met Gln Leu Val Pro Ala Asp Pro Gly
    1970                1975                1980

Gln Pro Asp Ser His Glu Arg Ser Val Pro Arg Ala Gly Gln Val
    1985                1990                1995

Trp Phe Pro Asp Ser Ala Thr Lys Thr Ala Gln Ala Met Leu Asp
    2000                2005                2010

Phe Asn Arg Glu Gly Leu Pro Leu Phe Ile Leu Ala Asn Trp Arg
    2015                2020                2025

Gly Phe Ser Gly Gly Gln Arg Asp Leu Phe Glu Gly Ile Leu Gln
    2030                2035                2040

Ala Gly Ser Thr Ile Val Glu Asn Leu Arg Thr Tyr Asn Gln Pro
    2045                2050                2055

Ala Phe Val Tyr Ile Pro Lys Ala Ala Glu Leu Arg Gly Gly Ala
    2060                2065                2070

Trp Val Val Ile Asp Ser Lys Ile Asn Pro Asp Arg Ile Glu Cys
    2075                2080                2085

Tyr Ala Glu Arg Thr Ala Lys Gly Asn Val Leu Glu Pro Gln Gly
    2090                2095                2100

Leu Ile Glu Ile Lys Phe Arg Ser Glu Glu Leu Lys Glu Cys Met
    2105                2110                2115

Gly Arg Leu Asp Pro Glu Leu Ile Asp Leu Lys Ala Arg Leu Gln
    2120                2125                2130

Gly Ala Asn Gly Ser Leu Ser Asp Gly Glu Ser Leu Gln Lys Ser
    2135                2140                2145

Ile Glu Ala Arg Lys Lys Gln Leu Leu Pro Leu Tyr Thr Gln Ile
    2150                2155                2160
```

```
Ala Val Arg Phe Ala Glu Leu His Asp Thr Ser Leu Arg Met Ala
2165                2170                2175

Ala Lys Gly Val Ile Arg Lys Val Val Asp Trp Glu Asp Ser Arg
2180                2185                2190

Ser Phe Phe Tyr Lys Arg Leu Arg Arg Arg Leu Ser Glu Asp Val
2195                2200                2205

Leu Ala Lys Glu Ile Arg Gly Val Ile Gly Glu Lys Phe Pro His
2210                2215                2220

Lys Ser Ala Ile Glu Leu Ile Lys Lys Trp Tyr Leu Ala Ser Glu
2225                2230                2235

Ala Ala Ala Ala Gly Ser Thr Asp Trp Asp Asp Asp Asp Ala Phe
2240                2245                2250

Val Ala Trp Arg Glu Asn Pro Glu Asn Tyr Lys Glu Tyr Ile Lys
2255                2260                2265

Glu Leu Arg Ala Gln Arg Val Ser Arg Leu Leu Ser Asp Val Ala
2270                2275                2280

Gly Ser Ser Ser Asp Leu Gln Ala Leu Pro Gln Gly Leu Ser Met
2285                2290                2295

Leu Leu Asp Lys Met Asp Pro Ser Lys Arg Ala Gln Phe Ile Glu
2300                2305                2310

Glu Val Met Lys Val Leu Lys
2315                2320

<210> SEQ ID NO 2
<211> LENGTH: 670
<212> TYPE: PRT
<213> ORGANISM: Arabidopsis thaliana

<400> SEQUENCE: 2

Met Ala Ala Ala Thr Thr Thr Thr Thr Ser Ser Ser Ile Ser Phe
1                   5                   10                  15

Ser Thr Lys Pro Ser Pro Ser Ser Lys Ser Pro Leu Pro Ile Ser
                20                  25                  30

Arg Phe Ser Leu Pro Phe Ser Leu Asn Pro Asn Lys Ser Ser Ser
            35                  40                  45

Ser Arg Arg Arg Gly Ile Lys Ser Ser Pro Ser Ser Ile Ser Ala
    50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
        115                 120                 125

Ala Leu Thr Arg Ser Ser Ser Ile Arg Asn Val Leu Pro Arg His Glu
    130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Pro Arg Arg Met Ile Gly Thr Asp Ala Phe Gln Glu
        195                 200                 205
```

```
Thr Pro Ile Val Glu Val Thr Arg Ser Ile Thr Lys His Asn Tyr Leu
    210                 215                 220
Val Met Asp Val Glu Asp Ile Pro Arg Ile Ile Glu Glu Ala Phe Phe
225                 230                 235                 240
Leu Ala Thr Ser Gly Arg Pro Gly Pro Val Leu Val Asp Val Pro Lys
                245                 250                 255
Asp Ile Gln Gln Gln Leu Ala Ile Pro Asn Trp Glu Gln Ala Met Arg
                260                 265                 270
Leu Pro Gly Tyr Met Ser Arg Met Pro Lys Pro Pro Glu Asp Ser His
            275                 280                 285
Leu Glu Gln Ile Val Arg Leu Ile Ser Glu Ser Lys Lys Pro Val Leu
290                 295                 300
Tyr Val Gly Gly Gly Cys Leu Asn Ser Ser Asp Glu Leu Gly Arg Phe
305                 310                 315                 320
Val Glu Leu Thr Gly Ile Pro Val Ala Ser Thr Leu Met Gly Leu Gly
                325                 330                 335
Ser Tyr Pro Cys Asp Asp Glu Leu Ser Leu His Met Leu Gly Met His
                340                 345                 350
Gly Thr Val Tyr Ala Asn Tyr Ala Val Glu His Ser Asp Leu Leu Leu
            355                 360                 365
Ala Phe Gly Val Arg Phe Asp Asp Arg Val Thr Gly Lys Leu Glu Ala
    370                 375                 380
Phe Ala Ser Arg Ala Lys Ile Val His Ile Asp Ile Asp Ser Ala Glu
385                 390                 395                 400
Ile Gly Lys Asn Lys Thr Pro His Val Ser Val Cys Gly Asp Val Lys
                405                 410                 415
Leu Ala Leu Gln Gly Met Asn Lys Val Leu Glu Asn Arg Ala Glu Glu
                420                 425                 430
Leu Lys Leu Asp Phe Gly Val Trp Arg Asn Glu Leu Asn Val Gln Lys
            435                 440                 445
Gln Lys Phe Pro Leu Ser Phe Lys Thr Phe Gly Glu Ala Ile Pro Pro
    450                 455                 460
Gln Tyr Ala Ile Lys Val Leu Asp Glu Leu Thr Asp Gly Lys Ala Ile
465                 470                 475                 480
Ile Ser Thr Gly Val Gly Gln His Gln Met Trp Ala Ala Gln Phe Tyr
                485                 490                 495
Asn Tyr Lys Lys Pro Arg Gln Trp Leu Ser Ser Gly Gly Leu Gly Ala
                500                 505                 510
Met Gly Phe Gly Leu Pro Ala Ala Ile Gly Ala Ser Val Ala Asn Pro
            515                 520                 525
Asp Ala Ile Val Val Asp Ile Asp Gly Asp Gly Ser Phe Ile Met Asn
    530                 535                 540
Val Gln Glu Leu Ala Thr Ile Arg Val Glu Asn Leu Pro Val Lys Val
545                 550                 555                 560
Leu Leu Leu Asn Asn Gln His Leu Gly Met Val Met Gln Trp Glu Asp
                565                 570                 575
Arg Phe Tyr Lys Ala Asn Arg Ala His Thr Phe Leu Gly Asp Pro Ala
            580                 585                 590
Gln Glu Asp Glu Ile Phe Pro Asn Met Leu Leu Phe Ala Ala Ala Cys
    595                 600                 605
Gly Ile Pro Ala Ala Arg Val Thr Lys Lys Ala Asp Leu Arg Glu Ala
610                 615                 620
```

-continued

```
Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
                645                 650                 655

Phe Asn Asp Val Ile Thr Glu Gly Asp Gly Arg Ile Lys Tyr
            660                 665                 670

<210> SEQ ID NO 3
<211> LENGTH: 446
<212> TYPE: PRT
<213> ORGANISM: Oryza sativa

<400> SEQUENCE: 3

Met Pro Pro Thr Pro Thr Pro Thr Ala Thr Thr Gly Ala Val Ser Ala
1               5                   10                  15

Ala Ala Ala Ala Gly Glu Asn Ala Gly Phe Arg Leu Val Gly His Arg
                20                  25                  30

Arg Phe Val Arg Ala Asn Pro Arg Ser Asp Arg Phe Gln Ala Leu Ala
            35                  40                  45

Phe His His Val Glu Leu Trp Cys Ala Asp Ala Ser Ala Ala Gly
        50                  55                  60

Arg Phe Ala Phe Ala Leu Gly Ala Pro Leu Ala Ala Arg Ser Asp Leu
65                  70                  75                  80

Ser Thr Gly Asn Ser Ala His Ser Leu Leu Leu Arg Ser Ala Ser
                85                  90                  95

Val Ala Phe Leu Phe Thr Ala Pro Tyr Gly Gly Asp His Gly Val Gly
                100                 105                 110

Ala Asp Ala Ala Thr Thr Ala Ser Ile Pro Ser Phe Ser Pro Gly Ala
            115                 120                 125

Ala Arg Arg Phe Ala Ala Asp His Gly Leu Ala Val His Ala Val Ala
130                 135                 140

Leu Arg Val Ala Asp Ala Ala Asp Ala Phe Arg Ala Ser Val Ala Ala
145                 150                 155                 160

Gly Ala Arg Pro Ala Phe Gln Pro Ala Asp Leu Gly Gly Phe Gly
                165                 170                 175

Leu Ala Glu Val Glu Leu Tyr Gly Asp Val Val Leu Arg Phe Val Ser
            180                 185                 190

His Pro Asp Gly Ala Asp Ala Pro Phe Leu Pro Gly Phe Glu Gly Val
        195                 200                 205

Ser Asn Pro Gly Ala Val Asp Tyr Gly Leu Arg Arg Phe Asp His Val
    210                 215                 220

Val Gly Asn Val Pro Glu Leu Ala Pro Val Ala Ala Tyr Ile Ser Gly
225                 230                 235                 240

Phe Thr Gly Phe His Glu Phe Ala Glu Phe Thr Ala Glu Asp Val Gly
                245                 250                 255

Thr Ala Glu Ser Gly Leu Asn Ser Val Val Leu Ala Asn Asn Ala Glu
            260                 265                 270

Thr Val Leu Leu Pro Leu Asn Glu Pro Val His Gly Thr Lys Arg Arg
        275                 280                 285

Ser Gln Ile Gln Thr Tyr Leu Asp His Gly Pro Gly Val Gln
    290                 295                 300

His Ile Ala Leu Ala Ser Asp Asp Val Leu Gly Thr Leu Arg Glu Met
305                 310                 315                 320

Arg Ala Arg Ser Ala Met Gly Gly Phe Glu Phe Leu Ala Pro Pro Pro
                325                 330                 335
```

```
Pro Asn Tyr Tyr Asp Gly Val Arg Arg Arg Ala Gly Asp Val Leu Ser
                340                 345                 350

Glu Glu Gln Ile Asn Glu Cys Gln Glu Leu Gly Val Leu Val Asp Arg
            355                 360                 365

Asp Asp Gln Gly Val Leu Leu Gln Ile Phe Thr Lys Pro Val Gly Asp
        370                 375                 380

Arg Pro Thr Phe Phe Leu Glu Met Ile Gln Arg Ile Gly Cys Met Glu
385                 390                 395                 400

Lys Asp Glu Ser Gly Gln Glu Tyr Gln Lys Gly Gly Cys Gly Gly Phe
                405                 410                 415

Gly Lys Gly Asn Phe Ser Glu Leu Phe Lys Ser Ile Glu Glu Tyr Glu
            420                 425                 430

Lys Ser Leu Glu Ala Lys Gln Ala Pro Thr Val Gln Gly Ser
        435                 440                 445

<210> SEQ ID NO 4
<211> LENGTH: 510
<212> TYPE: PRT
<213> ORGANISM: Triticum aestivum

<400> SEQUENCE: 4

Met Ala Met Ala Ala Ala Ala Thr Val Ala Ala Ser Ala Ser Ser Ser
1               5                   10                  15

Ala Val Ser Leu Asp Arg Ala Ala Pro Ala His Pro Arg Arg Leu Arg
                20                  25                  30

Met Pro Ala Ala Arg Ala Ala His Arg Gly Ala Val Arg Leu Trp Gly
            35                  40                  45

Pro Arg Gly Ala Ala Ala Arg Ala Thr Ser Val Ala Ala Pro Ala Ala
        50                  55                  60

Pro Ala Gly Ala Glu Glu Val Val Leu Gln Pro Ile Arg Glu Ile Ser
65                  70                  75                  80

Gly Ala Val Gln Leu Pro Gly Ser Lys Ser Leu Ser Asn Arg Ile Leu
                85                  90                  95

Leu Leu Ser Ala Leu Ser Glu Gly Thr Thr Val Val Asp Asn Leu Leu
            100                 105                 110

Asn Ser Glu Asp Val His Tyr Met Leu Glu Ala Leu Glu Ala Leu Gly
        115                 120                 125

Leu Ser Val Glu Ala Asp Lys Val Ala Lys Arg Ala Val Val Val Gly
130                 135                 140

Cys Gly Gly Arg Phe Pro Val Glu Lys Asp Ala Lys Glu Glu Val Lys
145                 150                 155                 160

Leu Phe Leu Gly Asn Ala Gly Thr Ala Met Arg Pro Leu Thr Ala Ala
                165                 170                 175

Val Val Ala Ala Gly Gly Asn Ala Thr Tyr Val Leu Asp Gly Val Pro
            180                 185                 190

Arg Met Arg Glu Arg Pro Ile Gly Asp Leu Val Val Gly Leu Gln Gln
        195                 200                 205

Leu Gly Ala Asp Val Asp Cys Phe Leu Gly Thr Asn Cys Pro Pro Val
    210                 215                 220

Arg Ile Asn Gly Lys Gly Gly Leu Pro Gly Gly Lys Val Lys Leu Ser
225                 230                 235                 240

Gly Ser Ile Ser Ser Gln Tyr Leu Ser Ser Leu Leu Met Ala Ala Pro
                245                 250                 255

Leu Ala Leu Glu Asp Val Glu Ile Glu Ile Ile Asp Lys Leu Ile Ser
```

-continued

```
                   260                 265                 270
Val Pro Tyr Val Glu Met Thr Leu Lys Leu Met Glu His Phe Gly Val
                275                 280                 285

Thr Ala Glu His Ser Asp Ser Trp Asp Arg Phe Tyr Ile Lys Gly Gly
                290                 295                 300

Gln Lys Tyr Lys Ser Pro Gly Asn Ala Tyr Val Glu Gly Asp Ala Ser
305                 310                 315                 320

Ser Ala Ser Tyr Phe Leu Ala Gly Ala Ile Thr Gly Gly Thr Val
                325                 330                 335

Thr Val Glu Gly Cys Gly Thr Thr Ser Leu Gln Gly Asp Val Lys Phe
                340                 345                 350

Ala Glu Val Leu Glu Met Met Gly Ala Lys Val Thr Trp Thr Asp Thr
                355                 360                 365

Ser Val Thr Val Thr Gly Pro Pro Arg Gln Pro Phe Gly Arg Lys His
                370                 375                 380

Leu Lys Ala Val Asp Val Asn Met Asn Lys Met Pro Asp Val Ala Met
385                 390                 395                 400

Thr Leu Ala Val Val Ala Leu Phe Ala Asp Gly Pro Thr Ala Ile Arg
                405                 410                 415

Asp Val Ala Ser Trp Arg Val Lys Glu Thr Glu Arg Met Val Ala Ile
                420                 425                 430

Arg Thr Glu Leu Thr Lys Leu Gly Ala Thr Val Glu Glu Gly Pro Asp
                435                 440                 445

Tyr Cys Ile Ile Thr Pro Pro Glu Lys Leu Asn Ile Thr Ala Ile Asp
                450                 455                 460

Thr Tyr Asp Asp His Arg Met Ala Met Ala Phe Ser Leu Ala Ala Cys
465                 470                 475                 480

Ala Glu Val Pro Val Thr Ile Arg Asp Pro Gly Cys Thr Arg Lys Thr
                485                 490                 495

Phe Pro Asn Tyr Phe Asp Val Leu Ser Thr Phe Val Lys Asn
                500                 505                 510

<210> SEQ ID NO 5
<211> LENGTH: 1368
<212> TYPE: PRT
<213> ORGANISM: Streptococcus pyogenes

<400> SEQUENCE: 5

Met Asp Lys Lys Tyr Ser Ile Gly Leu Asp Ile Gly Thr Asn Ser Val
1                   5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
                35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125
```

```
His Glu Lys Tyr Pro Thr Ile Tyr His Leu Arg Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
```

```
               545                 550                 555                 560
           Val Lys Gln Leu Lys Glu Asp Tyr Phe Lys Ile Glu Cys Phe Asp
                           565                 570                 575
           Ser Val Glu Ile Ser Gly Val Glu Asp Arg Phe Asn Ala Ser Leu Gly
                           580                 585                 590
           Thr Tyr His Asp Leu Leu Lys Ile Ile Lys Asp Lys Asp Phe Leu Asp
                           595                 600                 605
           Asn Glu Glu Asn Glu Asp Ile Leu Glu Asp Ile Val Leu Thr Leu Thr
               610                 615                 620
           Leu Phe Glu Asp Arg Glu Met Ile Glu Arg Leu Lys Thr Tyr Ala
           625                 630                 635                 640
           His Leu Phe Asp Asp Lys Val Met Lys Gln Leu Lys Arg Arg Arg Tyr
                           645                 650                 655
           Thr Gly Trp Gly Arg Leu Ser Arg Lys Leu Ile Asn Gly Ile Arg Asp
                           660                 665                 670
           Lys Gln Ser Gly Lys Thr Ile Leu Asp Phe Leu Lys Ser Asp Gly Phe
                           675                 680                 685
           Ala Asn Arg Asn Phe Met Gln Leu Ile His Asp Asp Ser Leu Thr Phe
               690                 695                 700
           Lys Glu Asp Ile Gln Lys Ala Gln Val Ser Gly Gln Gly Asp Ser Leu
           705                 710                 715                 720
           His Glu His Ile Ala Asn Leu Ala Gly Ser Pro Ala Ile Lys Lys Gly
                           725                 730                 735
           Ile Leu Gln Thr Val Lys Val Val Asp Glu Leu Val Lys Val Met Gly
                           740                 745                 750
           Arg His Lys Pro Glu Asn Ile Val Ile Glu Met Ala Arg Glu Asn Gln
                           755                 760                 765
           Thr Thr Gln Lys Gly Gln Lys Asn Ser Arg Glu Arg Met Lys Arg Ile
               770                 775                 780
           Glu Glu Gly Ile Lys Glu Leu Gly Ser Gln Ile Leu Lys Glu His Pro
           785                 790                 795                 800
           Val Glu Asn Thr Gln Leu Gln Asn Glu Lys Leu Tyr Leu Tyr Tyr Leu
                           805                 810                 815
           Gln Asn Gly Arg Asp Met Tyr Val Asp Gln Glu Leu Asp Ile Asn Arg
                           820                 825                 830
           Leu Ser Asp Tyr Asp Val Asp His Ile Val Pro Gln Ser Phe Leu Lys
                           835                 840                 845
           Asp Asp Ser Ile Asp Asn Lys Val Leu Thr Arg Ser Asp Lys Asn Arg
               850                 855                 860
           Gly Lys Ser Asp Asn Val Pro Ser Glu Glu Val Val Lys Lys Met Lys
           865                 870                 875                 880
           Asn Tyr Trp Arg Gln Leu Leu Asn Ala Lys Leu Ile Thr Gln Arg Lys
                           885                 890                 895
           Phe Asp Asn Leu Thr Lys Ala Glu Arg Gly Gly Leu Ser Glu Leu Asp
                           900                 905                 910
           Lys Ala Gly Phe Ile Lys Arg Gln Leu Val Glu Thr Arg Gln Ile Thr
                           915                 920                 925
           Lys His Val Ala Gln Ile Leu Asp Ser Arg Met Asn Thr Lys Tyr Asp
                           930                 935                 940
           Glu Asn Asp Lys Leu Ile Arg Glu Val Lys Val Ile Thr Leu Lys Ser
           945                 950                 955                 960
           Lys Leu Val Ser Asp Phe Arg Lys Asp Phe Gln Phe Tyr Lys Val Arg
                           965                 970                 975
```

-continued

```
Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
            995             1000            1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365
```

```
<210> SEQ ID NO 6
<211> LENGTH: 1384
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: dCas9

<400> SEQUENCE: 6

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
```

```
                770               775              780
Glu Glu Gly Ile Lys Glu Leu Gly Ser Gln Ile Leu Lys Glu His Pro
785               790              795              800

Val Glu Asn Thr Gln Leu Gln Asn Glu Lys Leu Tyr Leu Tyr Tyr Leu
              805              810              815

Gln Asn Gly Arg Asp Met Tyr Val Asp Gln Glu Leu Asp Ile Asn Arg
              820              825              830

Leu Ser Asp Tyr Asp Val Asp Ala Ile Val Pro Gln Ser Phe Leu Lys
              835              840              845

Asp Asp Ser Ile Asp Asn Lys Val Leu Thr Arg Ser Asp Lys Asn Arg
850               855              860

Gly Lys Ser Asp Asn Val Pro Ser Glu Glu Val Val Lys Met Lys
865               870              875              880

Asn Tyr Trp Arg Gln Leu Leu Asn Ala Lys Leu Ile Thr Gln Arg Lys
              885              890              895

Phe Asp Asn Leu Thr Lys Ala Glu Arg Gly Gly Leu Ser Glu Leu Asp
              900              905              910

Lys Ala Gly Phe Ile Lys Arg Gln Leu Val Glu Thr Arg Gln Ile Thr
              915              920              925

Lys His Val Ala Gln Ile Leu Asp Ser Arg Met Asn Thr Lys Tyr Asp
              930              935              940

Glu Asn Asp Lys Leu Ile Arg Glu Val Lys Val Ile Thr Leu Lys Ser
945               950              955              960

Lys Leu Val Ser Asp Phe Arg Lys Asp Phe Gln Phe Tyr Lys Val Arg
              965              970              975

Glu Ile Asn Asn Tyr His His Ala His Asp Ala Tyr Leu Asn Ala Val
              980              985              990

Val Gly Thr Ala Leu Ile Lys Lys Tyr Pro Lys Leu Glu Ser Glu Phe
              995             1000             1005

Val Tyr Gly Asp Tyr Lys Val Tyr Asp Val Arg Lys Met Ile Ala
             1010             1015             1020

Lys Ser Glu Gln Glu Ile Gly Lys Ala Thr Ala Lys Tyr Phe Phe
1025             1030             1035

Tyr Ser Asn Ile Met Asn Phe Phe Lys Thr Glu Ile Thr Leu Ala
1040             1045             1050

Asn Gly Glu Ile Arg Lys Arg Pro Leu Ile Glu Thr Asn Gly Glu
1055             1060             1065

Thr Gly Glu Ile Val Trp Asp Lys Gly Arg Asp Phe Ala Thr Val
1070             1075             1080

Arg Lys Val Leu Ser Met Pro Gln Val Asn Ile Val Lys Lys Thr
1085             1090             1095

Glu Val Gln Thr Gly Gly Phe Ser Lys Glu Ser Ile Leu Pro Lys
1100             1105             1110

Arg Asn Ser Asp Lys Leu Ile Ala Arg Lys Lys Asp Trp Asp Pro
1115             1120             1125

Lys Lys Tyr Gly Gly Phe Asp Ser Pro Thr Val Ala Tyr Ser Val
1130             1135             1140

Leu Val Val Ala Lys Val Glu Lys Gly Lys Ser Lys Lys Leu Lys
1145             1150             1155

Ser Val Lys Glu Leu Leu Gly Ile Thr Ile Met Glu Arg Ser Ser
1160             1165             1170

Phe Glu Lys Asn Pro Ile Asp Phe Leu Glu Ala Lys Gly Tyr Lys
1175             1180             1185
```

-continued

```
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Lys Arg Pro Ala Ala Thr Lys Lys Ala Gly Gln Ala Lys Lys Lys
    1370                1375                1380

Lys

<210> SEQ ID NO 7
<211> LENGTH: 1384
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: nCas9(D10A)

<400> SEQUENCE: 7

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

-continued

```
His Glu Lys Tyr Pro Thr Ile Tyr His Leu Arg Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

```
                545                 550                 555                 560
            Val Lys Gln Leu Lys Glu Asp Tyr Phe Lys Ile Glu Cys Phe Asp
                            565                 570                 575
            Ser Val Glu Ile Ser Gly Val Glu Asp Arg Phe Asn Ala Ser Leu Gly
                            580                 585                 590
            Thr Tyr His Asp Leu Leu Lys Ile Ile Lys Asp Lys Asp Phe Leu Asp
                            595                 600                 605
            Asn Glu Glu Asn Glu Asp Ile Leu Glu Asp Ile Val Leu Thr Leu Thr
            610                 615                 620
            Leu Phe Glu Asp Arg Glu Met Ile Glu Arg Leu Lys Thr Tyr Ala
            625                 630                 635                 640
            His Leu Phe Asp Asp Lys Val Met Lys Gln Leu Lys Arg Arg Arg Tyr
                            645                 650                 655
            Thr Gly Trp Gly Arg Leu Ser Arg Lys Leu Ile Asn Gly Ile Arg Asp
                            660                 665                 670
            Lys Gln Ser Gly Lys Thr Ile Leu Asp Phe Leu Lys Ser Asp Gly Phe
                            675                 680                 685
            Ala Asn Arg Asn Phe Met Gln Leu Ile His Asp Asp Ser Leu Thr Phe
            690                 695                 700
            Lys Glu Asp Ile Gln Lys Ala Gln Val Ser Gly Gln Gly Asp Ser Leu
            705                 710                 715                 720
            His Glu His Ile Ala Asn Leu Ala Gly Ser Pro Ala Ile Lys Lys Gly
                            725                 730                 735
            Ile Leu Gln Thr Val Lys Val Val Asp Glu Leu Val Lys Val Met Gly
                            740                 745                 750
            Arg His Lys Pro Glu Asn Ile Val Ile Glu Met Ala Arg Glu Asn Gln
                            755                 760                 765
            Thr Thr Gln Lys Gly Gln Lys Asn Ser Arg Glu Arg Met Lys Arg Ile
            770                 775                 780
            Glu Glu Gly Ile Lys Glu Leu Gly Ser Gln Ile Leu Lys Glu His Pro
            785                 790                 795                 800
            Val Glu Asn Thr Gln Leu Gln Asn Glu Lys Leu Tyr Leu Tyr Tyr Leu
                            805                 810                 815
            Gln Asn Gly Arg Asp Met Tyr Val Asp Gln Glu Leu Asp Ile Asn Arg
                            820                 825                 830
            Leu Ser Asp Tyr Asp Val Asp His Ile Val Pro Gln Ser Phe Leu Lys
                            835                 840                 845
            Asp Asp Ser Ile Asp Asn Lys Val Leu Thr Arg Ser Asp Lys Asn Arg
            850                 855                 860
            Gly Lys Ser Asp Asn Val Pro Ser Glu Glu Val Val Lys Lys Met Lys
            865                 870                 875                 880
            Asn Tyr Trp Arg Gln Leu Leu Asn Ala Lys Leu Ile Thr Gln Arg Lys
                            885                 890                 895
            Phe Asp Asn Leu Thr Lys Ala Glu Arg Gly Gly Leu Ser Glu Leu Asp
                            900                 905                 910
            Lys Ala Gly Phe Ile Lys Arg Gln Leu Val Glu Thr Arg Gln Ile Thr
                            915                 920                 925
            Lys His Val Ala Gln Ile Leu Asp Ser Arg Met Asn Thr Lys Tyr Asp
                            930                 935                 940
            Glu Asn Asp Lys Leu Ile Arg Glu Val Lys Val Ile Thr Leu Lys Ser
            945                 950                 955                 960
            Lys Leu Val Ser Asp Phe Arg Lys Asp Phe Gln Phe Tyr Lys Val Arg
                            965                 970                 975
```

```
Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365
```

-continued

```
Lys Arg Pro Ala Ala Thr Lys Lys Ala Gly Gln Ala Lys Lys Lys
    1370                1375                1380
Lys
```

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: XTEN

<400> SEQUENCE: 8

```
Lys Ser Gly Ser Glu Thr Pro Gly Thr Ser Glu Ser Ala Thr Pro Glu
1               5                   10                  15
```

<210> SEQ ID NO 9
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: UGI

<400> SEQUENCE: 9

```
Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu
```

<210> SEQ ID NO 10
<211> LENGTH: 1737
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NLS-APOBEC1-XTEN-nCas9-UGI-NLS fusion protein

<400> SEQUENCE: 10

```
Met Pro Lys Lys Lys Arg Lys Val Ser Ser Glu Thr Gly Pro Val Ala
1               5                   10                  15

Val Asp Pro Thr Leu Arg Arg Arg Ile Glu Pro His Glu Phe Glu Val
            20                  25                  30

Phe Phe Asp Pro Arg Glu Leu Arg Lys Glu Thr Cys Leu Leu Tyr Glu
        35                  40                  45

Ile Asn Trp Gly Gly Arg His Ser Ile Trp Arg His Thr Ser Gln Asn
    50                  55                  60

Thr Asn Lys His Val Glu Val Asn Phe Ile Glu Lys Phe Thr Thr Glu
65                  70                  75                  80
```

```
Arg Tyr Phe Cys Pro Asn Thr Arg Cys Ser Ile Thr Trp Phe Leu Ser
                85                  90                  95

Trp Ser Pro Cys Gly Glu Cys Ser Arg Ala Ile Thr Glu Phe Leu Ser
            100                 105                 110

Arg Tyr Pro His Val Thr Leu Phe Ile Tyr Ile Ala Arg Leu Tyr His
        115                 120                 125

His Ala Asp Pro Arg Asn Arg Gln Gly Leu Arg Asp Leu Ile Ser Ser
    130                 135                 140

Gly Val Thr Ile Gln Ile Met Thr Glu Gln Ser Gly Tyr Cys Trp
145                 150                 155                 160

Arg Asn Phe Val Asn Tyr Ser Pro Ser Asn Glu Ala His Trp Pro Arg
                165                 170                 175

Tyr Pro His Leu Trp Val Arg Leu Tyr Val Leu Glu Leu Tyr Cys Ile
            180                 185                 190

Ile Leu Gly Leu Pro Pro Cys Leu Asn Ile Leu Arg Arg Lys Gln Pro
            195                 200                 205

Gln Leu Thr Phe Phe Thr Ile Ala Leu Gln Ser Cys His Tyr Gln Arg
    210                 215                 220

Leu Pro Pro His Ile Leu Trp Ala Thr Gly Leu Lys Ser Gly Ser Glu
225                 230                 235                 240

Thr Pro Gly Thr Ser Glu Ser Ala Thr Pro Glu Leu Lys Asp Lys Lys
                245                 250                 255

Tyr Ser Ile Gly Leu Ala Ile Gly Thr Asn Ser Val Gly Trp Ala Val
                260                 265                 270

Ile Thr Asp Glu Tyr Lys Val Pro Ser Lys Lys Phe Lys Val Leu Gly
        275                 280                 285

Asn Thr Asp Arg His Ser Ile Lys Lys Asn Leu Ile Gly Ala Leu Leu
    290                 295                 300

Phe Asp Ser Gly Glu Thr Ala Glu Ala Thr Arg Leu Lys Arg Thr Ala
305                 310                 315                 320

Arg Arg Arg Tyr Thr Arg Arg Lys Asn Arg Ile Cys Tyr Leu Gln Glu
                325                 330                 335

Ile Phe Ser Asn Glu Met Ala Lys Val Asp Asp Ser Phe Phe His Arg
            340                 345                 350

Leu Glu Glu Ser Phe Leu Val Glu Glu Asp Lys Lys His Glu Arg His
        355                 360                 365

Pro Ile Phe Gly Asn Ile Val Asp Glu Val Ala Tyr His Glu Lys Tyr
    370                 375                 380

Pro Thr Ile Tyr His Leu Arg Lys Lys Leu Val Asp Ser Thr Asp Lys
385                 390                 395                 400

Ala Asp Leu Arg Leu Ile Tyr Leu Ala Leu Ala His Met Ile Lys Phe
                405                 410                 415

Arg Gly His Phe Leu Ile Glu Gly Asp Leu Asn Pro Asp Asn Ser Asp
            420                 425                 430

Val Asp Lys Leu Phe Ile Gln Leu Val Gln Thr Tyr Asn Gln Leu Phe
        435                 440                 445

Glu Glu Asn Pro Ile Asn Ala Ser Gly Val Asp Ala Lys Ala Ile Leu
    450                 455                 460

Ser Ala Arg Leu Ser Lys Ser Arg Arg Leu Glu Asn Leu Ile Ala Gln
465                 470                 475                 480

Leu Pro Gly Glu Lys Lys Asn Gly Leu Phe Gly Asn Leu Ile Ala Leu
                485                 490                 495

Ser Leu Gly Leu Thr Pro Asn Phe Lys Ser Asn Phe Asp Leu Ala Glu
```

```
                500             505             510
Asp Ala Lys Leu Gln Leu Ser Lys Asp Thr Tyr Asp Asp Leu Asp
            515             520             525
Asn Leu Leu Ala Gln Ile Gly Asp Gln Tyr Ala Asp Leu Phe Leu Ala
        530             535             540
Ala Lys Asn Leu Ser Asp Ala Ile Leu Leu Ser Asp Ile Leu Arg Val
545             550             555             560
Asn Thr Glu Ile Thr Lys Ala Pro Leu Ser Ala Ser Met Ile Lys Arg
            565             570             575
Tyr Asp Glu His His Gln Asp Leu Thr Leu Leu Lys Ala Leu Val Arg
            580             585             590
Gln Gln Leu Pro Glu Lys Tyr Lys Glu Ile Phe Phe Asp Gln Ser Lys
        595             600             605
Asn Gly Tyr Ala Gly Tyr Ile Asp Gly Gly Ala Ser Gln Glu Glu Phe
        610             615             620
Tyr Lys Phe Ile Lys Pro Ile Leu Glu Lys Met Asp Gly Thr Glu Glu
625             630             635             640
Leu Leu Val Lys Leu Asn Arg Glu Asp Leu Leu Arg Lys Gln Arg Thr
            645             650             655
Phe Asp Asn Gly Ser Ile Pro His Gln Ile His Leu Gly Glu Leu His
            660             665             670
Ala Ile Leu Arg Arg Gln Glu Asp Phe Tyr Pro Phe Leu Lys Asp Asn
            675             680             685
Arg Glu Lys Ile Glu Lys Ile Leu Thr Phe Arg Ile Pro Tyr Tyr Val
        690             695             700
Gly Pro Leu Ala Arg Gly Asn Ser Arg Phe Ala Trp Met Thr Arg Lys
705             710             715             720
Ser Glu Glu Thr Ile Thr Pro Trp Asn Phe Glu Val Val Asp Lys
            725             730             735
Gly Ala Ser Ala Gln Ser Phe Ile Glu Arg Met Thr Asn Phe Asp Lys
            740             745             750
Asn Leu Pro Asn Glu Lys Val Leu Pro Lys His Ser Leu Leu Tyr Glu
            755             760             765
Tyr Phe Thr Val Tyr Asn Glu Leu Thr Lys Val Lys Tyr Val Thr Glu
            770             775             780
Gly Met Arg Lys Pro Ala Phe Leu Ser Gly Glu Gln Lys Lys Ala Ile
785             790             795             800
Val Asp Leu Leu Phe Lys Thr Asn Arg Lys Val Thr Val Lys Gln Leu
            805             810             815
Lys Glu Asp Tyr Phe Lys Lys Ile Glu Cys Phe Asp Ser Val Glu Ile
            820             825             830
Ser Gly Val Glu Asp Arg Phe Asn Ala Ser Leu Gly Thr Tyr His Asp
            835             840             845
Leu Leu Lys Ile Ile Lys Asp Lys Asp Phe Leu Asp Asn Glu Glu Asn
        850             855             860
Glu Asp Ile Leu Glu Asp Ile Val Leu Thr Leu Thr Leu Phe Glu Asp
865             870             875             880
Arg Glu Met Ile Glu Glu Arg Leu Lys Thr Tyr Ala His Leu Phe Asp
                885             890             895
Asp Lys Val Met Lys Gln Leu Lys Arg Arg Arg Tyr Thr Gly Trp Gly
            900             905             910
Arg Leu Ser Arg Lys Leu Ile Asn Gly Ile Arg Asp Lys Gln Ser Gly
            915             920             925
```

```
Lys Thr Ile Leu Asp Phe Leu Lys Ser Asp Gly Phe Ala Asn Arg Asn
    930                 935                 940

Phe Met Gln Leu Ile His Asp Asp Ser Leu Thr Phe Lys Glu Asp Ile
945                 950                 955                 960

Gln Lys Ala Gln Val Ser Gly Gln Gly Asp Ser Leu His Glu His Ile
                965                 970                 975

Ala Asn Leu Ala Gly Ser Pro Ala Ile Lys Lys Gly Ile Leu Gln Thr
                980                 985                 990

Val Lys Val Val Asp Glu Leu Val Lys Val Met Gly Arg His Lys Pro
            995                 1000                1005

Glu Asn Ile Val Ile Glu Met Ala Arg Glu Asn Gln Thr Thr Gln
        1010                1015                1020

Lys Gly Gln Lys Asn Ser Arg Glu Arg Met Lys Arg Ile Glu Glu
        1025                1030                1035

Gly Ile Lys Glu Leu Gly Ser Gln Ile Leu Lys Glu His Pro Val
        1040                1045                1050

Glu Asn Thr Gln Leu Gln Asn Glu Lys Leu Tyr Leu Tyr Tyr Leu
        1055                1060                1065

Gln Asn Gly Arg Asp Met Tyr Val Asp Gln Glu Leu Asp Ile Asn
        1070                1075                1080

Arg Leu Ser Asp Tyr Asp Val Asp His Ile Val Pro Gln Ser Phe
        1085                1090                1095

Leu Lys Asp Asp Ser Ile Asp Asn Lys Val Leu Thr Arg Ser Asp
        1100                1105                1110

Lys Asn Arg Gly Lys Ser Asp Asn Val Pro Ser Glu Glu Val Val
        1115                1120                1125

Lys Lys Met Lys Asn Tyr Trp Arg Gln Leu Leu Asn Ala Lys Leu
        1130                1135                1140

Ile Thr Gln Arg Lys Phe Asp Asn Leu Thr Lys Ala Glu Arg Gly
        1145                1150                1155

Gly Leu Ser Glu Leu Asp Lys Ala Gly Phe Ile Lys Arg Gln Leu
        1160                1165                1170

Val Glu Thr Arg Gln Ile Thr Lys His Val Ala Gln Ile Leu Asp
        1175                1180                1185

Ser Arg Met Asn Thr Lys Tyr Asp Glu Asn Asp Lys Leu Ile Arg
        1190                1195                1200

Glu Val Lys Val Ile Thr Leu Lys Ser Lys Leu Val Ser Asp Phe
        1205                1210                1215

Arg Lys Asp Phe Gln Phe Tyr Lys Val Arg Glu Ile Asn Asn Tyr
        1220                1225                1230

His His Ala His Asp Ala Tyr Leu Asn Ala Val Val Gly Thr Ala
        1235                1240                1245

Leu Ile Lys Lys Tyr Pro Lys Leu Glu Ser Glu Phe Val Tyr Gly
        1250                1255                1260

Asp Tyr Lys Val Tyr Asp Val Arg Lys Met Ile Ala Lys Ser Glu
        1265                1270                1275

Gln Glu Ile Gly Lys Ala Thr Ala Lys Tyr Phe Phe Tyr Ser Asn
        1280                1285                1290

Ile Met Asn Phe Phe Lys Thr Glu Ile Thr Leu Ala Asn Gly Glu
        1295                1300                1305

Ile Arg Lys Arg Pro Leu Ile Glu Thr Asn Gly Glu Thr Gly Glu
        1310                1315                1320
```

```
Ile Val Trp Asp Lys Gly Arg Asp Phe Ala Thr Val Arg Lys Val
    1325              1330                1335

Leu Ser Met Pro Gln Val Asn Ile Val Lys Lys Thr Glu Val Gln
    1340              1345                1350

Thr Gly Gly Phe Ser Lys Glu Ser Ile Leu Pro Lys Arg Asn Ser
    1355              1360                1365

Asp Lys Leu Ile Ala Arg Lys Lys Asp Trp Asp Pro Lys Lys Tyr
    1370              1375                1380

Gly Gly Phe Asp Ser Pro Thr Val Ala Tyr Ser Val Leu Val Val
    1385              1390                1395

Ala Lys Val Glu Lys Gly Lys Ser Lys Lys Leu Lys Ser Val Lys
    1400              1405                1410

Glu Leu Leu Gly Ile Thr Ile Met Glu Arg Ser Ser Phe Glu Lys
    1415              1420                1425

Asn Pro Ile Asp Phe Leu Glu Ala Lys Gly Tyr Lys Glu Val Lys
    1430              1435                1440

Lys Asp Leu Ile Ile Lys Leu Pro Lys Tyr Ser Leu Phe Glu Leu
    1445              1450                1455

Glu Asn Gly Arg Lys Arg Met Leu Ala Ser Ala Gly Glu Leu Gln
    1460              1465                1470

Lys Gly Asn Glu Leu Ala Leu Pro Ser Lys Tyr Val Asn Phe Leu
    1475              1480                1485

Tyr Leu Ala Ser His Tyr Glu Lys Leu Lys Gly Ser Pro Glu Asp
    1490              1495                1500

Asn Glu Gln Lys Gln Leu Phe Val Glu Gln His Lys His Tyr Leu
    1505              1510                1515

Asp Glu Ile Ile Glu Gln Ile Ser Glu Phe Ser Lys Arg Val Ile
    1520              1525                1530

Leu Ala Asp Ala Asn Leu Asp Lys Val Leu Ser Ala Tyr Asn Lys
    1535              1540                1545

His Arg Asp Lys Pro Ile Arg Glu Gln Ala Glu Asn Ile Ile His
    1550              1555                1560

Leu Phe Thr Leu Thr Asn Leu Gly Ala Pro Ala Ala Phe Lys Tyr
    1565              1570                1575

Phe Asp Thr Thr Ile Asp Arg Lys Arg Tyr Thr Ser Thr Lys Glu
    1580              1585                1590

Val Leu Asp Ala Thr Leu Ile His Gln Ser Ile Thr Gly Leu Tyr
    1595              1600                1605

Glu Thr Arg Ile Asp Leu Ser Gln Leu Gly Gly Asp Lys Arg Pro
    1610              1615                1620

Ala Ala Thr Lys Lys Ala Gly Gln Ala Lys Lys Lys Lys Thr Arg
    1625              1630                1635

Asp Ser Gly Gly Ser Thr Asn Leu Ser Asp Ile Ile Glu Lys Glu
    1640              1645                1650

Thr Gly Lys Gln Leu Val Ile Gln Glu Ser Ile Leu Met Leu Pro
    1655              1660                1665

Glu Glu Val Glu Glu Val Ile Gly Asn Lys Pro Glu Ser Asp Ile
    1670              1675                1680

Leu Val His Thr Ala Tyr Asp Glu Ser Thr Asp Glu Asn Val Met
    1685              1690                1695

Leu Leu Thr Ser Asp Ala Pro Glu Tyr Lys Pro Trp Ala Leu Val
    1700              1705                1710

Ile Gln Asp Ser Asn Gly Glu Asn Lys Ile Lys Met Leu Ser Gly
```

```
                  1715                1720                1725
Gly Ser   Pro Lys Lys Lys Arg   Lys Val
         1730                1735

<210> SEQ ID NO 11
<211> LENGTH: 1737
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NLS-APOBEC1-XTEN-dCas9-UGI-NLS fusion protein

<400> SEQUENCE: 11

Met Pro Lys Lys Lys Arg Lys Val Ser Ser Glu Thr Gly Pro Val Ala
1               5                   10                  15

Val Asp Pro Thr Leu Arg Arg Ile Glu Pro His Glu Phe Glu Val
            20                  25                  30

Phe Phe Asp Pro Arg Glu Leu Arg Lys Glu Thr Cys Leu Leu Tyr Glu
        35                  40                  45

Ile Asn Trp Gly Gly Arg His Ser Ile Trp Arg His Thr Ser Gln Asn
    50                  55                  60

Thr Asn Lys His Val Glu Val Asn Phe Ile Glu Lys Phe Thr Thr Glu
65              70                  75                  80

Arg Tyr Phe Cys Pro Asn Thr Arg Cys Ser Ile Thr Trp Phe Leu Ser
                85                  90                  95

Trp Ser Pro Cys Gly Glu Cys Ser Arg Ala Ile Thr Glu Phe Leu Ser
            100                 105                 110

Arg Tyr Pro His Val Thr Leu Phe Ile Tyr Ile Ala Arg Leu Tyr His
        115                 120                 125

His Ala Asp Pro Arg Asn Arg Gln Gly Leu Arg Asp Leu Ile Ser Ser
    130                 135                 140

Gly Val Thr Ile Gln Ile Met Thr Glu Gln Glu Ser Gly Tyr Cys Trp
145                 150                 155                 160

Arg Asn Phe Val Asn Tyr Ser Pro Ser Asn Glu Ala His Trp Pro Arg
                165                 170                 175

Tyr Pro His Leu Trp Val Arg Leu Tyr Val Leu Glu Leu Tyr Cys Ile
            180                 185                 190

Ile Leu Gly Leu Pro Pro Cys Leu Asn Ile Leu Arg Arg Lys Gln Pro
        195                 200                 205

Gln Leu Thr Phe Phe Thr Ile Ala Leu Gln Ser Cys His Tyr Gln Arg
    210                 215                 220

Leu Pro Pro His Ile Leu Trp Ala Thr Gly Leu Lys Ser Gly Ser Glu
225                 230                 235                 240

Thr Pro Gly Thr Ser Glu Ser Ala Thr Pro Glu Leu Lys Asp Lys Lys
                245                 250                 255

Tyr Ser Ile Gly Leu Ala Ile Gly Thr Asn Ser Val Gly Trp Ala Val
            260                 265                 270

Ile Thr Asp Glu Tyr Lys Val Pro Ser Lys Lys Phe Lys Val Leu Gly
        275                 280                 285

Asn Thr Asp Arg His Ser Ile Lys Lys Asn Leu Ile Gly Ala Leu Leu
    290                 295                 300

Phe Asp Ser Gly Glu Thr Ala Glu Ala Thr Arg Leu Lys Arg Thr Ala
305                 310                 315                 320

Arg Arg Arg Tyr Thr Arg Arg Lys Asn Arg Ile Cys Tyr Leu Gln Glu
```

```
            325                 330                 335
Ile Phe Ser Asn Glu Met Ala Lys Val Asp Asp Ser Phe Phe His Arg
            340                 345                 350
Leu Glu Glu Ser Phe Leu Val Glu Glu Asp Lys Lys His Glu Arg His
            355                 360                 365
Pro Ile Phe Gly Asn Ile Val Asp Glu Val Ala Tyr His Glu Lys Tyr
            370                 375                 380
Pro Thr Ile Tyr His Leu Arg Lys Lys Leu Val Asp Ser Thr Asp Lys
385                 390                 395                 400
Ala Asp Leu Arg Leu Ile Tyr Leu Ala Leu Ala His Met Ile Lys Phe
            405                 410                 415
Arg Gly His Phe Leu Ile Glu Gly Asp Leu Asn Pro Asp Asn Ser Asp
            420                 425                 430
Val Asp Lys Leu Phe Ile Gln Leu Val Gln Thr Tyr Asn Gln Leu Phe
            435                 440                 445
Glu Glu Asn Pro Ile Asn Ala Ser Gly Val Asp Ala Lys Ala Ile Leu
            450                 455                 460
Ser Ala Arg Leu Ser Lys Ser Arg Arg Leu Glu Asn Leu Ile Ala Gln
465                 470                 475                 480
Leu Pro Gly Glu Lys Lys Asn Gly Leu Phe Gly Asn Leu Ile Ala Leu
            485                 490                 495
Ser Leu Gly Leu Thr Pro Asn Phe Lys Ser Asn Phe Asp Leu Ala Glu
            500                 505                 510
Asp Ala Lys Leu Gln Leu Ser Lys Asp Thr Tyr Asp Asp Asp Leu Asp
            515                 520                 525
Asn Leu Leu Ala Gln Ile Gly Asp Gln Tyr Ala Asp Leu Phe Leu Ala
            530                 535                 540
Ala Lys Asn Leu Ser Asp Ala Ile Leu Leu Ser Asp Ile Leu Arg Val
545                 550                 555                 560
Asn Thr Glu Ile Thr Lys Ala Pro Leu Ser Ala Ser Met Ile Lys Arg
            565                 570                 575
Tyr Asp Glu His His Gln Asp Leu Thr Leu Leu Lys Ala Leu Val Arg
            580                 585                 590
Gln Gln Leu Pro Glu Lys Tyr Lys Glu Ile Phe Phe Asp Gln Ser Lys
            595                 600                 605
Asn Gly Tyr Ala Gly Tyr Ile Asp Gly Gly Ala Ser Gln Glu Glu Phe
            610                 615                 620
Tyr Lys Phe Ile Lys Pro Ile Leu Glu Lys Met Asp Gly Thr Glu Glu
625                 630                 635                 640
Leu Leu Val Lys Leu Asn Arg Glu Asp Leu Leu Arg Lys Gln Arg Thr
            645                 650                 655
Phe Asp Asn Gly Ser Ile Pro His Gln Ile His Leu Gly Glu Leu His
            660                 665                 670
Ala Ile Leu Arg Arg Gln Glu Asp Phe Tyr Pro Phe Leu Lys Asp Asn
            675                 680                 685
Arg Glu Lys Ile Glu Lys Ile Leu Thr Phe Arg Ile Pro Tyr Tyr Val
            690                 695                 700
Gly Pro Leu Ala Arg Gly Asn Ser Arg Phe Ala Trp Met Thr Arg Lys
705                 710                 715                 720
Ser Glu Glu Thr Ile Thr Pro Trp Asn Phe Glu Glu Val Val Asp Lys
            725                 730                 735
Gly Ala Ser Ala Gln Ser Phe Ile Glu Arg Met Thr Asn Phe Asp Lys
            740                 745                 750
```

```
Asn Leu Pro Asn Glu Lys Val Leu Pro Lys His Ser Leu Leu Tyr Glu
        755                 760                 765

Tyr Phe Thr Val Tyr Asn Glu Leu Thr Lys Val Lys Tyr Val Thr Glu
        770                 775                 780

Gly Met Arg Lys Pro Ala Phe Leu Ser Gly Glu Gln Lys Lys Ala Ile
785                 790                 795                 800

Val Asp Leu Leu Phe Lys Thr Asn Arg Lys Val Thr Val Lys Gln Leu
                805                 810                 815

Lys Glu Asp Tyr Phe Lys Lys Ile Glu Cys Phe Asp Ser Val Glu Ile
                820                 825                 830

Ser Gly Val Glu Asp Arg Phe Asn Ala Ser Leu Gly Thr Tyr His Asp
                835                 840                 845

Leu Leu Lys Ile Ile Lys Asp Lys Asp Phe Leu Asp Asn Glu Glu Asn
        850                 855                 860

Glu Asp Ile Leu Glu Asp Ile Val Leu Thr Leu Thr Leu Phe Glu Asp
865                 870                 875                 880

Arg Glu Met Ile Glu Glu Arg Leu Lys Thr Tyr Ala His Leu Phe Asp
                        885                 890                 895

Asp Lys Val Met Lys Gln Leu Lys Arg Arg Arg Tyr Thr Gly Trp Gly
                900                 905                 910

Arg Leu Ser Arg Lys Leu Ile Asn Gly Ile Arg Asp Lys Gln Ser Gly
                915                 920                 925

Lys Thr Ile Leu Asp Phe Leu Lys Ser Asp Gly Phe Ala Asn Arg Asn
        930                 935                 940

Phe Met Gln Leu Ile His Asp Asp Ser Leu Thr Phe Lys Glu Asp Ile
945                 950                 955                 960

Gln Lys Ala Gln Val Ser Gly Gln Gly Asp Ser Leu His Glu His Ile
                965                 970                 975

Ala Asn Leu Ala Gly Ser Pro Ala Ile Lys Lys Gly Ile Leu Gln Thr
                980                 985                 990

Val Lys Val Val Asp Glu Leu Val  Lys Val Met Gly Arg  His Lys Pro
        995                 1000                1005

Glu Asn Ile Val Ile Glu Met  Ala Arg Glu Asn Gln  Thr Thr Gln
        1010                1015                1020

Lys Gly Gln Lys Asn Ser Arg  Glu Arg Met Lys Arg  Ile Glu Glu
        1025                1030                1035

Gly Ile Lys Glu Leu Gly Ser  Gln Ile Leu Lys Glu  His Pro Val
        1040                1045                1050

Glu Asn Thr Gln Leu Gln Asn  Glu Lys Leu Tyr Leu  Tyr Tyr Leu
        1055                1060                1065

Gln Asn Gly Arg Asp Met Tyr  Val Asp Gln Glu Leu  Asp Ile Asn
        1070                1075                1080

Arg Leu Ser Asp Tyr Asp Val  Asp Ala Ile Val Pro  Gln Ser Phe
        1085                1090                1095

Leu Lys Asp Asp Ser Ile Asp  Asn Lys Val Leu Thr  Arg Ser Asp
        1100                1105                1110

Lys Asn Arg Gly Lys Ser Asp  Asn Val Pro Ser Glu  Glu Val Val
        1115                1120                1125

Lys Lys Met Lys Asn Tyr Trp  Arg Gln Leu Leu Asn  Ala Lys Leu
        1130                1135                1140

Ile Thr Gln Arg Lys Phe Asp  Asn Leu Thr Lys Ala  Glu Arg Gly
        1145                1150                1155
```

```
Gly Leu Ser Glu Leu Asp Lys Ala Gly Phe Ile Lys Arg Gln Leu
    1160                1165                1170

Val Glu Thr Arg Gln Ile Thr Lys His Val Ala Gln Ile Leu Asp
    1175                1180                1185

Ser Arg Met Asn Thr Lys Tyr Asp Glu Asn Asp Lys Leu Ile Arg
    1190                1195                1200

Glu Val Lys Val Ile Thr Leu Lys Ser Lys Leu Val Ser Asp Phe
    1205                1210                1215

Arg Lys Asp Phe Gln Phe Tyr Lys Val Arg Glu Ile Asn Asn Tyr
    1220                1225                1230

His His Ala His Asp Ala Tyr Leu Asn Ala Val Val Gly Thr Ala
    1235                1240                1245

Leu Ile Lys Lys Tyr Pro Lys Leu Glu Ser Glu Phe Val Tyr Gly
    1250                1255                1260

Asp Tyr Lys Val Tyr Asp Val Arg Lys Met Ile Ala Lys Ser Glu
    1265                1270                1275

Gln Glu Ile Gly Lys Ala Thr Ala Lys Tyr Phe Phe Tyr Ser Asn
    1280                1285                1290

Ile Met Asn Phe Phe Lys Thr Glu Ile Thr Leu Ala Asn Gly Glu
    1295                1300                1305

Ile Arg Lys Arg Pro Leu Ile Glu Thr Asn Gly Glu Thr Gly Glu
    1310                1315                1320

Ile Val Trp Asp Lys Gly Arg Asp Phe Ala Thr Val Arg Lys Val
    1325                1330                1335

Leu Ser Met Pro Gln Val Asn Ile Val Lys Lys Thr Glu Val Gln
    1340                1345                1350

Thr Gly Gly Phe Ser Lys Glu Ser Ile Leu Pro Lys Arg Asn Ser
    1355                1360                1365

Asp Lys Leu Ile Ala Arg Lys Lys Asp Trp Asp Pro Lys Lys Tyr
    1370                1375                1380

Gly Gly Phe Asp Ser Pro Thr Val Ala Tyr Ser Val Leu Val Val
    1385                1390                1395

Ala Lys Val Glu Lys Gly Lys Ser Lys Lys Leu Lys Ser Val Lys
    1400                1405                1410

Glu Leu Leu Gly Ile Thr Ile Met Glu Arg Ser Ser Phe Glu Lys
    1415                1420                1425

Asn Pro Ile Asp Phe Leu Glu Ala Lys Gly Tyr Lys Glu Val Lys
    1430                1435                1440

Lys Asp Leu Ile Ile Lys Leu Pro Lys Tyr Ser Leu Phe Glu Leu
    1445                1450                1455

Glu Asn Gly Arg Lys Arg Met Leu Ala Ser Ala Gly Glu Leu Gln
    1460                1465                1470

Lys Gly Asn Glu Leu Ala Leu Pro Ser Lys Tyr Val Asn Phe Leu
    1475                1480                1485

Tyr Leu Ala Ser His Tyr Glu Lys Leu Lys Gly Ser Pro Glu Asp
    1490                1495                1500

Asn Glu Gln Lys Gln Leu Phe Val Glu Gln His Lys His Tyr Leu
    1505                1510                1515

Asp Glu Ile Ile Glu Gln Ile Ser Glu Phe Ser Lys Arg Val Ile
    1520                1525                1530

Leu Ala Asp Ala Asn Leu Asp Lys Val Leu Ser Ala Tyr Asn Lys
    1535                1540                1545

His Arg Asp Lys Pro Ile Arg Glu Gln Ala Glu Asn Ile Ile His
```

| | | | | | | | | | | |
|---|---|---|---|---|---|---|---|---|---|---|
| | | | | 1550 | | | 1555 | | | 1560 |
| Leu | Phe | Thr | Leu | Thr | Asn | Leu | Gly | Ala | Pro | Ala | Ala | Phe | Lys | Tyr |
| | 1565 | | | | 1570 | | | | 1575 | |
| Phe | Asp | Thr | Thr | Ile | Asp | Arg | Lys | Arg | Tyr | Thr | Ser | Thr | Lys | Glu |
| | 1580 | | | | 1585 | | | | 1590 | |
| Val | Leu | Asp | Ala | Thr | Leu | Ile | His | Gln | Ser | Ile | Thr | Gly | Leu | Tyr |
| | 1595 | | | | 1600 | | | | 1605 | |
| Glu | Thr | Arg | Ile | Asp | Leu | Ser | Gln | Leu | Gly | Gly | Asp | Lys | Arg | Pro |
| | 1610 | | | | 1615 | | | | 1620 | |
| Ala | Ala | Thr | Lys | Lys | Ala | Gly | Gln | Ala | Lys | Lys | Lys | Thr | Arg |
| | 1625 | | | | 1630 | | | | 1635 | |
| Asp | Ser | Gly | Gly | Ser | Thr | Asn | Leu | Ser | Asp | Ile | Ile | Glu | Lys | Glu |
| | 1640 | | | | 1645 | | | | 1650 | |
| Thr | Gly | Lys | Gln | Leu | Val | Ile | Gln | Glu | Ser | Ile | Leu | Met | Leu | Pro |
| | 1655 | | | | 1660 | | | | 1665 | |
| Glu | Glu | Val | Glu | Glu | Val | Ile | Gly | Asn | Lys | Pro | Glu | Ser | Asp | Ile |
| | 1670 | | | | 1675 | | | | 1680 | |
| Leu | Val | His | Thr | Ala | Tyr | Asp | Glu | Ser | Thr | Asp | Glu | Asn | Val | Met |
| | 1685 | | | | 1690 | | | | 1695 | |
| Leu | Leu | Thr | Ser | Asp | Ala | Pro | Glu | Tyr | Lys | Pro | Trp | Ala | Leu | Val |
| | 1700 | | | | 1705 | | | | 1710 | |
| Ile | Gln | Asp | Ser | Asn | Gly | Glu | Asn | Lys | Ile | Lys | Met | Leu | Ser | Gly |
| | 1715 | | | | 1720 | | | | 1725 | |
| Gly | Ser | Pro | Lys | Lys | Lys | Arg | Lys | Val |
| | 1730 | | | | 1735 | |

<210> SEQ ID NO 12
<211> LENGTH: 5214
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding NLS-APOBEC1-XTEN-
      nCas9-UGI-NLS

<400> SEQUENCE: 12

| | |
|---|---|
| atgccaaaga agaaggaa ggtttcatcg agaccggcc ctgttgctgt tgacccacc | 60 |
| ctgcggcgga gaatcgagcc acacgagttc gaggtgttct tcgacccaag ggagctccgc | 120 |
| aaggagacgt gcctcctgta cgagatcaac tggggcggca gcactccat ctggaggcac | 180 |
| accagccaaa acaccaacaa gcacgtggag gtcaacttca tcgagaagtt caccaccgag | 240 |
| aggtacttct gccaaacac ccgctgctcc atcacctggt tcctgtcctg agcccatgc | 300 |
| ggcgagtgct ccagggccat caccgagttc ctcagccgct acccacacgt caccctgttc | 360 |
| atctacatcg ccaggctcta ccaccacgcc gacccaagga caggcaggg cctccgcgac | 420 |
| ctgatctcca gcggcgtgac catccaaatc atgaccgagc aggagtccgg ctactgctgg | 480 |
| aggaacttcg tcaactactc cccaagcaac gaggcccact ggccaaggta cccacacctc | 540 |
| tgggtgcgcc tctacgtgct cgagctgtac tgcatcatcc tcggcctgcc accatgcctc | 600 |
| aacatcctga ggcgcaagca accacagctg accttcttca ccatcgccct ccaaagctgc | 660 |
| cactaccaga ggctcccacc acacatcctg tgggctaccg gcctcaagtc cggcagcgag | 720 |
| acgccaggca cctccgagag cgctacgcct gaacttaagg acaagaagta ctcgatcggc | 780 |
| ctcgccatcg ggacgaactc agttggctgg gccgtgatca ccgacgagta caaggtgccc | 840 |

```
tctaagaagt tcaaggtcct ggggaacacc gaccgccatt ccatcaagaa gaacctcatc    900
ggcgctctcc tgttcgacag cggggagacc gctgaggcta cgaggctcaa gagaaccgct    960
aggcgccggt acacgagaag gaagaacagg atctgctacc tccaagagat tttctccaac   1020
gagatggcca aggttgacga ttcattcttc caccgcctgg aggagtcttt cctcgtggag   1080
gaggataaga agcacgagcg gcatcccatc ttcggcaaca tcgtggacga ggttgcctac   1140
cacgagaagt accctacgat ctaccatctg cggaagaagc tcgtggactc caccgataag   1200
gcggacctca gactgatcta cctcgctctg gcccacatga tcaagttccg cggccatttc   1260
ctgatcgagg gggatctcaa cccagacaac agcgatgttg acaagctgtt catccaactc   1320
gtgcagacct acaaccaact cttcgaggag aacccgatca cgcctctgg cgtggacgcg   1380 aaggctatcc tgtccgcgag gctctcgaag tccaggaggc tggagaacct gatcgctcag   1440
ctcccaggcg agaagaagaa cggcctgttc gggaacctca tcgctctcag cctggggctc   1500
accccgaact tcaagtcgaa cttcgatctc gctgaggacg ccaagctgca actctccaag   1560
gacacctacg acgatgacct cgataacctc ctggcccaga tcggcgatca atacgcggac   1620
ctgttcctcg ctgccaagaa cctgtcggac gccatcctcc tgtcagatat cctccgcgtg   1680
aacaccgaga tcacgaaggc tccactctct gcctccatga tcaagcgcta cgacgagcac   1740
catcaggatc tgaccctcct gaaggcgctg gtccgccaac agctcccgga agtacaag    1800 gagatttct tcgatcagtc gaagaacggc tacgctgggt acatcgacgg cggggcctca   1860
caagaggagt tctacaagtt catcaagcca atcctggaga gatggacgg cacggaggag   1920 ctcctggtga agctcaacag ggaggacctc ctgcggaagc agagaacctt cgataacggc   1980
agcatccccc accaaatcca tctcggggag ctgcacgcca tcctgagaag gcaagaggac   2040 ttctacccctt tcctcaagga taaccgggag aagatcgaga agatcctgac cttcagaatc   2100
ccatactacg tcggccctct cgcgcggggg aactcaagat tcgcttggat gacccgcaag   2160
tctgaggaga ccatcacgcc gtggaacttc gaggaggtgg tggacaaggg cgctagcgct   2220
cagtcgttca tcgagaggat gaccaacttc gacaagaacc tgcccaacga aaggtgctc   2280 cctaagcact cgctcctgta cgagtacttc accgtctaca cgagctcac gaaggtgaag   2340 tacgtcaccg agggcatgcg caagccagcg ttcctgtccg gggagcagaa gaaggctatc   2400
gtggacctcc tgttcaagac caaccggaag gtcacggtta gcaactcaa ggaggactac   2460 ttcaagaaga tcgagtgctt cgattcggtc gagatcagcg gcgttgagga ccgcttcaac   2520
gccagcctcg gaacctacca cgatctcctg aagatcatca aggataagga cttcctggac   2580
aacgaggaga acgaggatat cctggaggac atcgtgctga ccctcacgct gttcgaggac   2640
agggagatga tcgaggagcg cctgaagacg tacgcccatc tcttcgatga caaggtcatg   2700
aagcaactca gcgccggag atacaccggc tgggggaggc tgtcccgcaa gctcatcaac   2760
ggcatccggg acaagcagtc cggaagacc atcctcgact tcctcaagag cgatggcttc   2820
gccaacagga acttcatgca actgatccac gatgacagcc tcaccttcaa ggaggatatc   2880
caaaaggctc aagtgagcgg ccaggggac tcgctgcacg agcatatcgc gaacctcgct   2940
ggctcccccg cgatcaagaa gggcatcctc cagaccgtga aggttgtgga cgagctcgtg   3000
aaggtcatgg gccggcacaa gcctgagaac atcgtcatcg agatggccag agagaaccaa   3060
accacgcaga gggggcaaaa gaactctagg gagcgcatga gcgcatcga ggagggcatc   3120 aaggagctgg ggtcccaaat cctcaaggag cacccagtgg agaacaccca actgcagaac   3180
```

-continued

```
gagaagctct acctgtacta cctccagaac ggcagggata tgtacgtgga ccaagagctg   3240
gatatcaacc gcctcagcga ttacgacgtc gatcatatcg ttccccagtc tttcctgaag   3300
gatgactcca tcgacaacaa ggtcctcacc aggtcggaca agaaccgcgg caagtcagat   3360
aacgttccat ctgaggaggt cgttaagaag atgaagaact actggaggca gctcctgaac   3420
gccaagctga tcacgcaaag gaagttcgac aacctcacca aggctgagag aggcgggctc   3480
tcagagctgg acaaggccgg cttcatcaag cggcagctgg tcgagaccag acaaatcacg   3540
aagcacgttg cgcaaatcct cgactctcgg atgaacacga agtacgatga gaacgacaag   3600
ctgatcaggg aggttaaggt gatcaccctg aagtctaagc tcgtctccga cttcaggaag   3660
gatttccagt tctacaaggt tcgcgagatc aacaactacc accatgccca tgacgcttac   3720
ctcaacgctg tggtcggcac cgctctgatc aagaagtacc caaagctgga gtccgagttc   3780
gtgtacgggg actacaaggt ttacgatgtg cgcaagatga tcgccaagtc ggagcaagag   3840
atcggcaagg ctaccgccaa gtacttcttc tactcaaaca tcatgaactt cttcaagacc   3900
gagatcacgc tggccaacgg cgagatccgg aagagaccgc tcatcgagac caacggcgag   3960
acgggggaga tcgtgtggga caagggcagg gatttcgcga ccgtccgcaa ggttctctcc   4020
atgccccagg tgaacatcgt caagaagacc gaggtccaaa cgggcgggtt ctcaaaggag   4080
tctatcctgc ctaagcggaa cagcgacaag ctcatcgcca gaaagaagga ctgggaccca   4140
aagaagtacg gcgggttcga cagccctacc gtggcctact cggtcctggt tgtggcgaag   4200
gttgagaagg gcaagtccaa gaagctcaag agcgtgaagg agctcctggg gatcaccatc   4260
atggagaggt ccagcttcga gaagaaccca atcgacttcc tggaggccaa gggctacaag   4320
gaggtgaaga aggacctgat catcaagctc ccgaagtact ctctcttcga gctggagaac   4380
ggcaggaaga gaatgctggc ttccgctggc gagctccaga aggggaacga gctcgcgctg   4440
ccaagcaagt acgtgaactt cctctacctg gcttcccact acgagaagct caagggcagc   4500
ccggaggaca acgagcaaaa gcagctgttc gtcgagcagc acaagcatta cctcgacgag   4560
atcatcgagc aaatctccga gttcagcaag cgcgtgatcc tcgccgacgc gaacctggat   4620
aaggtcctct ccgcctacaa caagcaccgg acaagcccca tcagagagca gcggagaac   4680 atcatccatc tcttcacccct gacgaacctc ggcgctcctg ctgctttcaa gtacttcgac   4740
accacgatcg atcggaagag atacacctcc acgaaggagg tcctggacgc gaccctcatc   4800
caccagtcga tcaccggcct gtacgagacg aggatcgacc tctcacaact cggcggggat   4860
aagagacccg cagcaaccaa gaaggcaggg caagcaaaga agaagaagac gcgtgactcc   4920
ggcggcagca ccaacctgtc cgacatcatc gagaaggaga cgggcaagca actcgtgatc   4980
caggagagca tcctcatgct gccagaggag gtggaggagg tcatcggcaa caagccagag   5040
tccgacatcc tggtgcacac cgcctacgac gagtccaccg acgagaacgt catgctcctg   5100
accagcgacg cccagagta caagccatgg gccctcgtca tccaggacag caacggggag   5160
aacaagatca agatgctgtc ggggggagc ccaaagaaga gcggaaggt gtag          5214
```

<210> SEQ ID NO 13
<211> LENGTH: 5214
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotide sequence encoding NLS-APOBEC1-XTEN-dCas9-UGI-NLS

<400> SEQUENCE: 13

```
atgccaaaga agaagaggaa ggtttcatcg gagaccggcc ctgttgctgt tgaccccacc      60
ctgcggcgga gaatcgagcc acacgagttc gaggtgttct tcgacccaag ggagctccgc     120
aaggagacgt gcctcctgta cgagatcaac tggggcggca ggcactccat ctggaggcac     180
accagccaaa acaccaacaa gcacgtggag gtcaacttca tcgagaagtt caccaccgag     240
aggtacttct gcccaaacac ccgctgctcc atcacctggt tcctgtcctg agcccatgc      300
ggcgagtgct ccagggccat caccgagttc ctcagccgct acccacacgt caccctgttc     360
atctacatcg ccaggctcta ccaccacgcc gacccaagga acaggcaggg cctccgcgac     420
ctgatctcca gcggcgtgac catccaaatc atgaccgagc aggagtccgg ctactgctgg     480
aggaacttcg tcaactactc cccaagcaac gaggcccact ggccaaggta cccacacctc     540
tgggtgcgcc tctacgtgct cgagctgtac tgcatcatcc tcggcctgcc accatgcctc     600
aacatcctga ggcgcaagca accacagctg accttcttca ccatcgccct ccaaagctgc     660
cactaccaga ggctcccacc acacatcctg tgggctaccg gcctcaagtc cggcagcgag     720
acgccaggca cctccgagag cgctacgcct gaacttaagg acaagaagta ctcgatcggc     780
ctcgccatcg ggacgaactc agttggctgg gccgtgatca ccgacgagta caaggtgccc     840
tctaagaagt tcaaggtcct ggggaacacc gaccgccatt ccatcaagaa gaacctcatc     900
ggcgctctcc tgttcgacag cggggagacc gctgaggcta cgaggctcaa gagaaccgct     960
aggcgccggt acacgagaag gaagaacagg atctgctacc tccaagagat tttctccaac    1020
gagatggcca aggttgacga ttcattcttc caccgcctgg aggagtcttt cctcgtggag    1080
gaggataaga agcacgagcg gcatcccatc ttcggcaaca tcgtggacga ggttgcctac    1140
cacgagaagt accctacgat ctaccatctg cggaagaagc tcgtggactc caccgataag    1200
gcggacctca gactgatcta cctcgctctg gcccacatga tcaagttccg cggccatttc    1260
ctgatcgagg gggatctcaa cccagacaac agcgatgttg acaagctgtt catccaactc    1320
gtgcagacct acaaccaact cttcgaggag aacccgatca acgcctctgg cgtgacgcg     1380
aaggctatcc tgtccgcgag gctctcgaag tccaggaggc tggagaacct gatcgctcag    1440
ctcccaggcg agaagaagaa cggcctgttc gggaacctca tcgctctcag cctgggcctc    1500
accccgaact tcaagtcgaa cttcgatctc gctgaggacg ccaagctgca actctccaag    1560
gacacctacg acgatgacct cgataacctc ctggcccaga tcggcgatca atacgcggac    1620
ctgttcctcg ctgccaagaa cctgtcggac gccatcctcc tgtcagatat cctccgcgtg    1680
aacaccgaga tcacgaaggc tccactctct gcctccatga tcaagcgcta cgacgagcac    1740
catcaggatc tgaccctcct gaaggcgctg gtccgccaac agctcccgga agtacaag     1800
gagattttct tcgatcagtc gaagaacggc tacgctgggt acatcgacgg cggggcctca    1860
caagaggagt tctacaagtt catcaagcca atcctggaga gatggacgg cacggaggag     1920
ctcctggtga agctcaacag ggaggacctc ctgcggaagc agagaacctt cgataacggc    1980
agcatcccc accaaatcca tctcggggag ctgcacgcca tcctgagaag gcaagaggac    2040
ttctaccctt tcctcaagga taaccgggag aagatcgaga agatcctgac cttcagaatc    2100
ccatactacg tcggccctct cgcgcggggg aactcaagat tcgcttggat gacccgcaag    2160
tctgaggaga ccatcacgcc gtggaacttc gaggaggtgg tggacaaggg cgctagcgct    2220
cagtcgttca tcgagaggat gaccaacttc gacaagaacc tgcccaacga gaaggtgctc    2280
```

```
cctaagcact cgctcctgta cgagtacttc accgtctaca acgagctcac gaaggtgaag    2340
tacgtcaccg agggcatgcg caagccagcg ttcctgtccg gggagcagaa gaaggctatc    2400
gtggacctcc tgttcaagac caaccggaag gtcacggtta agcaactcaa ggaggactac    2460
ttcaagaaga tcgagtgctt cgattcggtc gagatcagcg gcgttgagga ccgcttcaac    2520
gccagcctcg ggacctacca cgatctcctg aagatcatca aggataagga cttcctggac    2580
aacgaggaga acgaggatat cctggaggac atcgtgctga ccctcacgct gttcgaggac    2640
agggagatga tcgaggagcg cctgaagacg tacgcccatc tcttcgatga caaggtcatg    2700
aagcaactca agcgccggag atacaccggc tgggggaggc tgtcccgcaa gctcatcaac    2760
ggcatccggg acaagcagtc cgggaagacc atcctcgact tcctcaagag cgatggcttc    2820
gccaacagga acttcatgca actgatccac gatgacagcc tcaccttcaa ggaggatatc    2880
caaaaggctc aagtgagcgg ccaggggggac tcgctgcacg agcatatcgc gaacctcgct    2940 ggctccccg cgatcaagaa gggcatcctc cagaccgtga aggttgtgga cgagctcgtg    3000
aaggtcatgg gccggcacaa gcctgagaac atcgtcatcg agatggccag agagaaccaa    3060
accacgcaga aggggcaaaa gaactctagg gagcgcatga gcgcatcga ggagggcatc    3120 aaggagctgg gtcccaaat cctcaaggag cacccagtgg agaacaccca actgcagaac    3180
gagaagctct acctgtacta cctccagaac ggcagggata tgtacgtgga ccaagagctg    3240
gatatcaacc gcctcagcga ttacgacgtc gatgctatcg ttccccagtc tttcctgaag    3300
gatgactcca tcgacaacaa ggtcctcacc aggtcggaca gaaccgcgg caagtcagat    3360 aacgttccat ctgaggaggt cgttaagaag atgaagaact actggaggca gctcctgaac    3420
gccaagctga tcacgcaaag gaagttcgac aacctcacca aggctgagag aggcgggctc    3480
tcagagctgg acaaggccgg cttcatcaag cggcagctgg tcgagaccag acaaatcacg    3540
aagcacgttg cgcaaatcct cgactctcgg atgaacacga agtacgatga aacgacaag    3600 ctgatcaggg aggttaaggt gatcaccctg aagtctaagc tcgtctccga cttcaggaag    3660
gatttccagt tctacaaggt tcgcgagatc aacaactacc accatgccca tgacgcttac    3720
ctcaacgctg tggtcggcac cgctctgatc aagaagtacc caaagctgga gtccgagttc    3780
gtgtacgggg actacaaggt ttacgatgtg cgcaagatga tcgccaagtc ggagcaagag    3840
atcggcaagc taccgccaa gtacttcttc tactcaaaca tcatgaactt cttcaagacc    3900
gagatcacgc tggccaacgg cgagatccgg aagagaccgc tcatcgagac caacggcgag    3960
acgggggaga tcgtgtggga caagggcagg gatttgcga ccgtccgcaa ggttctctcc    4020 atgcccagg tgaacatcgt caagaagacc gaggtccaaa cgggcgggtt ctcaaaggag    4080
tctatcctgc ctaagcggaa cagcgacaag ctcatcgcca gaaagaagga ctgggaccca    4140
aagaagtacg gcgggttcga cagccctacc gtggcctact cggtcctggt tgtggcgaag    4200
gttgagaagg gcaagtccaa gaagctcaag agcgtgaagg agctcctggg gatcaccatc    4260
atggagaggt ccagcttcga gaagaaccca atcgacttcc tggaggccaa gggctacaag    4320
gaggtgaaga aggacctgat catcaagctc ccgaagtact ctctcttcga gctggagaac    4380
ggcaggaaga gaatgctggc ttccgctggc gagctccaga gggggaacga gctcgcgctg    4440
ccaagcaagt acgtgaactt cctctacctg gcttcccact acgagaagct caagggcagc    4500
ccggaggaca acgagcaaaa gcagctgttc gtcgagcagc acaagcatta cctcgacgag    4560
atcatcgagc aaatctccga gttcagcaag cgcgtgatcc tcgccgacgc gaacctggat    4620
aaggtcctct ccgcctacaa caagcaccgg gacaagccca tcagagagca agcggagaac    4680
```

-continued

```
atcatccatc tcttcaccct gacgaacctc ggcgctcctg ctgctttcaa gtacttcgac    4740
accacgatcg atcggaagag atacacctcc acgaaggagg tcctggacgc gaccctcatc    4800
caccagtcga tcaccggcct gtacgagacg aggatcgacc tctcacaact cggcggggat    4860
aagagacccg cagcaaccaa gaaggcaggg caagcaaaga agaagaagac gcgtgactcc    4920
ggcggcagca ccaacctgtc cgacatcatc gagaaggaga cgggcaagca actcgtgatc    4980
caggagagca tcctcatgct gccagaggag gtggaggagg tcatcggcaa caagccagag    5040
tccgacatcc tggtgcacac cgcctacgac gagtccaccg acgagaacgt catgctcctg    5100
accagcgacg ccccagagta caagccatgg gccctcgtca tccaggacag caacggggag    5160
aacaagatca agatgctgtc gggggggagc ccaaagaaga agcggaaggt gtag           5214
```

<210> SEQ ID NO 14
<211> LENGTH: 2327
<212> TYPE: PRT
<213> ORGANISM: Oryza sativa

<400> SEQUENCE: 14

```
Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
```

```
             275                 280                 285
    Cys Leu Asp Ser Ile Pro Asp Glu Met Tyr Arg Lys Ala Cys Val Thr
    290                 295                 300
    Thr Thr Glu Glu Ala Val Ala Ser Cys Gln Val Val Gly Tyr Pro Ala
305                 310                 315                 320
    Met Ile Lys Ala Ser Trp Gly Gly Gly Lys Gly Ile Arg Lys Val
                    325                 330                 335
    His Asn Asp Asp Glu Val Arg Thr Leu Phe Lys Gln Val Gln Gly Glu
                340                 345                 350
    Val Pro Gly Ser Pro Ile Phe Ile Met Arg Leu Ala Ala Gln Ser Arg
                355                 360                 365
    His Leu Glu Val Gln Leu Leu Cys Asp Gln Tyr Gly Asn Val Ala Ala
    370                 375                 380
    Leu His Ser Arg Asp Cys Ser Val Gln Arg Arg His Gln Lys Ile Ile
385                 390                 395                 400
    Glu Glu Gly Pro Val Thr Val Ala Pro Arg Glu Thr Val Lys Glu Leu
                    405                 410                 415
    Glu Gln Ala Ala Arg Arg Leu Ala Lys Ala Val Gly Tyr Val Gly Ala
                420                 425                 430
    Ala Thr Val Glu Tyr Leu Tyr Ser Met Glu Thr Gly Glu Tyr Tyr Phe
                435                 440                 445
    Leu Glu Leu Asn Pro Arg Leu Gln Val Glu His Pro Val Thr Glu Trp
    450                 455                 460
    Ile Ala Glu Val Asn Leu Pro Ala Ala Gln Val Ala Val Gly Met Gly
465                 470                 475                 480
    Ile Pro Leu Trp Gln Ile Pro Glu Ile Arg Arg Phe Tyr Gly Met Asn
                    485                 490                 495
    His Gly Gly Gly Tyr Asp Leu Trp Arg Lys Thr Ala Ala Leu Ala Thr
                500                 505                 510
    Pro Phe Asn Phe Asp Glu Val Asp Ser Lys Trp Pro Lys Gly His Cys
                515                 520                 525
    Val Ala Val Arg Ile Thr Ser Glu Asp Pro Asp Gly Phe Lys Pro
    530                 535                 540
    Thr Gly Gly Lys Val Lys Glu Ile Ser Phe Lys Ser Lys Pro Asn Val
545                 550                 555                 560
    Trp Ala Tyr Phe Ser Val Lys Ser Gly Gly Gly Ile His Glu Phe Ala
                    565                 570                 575
    Asp Ser Gln Phe Gly His Val Phe Ala Tyr Gly Thr Thr Arg Ser Ala
                580                 585                 590
    Ala Ile Thr Thr Met Ala Leu Ala Leu Lys Glu Val Gln Ile Arg Gly
                595                 600                 605
    Glu Ile His Ser Asn Val Asp Tyr Thr Val Asp Leu Leu Asn Ala Ser
                610                 615                 620
    Asp Phe Arg Glu Asn Lys Ile His Thr Gly Trp Leu Asp Thr Arg Ile
    625                 630                 635                 640
    Ala Met Arg Val Gln Ala Glu Arg Pro Pro Trp Tyr Ile Ser Val Val
                    645                 650                 655
    Gly Gly Ala Leu Tyr Lys Thr Val Thr Ala Asn Thr Ala Thr Val Ser
                    660                 665                 670
    Asp Tyr Val Gly Tyr Leu Thr Lys Gly Gln Ile Pro Pro Lys His Ile
                675                 680                 685
    Ser Leu Val Tyr Thr Thr Val Ala Leu Asn Ile Asp Gly Lys Lys Tyr
                690                 695                 700
```

-continued

```
Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
            725                 730                 735

Leu Leu Met Gln Leu Asp Gly Asn Ser His Val Ile Tyr Ala Glu Glu
            740                 745                 750

Glu Ala Ser Gly Thr Arg Leu Leu Ile Asp Gly Lys Thr Cys Met Leu
            755                 760                 765

Gln Asn Asp His Asp Pro Ser Lys Leu Leu Ala Glu Thr Pro Cys Lys
            770                 775                 780

Leu Leu Arg Phe Leu Val Ala Asp Gly Ala His Val Ala Asp Val
785                 790                 795                 800

Pro Tyr Ala Glu Val Glu Val Met Lys Met Cys Met Pro Leu Leu Ser
                    805                 810                 815

Pro Ala Ser Gly Val Ile His Val Val Met Ser Glu Gly Gln Ala Met
            820                 825                 830

Gln Ala Gly Asp Leu Ile Ala Arg Leu Asp Leu Asp Asp Pro Ser Ala
            835                 840                 845

Val Lys Arg Ala Glu Pro Phe Glu Asp Thr Phe Pro Gln Met Gly Leu
850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
            885                 890                 895

Val Val Pro Glu Leu Val Tyr Cys Leu Asp Thr Pro Glu Leu Pro Phe
            900                 905                 910

Leu Gln Trp Glu Glu Leu Met Ser Val Leu Ala Thr Arg Leu Pro Arg
            915                 920                 925

Asn Leu Lys Ser Glu Leu Glu Gly Lys Tyr Glu Glu Tyr Lys Val Lys
            930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Lys Gly Lys Ala Thr
                965                 970                 975

Asn Glu Arg Leu Val Glu Pro Leu Met Ser Leu Leu Lys Ser Tyr Glu
            980                 985                 990

Gly Gly Arg Glu Ser His Ala His  Phe Val Val Lys Ser  Leu Phe Glu
            995                 1000                1005

Glu Tyr  Leu Tyr Val Glu Glu  Leu Phe Ser Asp Gly  Ile Gln Ser
    1010                1015                    1020

Asp Val  Ile Glu Arg Leu Arg  Leu Gln His Ser Lys  Asp Leu Gln
    1025                1030                    1035

Lys Val  Val Asp Ile Val Leu  Ser His Gln Ser Val  Arg Asn Lys
    1040                1045                    1050

Thr Lys  Leu Ile Leu Lys Leu  Met Glu Ser Leu Val  Tyr Pro Asn
    1055                1060                    1065

Pro Ala  Ala Tyr Arg Asp Gln  Leu Ile Arg Phe Ser  Ser Leu Asn
    1070                1075                    1080

His Lys  Ala Tyr Tyr Lys Leu  Ala Leu Lys Ala Ser  Glu Leu Leu
    1085                1090                    1095

Glu Gln  Thr Lys Leu Ser Glu  Leu Arg Ala Arg Ile  Ala Arg Ser
    1100                1105                    1110
```

```
Leu Ser Glu Leu Glu Met Phe Thr Glu Glu Ser Lys Gly Leu Ser
    1115                1120                1125

Met His Lys Arg Glu Ile Ala Ile Lys Glu Ser Met Glu Asp Leu
    1130                1135                1140

Val Thr Ala Pro Leu Pro Val Glu Asp Ala Leu Ile Ser Leu Phe
    1145                1150                1155

Asp Cys Ser Asp Thr Thr Val Gln Gln Arg Val Ile Glu Thr Tyr
    1160                1165                1170

Ile Ala Arg Leu Tyr Gln Pro His Leu Val Lys Asp Ser Ile Lys
    1175                1180                1185

Met Lys Trp Ile Glu Ser Gly Val Ile Ala Leu Trp Glu Phe Pro
    1190                1195                1200

Glu Gly His Phe Asp Ala Arg Asn Gly Gly Ala Val Leu Gly Asp
    1205                1210                1215

Lys Arg Trp Gly Ala Met Val Ile Val Lys Ser Leu Glu Ser Leu
    1220                1225                1230

Ser Met Ala Ile Arg Phe Ala Leu Lys Glu Thr Ser His Tyr Thr
    1235                1240                1245

Ser Ser Glu Gly Asn Met Met His Ile Ala Leu Leu Gly Ala Asp
    1250                1255                1260

Asn Lys Met His Ile Ile Gln Glu Ser Gly Asp Asp Ala Asp Arg
    1265                1270                1275

Ile Ala Lys Leu Pro Leu Ile Leu Lys Asp Asn Val Thr Asp Leu
    1280                1285                1290

His Ala Ser Gly Val Lys Thr Ile Ser Phe Ile Val Gln Arg Asp
    1295                1300                1305

Glu Ala Arg Met Thr Met Arg Arg Thr Phe Leu Trp Ser Asp Glu
    1310                1315                1320

Lys Leu Ser Tyr Glu Glu Glu Pro Ile Leu Arg His Val Glu Pro
    1325                1330                1335

Pro Leu Ser Ala Leu Leu Glu Leu Asp Lys Leu Lys Val Lys Gly
    1340                1345                1350

Tyr Asn Glu Met Lys Tyr Thr Pro Ser Arg Asp Arg Gln Trp His
    1355                1360                1365

Ile Tyr Thr Leu Arg Asn Thr Glu Asn Pro Lys Met Leu His Arg
    1370                1375                1380

Val Phe Phe Arg Thr Leu Val Arg Gln Pro Ser Val Ser Asn Lys
    1385                1390                1395

Phe Ser Ser Gly Gln Ile Gly Asp Met Glu Val Gly Ser Ala Glu
    1400                1405                1410

Glu Pro Leu Ser Phe Thr Ser Thr Ser Ile Leu Arg Ser Leu Met
    1415                1420                1425

Thr Ala Ile Glu Glu Leu Glu Leu His Ala Ile Arg Thr Gly His
    1430                1435                1440

Ser His Met Tyr Leu His Val Leu Lys Glu Gln Lys Leu Leu Asp
    1445                1450                1455

Leu Val Pro Val Ser Gly Asn Thr Val Leu Asp Val Gly Gln Asp
    1460                1465                1470

Glu Ala Thr Ala Tyr Ser Leu Leu Lys Glu Met Ala Met Lys Ile
    1475                1480                1485

His Glu Leu Val Gly Ala Arg Met His His Leu Ser Val Cys Gln
    1490                1495                1500

Trp Glu Val Lys Leu Lys Leu Asp Cys Asp Gly Pro Ala Ser Gly
```

-continued

```
            1505                1510                1515
Thr Trp Arg Ile Val Thr Thr Asn Val Thr Ser His Thr Cys Thr
    1520                1525                1530
Val Asp Ile Tyr Arg Glu Met Glu Asp Lys Glu Ser Arg Lys Leu
    1535                1540                1545
Val Tyr His Pro Ala Thr Pro Ala Ala Gly Pro Leu His Gly Val
    1550                1555                1560
Ala Leu Asn Asn Pro Tyr Gln Pro Leu Ser Val Ile Asp Leu Lys
    1565                1570                1575
Arg Cys Ser Ala Arg Asn Asn Arg Thr Thr Tyr Cys Tyr Asp Phe
    1580                1585                1590
Pro Leu Ala Phe Glu Thr Ala Val Arg Lys Ser Trp Ser Ser Ser
    1595                1600                1605
Thr Ser Gly Ala Ser Lys Gly Val Glu Asn Ala Gln Cys Tyr Val
    1610                1615                1620
Lys Ala Thr Glu Leu Val Phe Ala Asp Lys His Gly Ser Trp Gly
    1625                1630                1635
Thr Pro Leu Val Gln Met Asp Arg Pro Ala Gly Leu Asn Asp Ile
    1640                1645                1650
Gly Met Val Ala Trp Thr Leu Lys Met Ser Thr Pro Glu Phe Pro
    1655                1660                1665
Ser Gly Arg Glu Ile Ile Val Val Ala Asn Asp Ile Thr Phe Arg
    1670                1675                1680
Ala Gly Ser Phe Gly Pro Arg Glu Asp Ala Phe Phe Glu Ala Val
    1685                1690                1695
Thr Asn Leu Ala Cys Glu Lys Lys Leu Pro Leu Ile Tyr Leu Ala
    1700                1705                1710
Ala Asn Ser Gly Ala Arg Ile Gly Ile Ala Asp Glu Val Lys Ser
    1715                1720                1725
Cys Phe Arg Val Gly Trp Ser Asp Asp Gly Ser Pro Glu Arg Gly
    1730                1735                1740
Phe Gln Tyr Ile Tyr Leu Ser Glu Glu Asp Tyr Ala Arg Ile Gly
    1745                1750                1755
Thr Ser Val Ile Ala His Lys Met Gln Leu Asp Ser Gly Glu Ile
    1760                1765                1770
Arg Trp Val Ile Asp Ser Val Val Gly Lys Glu Asp Gly Leu Gly
    1775                1780                1785
Val Glu Asn Ile His Gly Ser Ala Ala Ile Ala Ser Ala Tyr Ser
    1790                1795                1800
Arg Ala Tyr Lys Glu Thr Phe Thr Leu Thr Phe Val Thr Gly Arg
    1805                1810                1815
Thr Val Gly Ile Gly Ala Tyr Leu Ala Arg Leu Gly Ile Arg Cys
    1820                1825                1830
Ile Gln Arg Leu Asp Gln Pro Ile Ile Leu Thr Gly Tyr Ser Ala
    1835                1840                1845
Leu Asn Lys Leu Leu Gly Arg Glu Val Tyr Ser Ser His Met Gln
    1850                1855                1860
Leu Gly Gly Pro Lys Ile Met Ala Thr Asn Gly Val Val His Leu
    1865                1870                1875
Thr Val Ser Asp Asp Leu Glu Gly Val Ser Asn Ile Leu Arg Trp
    1880                1885                1890
Leu Ser Tyr Val Pro Ala Tyr Ile Gly Gly Pro Leu Pro Val Thr
    1895                1900                1905
```

```
Thr Pro Leu Asp Pro Pro Asp Arg Pro Val Ala Tyr Ile Pro Glu
    1910            1915                1920

Asn Ser Cys Asp Pro Arg Ala Ala Ile Arg Gly Val Asp Asp Ser
    1925            1930                1935

Gln Gly Lys Trp Leu Gly Gly Met Phe Asp Lys Asp Ser Phe Val
    1940            1945                1950

Glu Thr Phe Glu Gly Trp Ala Lys Thr Val Thr Gly Arg Ala
    1955            1960                1965

Lys Leu Gly Gly Ile Pro Val Gly Val Ile Ala Val Glu Thr Gln
    1970            1975                1980

Thr Met Met Gln Thr Ile Pro Ala Asp Pro Gly Gln Leu Asp Ser
    1985            1990                1995

Arg Glu Gln Ser Val Pro Arg Ala Gly Gln Val Trp Phe Pro Asp
    2000            2005                2010

Ser Ala Thr Lys Thr Ala Gln Ala Leu Leu Asp Phe Asn Arg Glu
    2015            2020                2025

Gly Leu Pro Leu Phe Ile Leu Ala Asn Trp Arg Gly Phe Ser Gly
    2030            2035                2040

Gly Gln Arg Asp Leu Phe Glu Gly Ile Leu Gln Ala Gly Ser Thr
    2045            2050                2055

Ile Val Glu Asn Leu Arg Thr Tyr Asn Gln Pro Ala Phe Val Tyr
    2060            2065                2070

Ile Pro Met Ala Ala Glu Leu Arg Gly Gly Ala Trp Val Val Val
    2075            2080                2085

Asp Ser Lys Ile Asn Pro Asp Arg Ile Glu Cys Tyr Ala Glu Arg
    2090            2095                2100

Thr Ala Lys Gly Asn Val Leu Glu Pro Gln Gly Leu Ile Glu Ile
    2105            2110                2115

Lys Phe Arg Ser Glu Glu Leu Gln Asp Cys Met Ser Arg Leu Asp
    2120            2125                2130

Pro Thr Leu Ile Asp Leu Lys Ala Lys Leu Glu Val Ala Asn Lys
    2135            2140                2145

Asn Gly Ser Ala Asp Thr Lys Ser Leu Gln Glu Asn Ile Glu Ala
    2150            2155                2160

Arg Thr Lys Gln Leu Met Pro Leu Tyr Thr Gln Ile Ala Ile Arg
    2165            2170                2175

Phe Ala Glu Leu His Asp Thr Ser Leu Arg Met Ala Ala Lys Gly
    2180            2185                2190

Val Ile Lys Lys Val Val Asp Trp Glu Glu Ser Arg Ser Phe Phe
    2195            2200                2205

Tyr Lys Arg Leu Arg Arg Arg Ile Ser Glu Asp Val Leu Ala Lys
    2210            2215                2220

Glu Ile Arg Ala Val Ala Gly Glu Gln Phe Ser His Gln Pro Ala
    2225            2230                2235

Ile Glu Leu Ile Lys Lys Trp Tyr Ser Ala Ser His Ala Ala Glu
    2240            2245                2250

Trp Asp Asp Asp Ala Phe Val Ala Trp Met Asp Asn Pro Glu
    2255            2260                2265

Asn Tyr Lys Asp Tyr Ile Gln Tyr Leu Lys Ala Gln Arg Val Ser
    2270            2275                2280

Gln Ser Leu Ser Ser Leu Ser Asp Ser Ser Asp Leu Gln Ala
    2285            2290                2295
```

```
Leu Pro Gln Gly Leu Ser Met Leu Leu Asp Lys Met Asp Pro Ser
    2300                2305                2310

Arg Arg Ala Gln Leu Val Glu Glu Ile Arg Lys Val Leu Gly
    2315                2320                2325
```

<210> SEQ ID NO 15
<211> LENGTH: 2311
<212> TYPE: PRT
<213> ORGANISM: Triticum aestivum

<400> SEQUENCE: 15

```
Met Gly Ser Thr His Leu Pro Ile Val Gly Phe Asn Ala Ser Thr Thr
1               5                   10                  15

Pro Ser Leu Ser Thr Ile Arg Pro Val Asn Ser Ala Gly Ala Ala Phe
                20                  25                  30

Gln Pro Ser Ala Pro Ser Arg Thr Ser Lys Lys Ser Arg Arg Val
            35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Val Ala Leu Gly Gly
        115                 120                 125

Lys Thr Pro Ile His Ser Val Leu Val Ala Asn Asn Gly Met Ala Ala
130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Pro Trp Ser Gly Ser Gln Val Glu Ile Pro Leu Glu Val Cys Leu Asp
        275                 280                 285

Ser Ile Pro Ala Glu Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350
```

```
Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Glu Leu Glu Gln Ala
                    405                 410                 415

Ala Arg Arg Leu Ala Lys Ala Val Gly Tyr Val Gly Ala Ala Thr Val
                420                 425                 430

Glu Tyr Leu Tyr Ser Met Glu Thr Gly Glu Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
                485                 490                 495

Gly Tyr Asp Ile Trp Arg Lys Thr Ala Ala Leu Ala Thr Pro Phe Asn
                500                 505                 510

Phe Asp Glu Val Asp Ser Gln Trp Pro Lys Gly His Cys Val Ala Val
                515                 520                 525

Arg Ile Thr Ser Glu Asp Pro Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                565                 570                 575

Phe Gly His Val Phe Ala Tyr Gly Val Ser Arg Ala Ala Ala Ile Thr
                580                 585                 590

Asn Met Ser Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Lys
    610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Ile Thr Ser Asn Thr Asp Thr Val Ser Glu Tyr Val
                660                 665                 670

Ser Tyr Leu Val Lys Gly Gln Ile Pro Pro Lys His Ile Ser Leu Val
        675                 680                 685

His Ser Thr Val Ser Leu Asn Ile Glu Glu Ser Lys Tyr Thr Ile Glu
    690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
                725                 730                 735

Gln Leu Asp Gly Asn Ser His Val Ile Tyr Ala Glu Glu Ala Gly
                740                 745                 750

Gly Thr Arg Leu Leu Ile Asp Gly Lys Thr Cys Leu Leu Gln Asn Asp
        755                 760                 765
```

```
His Asp Pro Ser Arg Leu Leu Ala Glu Thr Pro Cys Lys Leu Leu Arg
    770             775             780

Phe Leu Val Ala Asp Gly Ala His Val Glu Ala Asp Val Pro Tyr Ala
785             790             795                 800

Glu Val Glu Val Met Lys Met Cys Met Pro Leu Leu Ser Pro Ala Ala
                805             810             815

Gly Val Ile Asn Val Leu Leu Ser Glu Gly Gln Pro Met Gln Ala Gly
            820             825             830

Asp Leu Ile Ala Arg Leu Asp Leu Asp Pro Ser Ala Val Lys Arg
        835             840             845

Ala Glu Pro Phe Asn Gly Ser Phe Pro Glu Met Ser Leu Pro Ile Ala
850             855             860

Ala Ser Gly Gln Val His Lys Arg Cys Ala Thr Ser Leu Asn Ala Ala
865             870             875             880

Arg Met Val Leu Ala Gly Tyr Asp His Pro Ile Asn Lys Val Val Gln
                885             890             895

Asp Leu Val Ser Cys Leu Asp Ala Pro Glu Leu Pro Phe Leu Gln Trp
        900             905             910

Glu Glu Leu Met Ser Val Leu Ala Thr Arg Leu Pro Arg Leu Leu Lys
        915             920             925

Ser Glu Leu Glu Gly Lys Tyr Ser Glu Tyr Lys Leu Asn Val Gly His
    930             935             940

Gly Lys Ser Lys Asp Phe Pro Ser Lys Met Leu Arg Glu Ile Ile Glu
945             950             955             960

Glu Asn Leu Ala His Gly Ser Glu Lys Glu Ile Ala Thr Asn Glu Arg
            965             970             975

Leu Val Glu Pro Leu Met Ser Leu Leu Lys Ser Tyr Glu Gly Gly Arg
            980             985             990

Glu Ser His Ala His Phe Ile Val  Lys Ser Leu Phe Glu  Asp Tyr Leu
        995             1000            1005

Ser Val  Glu Glu Leu Phe Ser  Asp Gly Ile Gln Ser  Asp Val Ile
    1010            1015            1020

Glu Arg  Leu Arg Gln Gln His  Ser Lys Asp Leu Gln  Lys Val Val
    1025            1030            1035

Asp Ile  Val Leu Ser His Gln  Gly Val Arg Asn Lys  Thr Lys Leu
    1040            1045            1050

Ile Leu  Thr Leu Met Glu Lys  Leu Val Tyr Pro Asn  Pro Ala Ala
    1055            1060            1065

Tyr Lys  Asp Gln Leu Thr Arg  Phe Ser Ser Leu Asn  His Lys Arg
    1070            1075            1080

Tyr Tyr  Lys Leu Ala Leu Lys  Ala Ser Glu Leu Leu  Glu Gln Thr
    1085            1090            1095

Lys Leu  Ser Glu Leu Arg Thr  Ser Ile Ala Arg Ser  Leu Ser Glu
    1100            1105            1110

Leu Glu  Met Phe Thr Glu Glu  Arg Thr Ala Ile Ser  Glu Ile Met
    1115            1120            1125

Gly Asp  Leu Val Thr Ala Pro  Leu Pro Val Glu Asp  Ala Leu Val
    1130            1135            1140

Ser Leu  Phe Asp Cys Ser Asp  Gln Thr Leu Gln Gln  Arg Val Ile
    1145            1150            1155

Glu Thr  Tyr Ile Ser Arg Leu  Tyr Gln Pro His Leu  Val Lys Asp
    1160            1165            1170

Ser Ile  Gln Leu Lys Tyr Gln  Glu Ser Gly Val Ile  Ala Leu Trp
```

```
            1175                1180                1185

Glu Phe Ala Glu Ala His Ser Glu Lys Arg Leu Gly Ala Met Val
        1190                1195                1200

Ile Val Lys Ser Leu Glu Ser Val Ser Ala Ala Ile Gly Ala Ala
        1205                1210                1215

Leu Lys Asp Thr Ser Arg Tyr Ala Ser Ser Glu Gly Asn Ile Met
        1220                1225                1230

His Ile Ala Leu Leu Gly Ala Asp Asn Gln Met His Gly Thr Glu
        1235                1240                1245

Asp Ser Gly Asp Asn Asp Gln Ala Gln Val Arg Ile Asp Lys Leu
        1250                1255                1260

Ser Ala Thr Leu Glu Gln Asn Thr Val Thr Ala Asp Leu Arg Ala
        1265                1270                1275

Ala Gly Val Lys Val Ile Ser Cys Ile Val Gln Arg Asp Gly Ala
        1280                1285                1290

Leu Met Pro Met Arg His Thr Phe Leu Leu Ser Asp Glu Lys Leu
        1295                1300                1305

Cys Tyr Glu Glu Glu Pro Val Leu Arg His Val Glu Pro Pro Leu
        1310                1315                1320

Ser Ala Leu Leu Glu Leu Gly Lys Leu Lys Val Lys Gly Tyr Asn
        1325                1330                1335

Glu Val Lys Tyr Thr Pro Ser Arg Asp Arg Gln Trp Asn Ile Tyr
        1340                1345                1350

Thr Leu Arg Asn Thr Glu Asn Pro Lys Met Leu His Arg Val Phe
        1355                1360                1365

Phe Arg Thr Leu Val Arg Gln Pro Gly Ala Ser Asn Lys Phe Thr
        1370                1375                1380

Ser Gly His Ile Ser Asp Val Glu Val Gly Gly Ala Glu Glu Ser
        1385                1390                1395

Leu Ser Phe Thr Ser Ser Ser Ile Leu Arg Ser Leu Met Thr Ala
        1400                1405                1410

Ile Glu Glu Leu Glu Leu His Ala Ile Arg Thr Gly His Ser His
        1415                1420                1425

Met Phe Leu Cys Ile Leu Lys Glu Gln Lys Leu Leu Asp Leu Val
        1430                1435                1440

Pro Val Ser Gly Asn Thr Val Val Asp Ile Gly Gln Asp Glu Ala
        1445                1450                1455

Thr Ala Cys Ser Leu Leu Lys Glu Met Ala Leu Gln Ile His Glu
        1460                1465                1470

Leu Val Gly Ala Arg Met His His Leu Ser Val Cys Gln Trp Glu
        1475                1480                1485

Val Lys Leu Lys Leu Asp Ser Asp Gly Pro Ala Ser Gly Thr Trp
        1490                1495                1500

Arg Val Val Thr Thr Asn Val Thr Ser His Thr Cys Thr Val Asp
        1505                1510                1515

Ile Tyr Arg Glu Val Glu Asp Thr Glu Ser Gln Lys Leu Val Tyr
        1520                1525                1530

His Ser Ala Pro Ser Ser Ser Gly Pro Leu His Gly Val Ala Leu
        1535                1540                1545

Asn Thr Pro Tyr Gln Pro Leu Ser Val Ile Asp Leu Lys Arg Cys
        1550                1555                1560

Ser Ala Arg Asn Asn Arg Thr Thr Tyr Cys Tyr Asp Phe Pro Leu
        1565                1570                1575
```

-continued

```
Ala Phe Glu Thr Ala Val Gln Lys Ser Trp Ser Asn Ile Ser Ser
    1580                1585                1590

Asp Asn Asn Arg Cys Tyr Val Lys Ala Thr Glu Leu Val Phe Ala
    1595                1600                1605

His Lys Asn Gly Ser Trp Gly Thr Pro Val Ile Pro Met Glu Arg
    1610                1615                1620

Pro Ala Gly Leu Asn Asp Ile Gly Met Val Ala Trp Ile Leu Asp
    1625                1630                1635

Met Ser Thr Pro Glu Tyr Pro Asn Gly Arg Gln Ile Val Val Ile
    1640                1645                1650

Ala Asn Asp Ile Thr Phe Arg Ala Gly Ser Phe Gly Pro Arg Glu
    1655                1660                1665

Asp Ala Phe Phe Glu Thr Val Thr Asn Leu Ala Cys Glu Arg Lys
    1670                1675                1680

Leu Pro Leu Ile Tyr Leu Ala Ala Asn Ser Gly Ala Arg Ile Gly
    1685                1690                1695

Ile Ala Asp Glu Val Lys Ser Cys Phe Arg Val Gly Trp Ser Asp
    1700                1705                1710

Asp Gly Ser Pro Glu Arg Gly Phe Gln Tyr Ile Tyr Leu Thr Glu
    1715                1720                1725

Glu Asp His Ala Arg Ile Ser Thr Ser Val Ile Ala His Lys Met
    1730                1735                1740

Gln Leu Asp Asn Gly Glu Ile Arg Trp Val Ile Asp Ser Val Val
    1745                1750                1755

Gly Lys Glu Asp Gly Leu Gly Val Glu Asn Ile His Gly Ser Ala
    1760                1765                1770

Ala Ile Ala Ser Ala Tyr Ser Arg Ala Tyr Glu Glu Thr Phe Thr
    1775                1780                1785

Leu Thr Phe Val Thr Gly Arg Thr Val Gly Ile Gly Ala Tyr Leu
    1790                1795                1800

Ala Arg Leu Gly Ile Arg Cys Ile Gln Arg Thr Asp Gln Pro Ile
    1805                1810                1815

Ile Leu Thr Gly Phe Ser Ala Leu Asn Lys Leu Leu Gly Arg Glu
    1820                1825                1830

Val Tyr Ser Ser His Met Gln Leu Gly Gly Pro Lys Ile Met Ala
    1835                1840                1845

Thr Asn Gly Val Val His Leu Thr Val Ser Asp Asp Leu Glu Gly
    1850                1855                1860

Val Ser Asn Ile Leu Arg Trp Leu Ser Tyr Val Pro Ala Asn Ile
    1865                1870                1875

Gly Gly Pro Leu Pro Ile Thr Lys Ser Leu Asp Pro Pro Asp Arg
    1880                1885                1890

Pro Val Ala Tyr Ile Pro Glu Asn Thr Cys Asp Pro Arg Ala Ala
    1895                1900                1905

Ile Ser Gly Ile Asp Asp Ser Gln Gly Lys Trp Leu Gly Gly Met
    1910                1915                1920

Phe Asp Lys Asp Ser Phe Val Glu Thr Phe Glu Gly Trp Ala Lys
    1925                1930                1935

Ser Val Val Thr Gly Arg Ala Lys Leu Gly Gly Ile Pro Val Gly
    1940                1945                1950

Val Ile Ala Val Glu Thr Gln Thr Met Met Gln Leu Ile Pro Ala
    1955                1960                1965
```

Asp Pro Gly Gln Leu Asp Ser His Glu Arg Ser Val Pro Arg Ala
       1970                1975                1980

Gly Gln Val Trp Phe Pro Asp Ser Ala Thr Lys Thr Ala Gln Ala
       1985                1990                1995

Met Leu Asp Phe Asn Arg Glu Gly Leu Pro Leu Phe Ile Leu Ala
       2000                2005                2010

Asn Trp Arg Gly Phe Ser Gly Gly Gln Arg Asp Leu Phe Glu Gly
       2015                2020                2025

Ile Leu Gln Ala Gly Ser Thr Ile Val Glu Asn Leu Arg Thr Tyr
       2030                2035                2040

Asn Gln Pro Ala Phe Val Tyr Ile Pro Lys Ala Ala Glu Leu Arg
       2045                2050                2055

Gly Gly Ala Trp Val Val Ile Asp Ser Lys Ile Asn Pro Asp Arg
       2060                2065                2070

Ile Glu Phe Tyr Ala Glu Arg Thr Ala Lys Gly Asn Val Leu Glu
       2075                2080                2085

Pro Gln Gly Leu Ile Glu Ile Lys Phe Arg Ser Glu Glu Leu Gln
       2090                2095                2100

Glu Cys Met Gly Arg Leu Asp Pro Glu Leu Ile Asn Leu Lys Ala
       2105                2110                2115

Lys Leu Gln Gly Val Lys His Glu Asn Gly Ser Leu Pro Glu Ser
       2120                2125                2130

Glu Ser Leu Gln Lys Ser Ile Glu Ala Arg Lys Lys Gln Leu Leu
       2135                2140                2145

Pro Leu Tyr Thr Gln Ile Ala Val Arg Phe Ala Glu Leu His Asp
       2150                2155                2160

Thr Ser Leu Arg Met Ala Ala Lys Gly Val Ile Lys Lys Val Val
       2165                2170                2175

Asp Trp Glu Asp Ser Arg Ser Phe Phe Tyr Lys Arg Leu Arg Arg
       2180                2185                2190

Arg Ile Ser Glu Asp Val Leu Ala Lys Glu Ile Arg Gly Val Ser
       2195                2200                2205

Gly Lys Gln Phe Ser His Gln Ser Ala Ile Glu Leu Ile Gln Lys
       2210                2215                2220

Trp Tyr Leu Ala Ser Lys Gly Ala Glu Thr Gly Ser Thr Glu Trp
       2225                2230                2235

Asp Asp Asp Ala Phe Val Ala Trp Arg Glu Asn Pro Glu Asn
       2240                2245                2250

Tyr Gln Glu Tyr Ile Lys Glu Leu Arg Ala Gln Arg Val Ser Gln
       2255                2260                2265

Leu Leu Ser Asp Val Ala Asp Ser Ser Pro Asp Leu Glu Ala Leu
       2270                2275                2280

Pro Gln Gly Leu Ser Met Leu Leu Glu Lys Met Asp Pro Ser Arg
       2285                2290                2295

Arg Ala Gln Phe Val Glu Glu Val Lys Lys Val Leu Lys
       2300                2305                2310

<210> SEQ ID NO 16
<211> LENGTH: 644
<212> TYPE: PRT
<213> ORGANISM: Oryza sativa

<400> SEQUENCE: 16

Met Ala Thr Thr Ala Ala Ala Ala Ala Ala Thr Leu Ser Ala Ala Ala
1               5                   10                  15

```
Thr Ala Lys Thr Gly Arg Lys Asn His Gln Arg His His Val Leu Pro
             20                  25                  30

Ala Arg Gly Arg Val Gly Ala Ala Val Arg Cys Ser Ala Val Ser
         35                  40                  45

Pro Val Thr Pro Pro Ser Pro Ala Pro Pro Ala Thr Pro Leu Arg Pro
 50                  55                  60

Trp Gly Pro Ala Glu Pro Arg Lys Gly Ala Asp Ile Leu Val Glu Ala
 65                  70                  75                  80

Leu Glu Arg Cys Gly Val Ser Asp Val Phe Ala Tyr Pro Gly Gly Ala
             85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
             115                 120                 125

Ala Arg Ala Ser Gly Arg Val Gly Val Cys Val Ala Thr Ser Gly Pro
 130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
             165                 170                 175

Thr Asp Ala Phe Gln Glu Thr Pro Ile Val Glu Val Thr Arg Ser Ile
             180                 185                 190

Thr Lys His Asn Tyr Leu Val Leu Asp Val Glu Asp Ile Pro Arg Val
             195                 200                 205

Ile Gln Glu Ala Phe Phe Leu Ala Ser Ser Gly Arg Pro Gly Pro Val
 210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
             245                 250                 255

Pro Pro Ala Thr Glu Leu Leu Glu Gln Val Leu Arg Leu Val Gly Glu
             260                 265                 270

Ser Arg Arg Pro Ile Leu Tyr Val Gly Gly Gly Cys Ser Ala Ser Gly
     275                 280                 285

Asp Glu Leu Arg Arg Phe Val Glu Leu Thr Gly Ile Pro Val Thr Thr
 290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
             325                 330                 335

Lys Ala Asp Leu Leu Leu Ala Phe Gly Val Arg Phe Asp Asp Arg Val
         340                 345                 350

Thr Gly Lys Ile Glu Ala Phe Ala Ser Arg Ala Lys Ile Val His Ile
         355                 360                 365

Asp Ile Asp Pro Ala Glu Ile Gly Lys Asn Lys Gln Pro His Val Ser
 370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
             405                 410                 415

Glu Leu Asp Gln Gln Lys Arg Glu Phe Pro Leu Gly Tyr Lys Thr Phe
             420                 425                 430
```

-continued

```
Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
610                 615                 620

Ile Pro Ser Glu Gly Ala Phe Lys Asp Met Ile Leu Asp Gly Asp Gly
625                 630                 635                 640

Arg Thr Met Tyr

<210> SEQ ID NO 17
<211> LENGTH: 598
<212> TYPE: PRT
<213> ORGANISM: Triticum aestivum

<400> SEQUENCE: 17

Ala Ala Ser Pro Ala Ala Thr Ser Ala Ala Pro Pro Ala Thr Ala Leu
1               5                   10                  15

Arg Pro Trp Gly Pro Ser Glu Pro Arg Lys Gly Ala Asp Ile Leu Val
            20                  25                  30

Glu Ala Leu Glu Arg Cys Gly Ile Val Asp Val Phe Ala Tyr Pro Gly
        35                  40                  45

Gly Ala Ser Met Glu Ile His Gln Ala Leu Thr Arg Ser Pro Val Ile
    50                  55                  60

Thr Asn His Leu Phe Arg His Glu Gln Gly Glu Ala Phe Ala Ala Ser
65                  70                  75                  80

Gly Tyr Ala Arg Ala Ser Gly Arg Val Gly Val Cys Val Ala Thr Ser
                85                  90                  95

Gly Pro Gly Ala Thr Asn Leu Val Ser Ala Leu Ala Asp Ala Leu Leu
            100                 105                 110

Asp Ser Ile Pro Met Val Ala Ile Thr Gly Gln Val Pro Arg Arg Met
        115                 120                 125

Ile Gly Thr Asp Ala Phe Gln Glu Thr Pro Ile Val Glu Val Thr Arg
    130                 135                 140

Ser Ile Thr Lys His Asn Tyr Leu Val Leu Asp Val Glu Asp Ile Pro
145                 150                 155                 160
```

-continued

Arg Val Ile Gln Glu Ala Phe Phe Leu Ala Ser Ser Gly Arg Pro Gly
            165                 170                 175

Pro Val Leu Val Asp Ile Pro Lys Asp Ile Gln Gln Met Ala Val
        180                 185                 190

Pro Val Trp Asp Thr Pro Met Ser Leu Pro Gly Tyr Ile Ala Arg Leu
        195                 200                 205

Pro Lys Pro Pro Ser Thr Glu Ser Leu Glu Gln Val Leu Arg Leu Val
210                 215                 220

Gly Glu Ser Arg Arg Pro Ile Leu Tyr Val Gly Gly Cys Ala Ala
225                 230                 235                 240

Ser Gly Glu Glu Leu Arg Arg Phe Val Glu Leu Thr Gly Ile Pro Val
            245                 250                 255

Thr Thr Thr Leu Met Gly Leu Gly Asn Phe Pro Ser Asp Asp Pro Leu
            260                 265                 270

Ser Leu Arg Met Leu Gly Met His Gly Thr Val Tyr Ala Asn Tyr Ala
            275                 280                 285

Val Asp Lys Ala Asp Leu Leu Leu Ala Phe Gly Val Arg Phe Asp Asp
        290                 295                 300

Arg Val Thr Gly Lys Ile Glu Ala Phe Ala Ser Arg Ser Lys Ile Val
305                 310                 315                 320

His Ile Asp Ile Asp Pro Ala Glu Ile Gly Lys Asn Lys Gln Pro His
                325                 330                 335

Val Ser Ile Cys Ala Asp Val Lys Leu Ala Leu Gln Gly Leu Asn Asp
            340                 345                 350

Leu Leu Asn Gly Ser Lys Ala Gln Gln Gly Leu Asp Phe Gly Pro Trp
            355                 360                 365

His Lys Glu Leu Asp Gln Gln Lys Arg Glu Phe Pro Leu Gly Phe Lys
        370                 375                 380

Thr Phe Gly Glu Ala Ile Pro Pro Gln Tyr Ala Ile Gln Val Leu Asp
385                 390                 395                 400

Glu Leu Thr Lys Gly Glu Ala Ile Ile Ala Thr Gly Val Gly Gln His
            405                 410                 415

Gln Met Trp Ala Ala Gln Tyr Tyr Thr Tyr Lys Arg Pro Arg Gln Trp
            420                 425                 430

Leu Ser Ser Ser Gly Leu Gly Ala Met Gly Phe Gly Leu Pro Ala Ala
        435                 440                 445

Ala Gly Ala Ala Val Ala Asn Pro Gly Val Thr Val Val Asp Ile Asp
        450                 455                 460

Gly Asp Gly Ser Phe Leu Met Asn Ile Gln Glu Leu Ala Leu Ile Arg
465                 470                 475                 480

Ile Glu Asn Leu Pro Val Lys Val Met Ile Leu Asn Asn Gln His Leu
                485                 490                 495

Gly Met Val Val Gln Trp Glu Asp Arg Phe Tyr Lys Ala Asn Arg Ala
            500                 505                 510

His Thr Tyr Leu Gly Asn Pro Glu Asn Glu Ser Glu Ile Tyr Pro Asp
        515                 520                 525

Phe Val Thr Ile Ala Lys Gly Phe Asn Val Pro Ala Val Arg Val Thr
530                 535                 540

Lys Lys Ser Glu Val Thr Ala Ala Ile Lys Lys Met Leu Glu Thr Pro
545                 550                 555                 560

Gly Pro Tyr Leu Leu Asp Ile Ile Val Pro His Gln Glu His Val Leu
                565                 570                 575

Pro Met Ile Pro Ser Gly Gly Ala Phe Lys Asp Met Ile Met Glu Gly

```
                580                 585                 590
Asp Gly Arg Thr Ser Tyr
        595

<210> SEQ ID NO 18
<211> LENGTH: 436
<212> TYPE: PRT
<213> ORGANISM: Triticum aestivum

<400> SEQUENCE: 18

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Met Val Arg Phe
            20                  25                  30

Asn Pro Arg Ser Asp Arg Phe His Thr Leu Ser Phe His His Val Glu
            35                  40                  45

Phe Trp Cys Ala Asp Ala Ala Ser Ala Ala Gly Arg Phe Ala Phe Ala
        50                  55                  60

Leu Gly Ala Pro Leu Ala Ala Arg Ser Asp Leu Ser Thr Gly Asn Ser
65                  70                  75                  80

Val His Ala Ser Gln Leu Leu Arg Ser Gly Asn Leu Ala Phe Leu Phe
                85                  90                  95

Thr Ala Pro Tyr Ala Asn Gly Cys Asp Ala Ala Thr Ala Ser Leu Pro
            100                 105                 110

Ser Phe Ser Ala Asp Ala Ala Arg Arg Phe Ser Ala Asp His Gly Leu
        115                 120                 125

Ala Val Arg Ser Ile Ala Leu Arg Val Ala Asp Ala Ala Glu Ala Phe
    130                 135                 140

Arg Ala Ser Val Asp Gly Gly Ala Arg Pro Ala Phe Ser Pro Val Asp
145                 150                 155                 160

Leu Gly Arg Gly Phe Gly Phe Ala Glu Val Glu Leu Tyr Gly Asp Val
                165                 170                 175

Val Leu Arg Phe Val Ser His Pro Asp Asp Thr Asp Val Pro Phe Leu
            180                 185                 190

Pro Gly Phe Glu Gly Val Ser Asn Pro Asp Ala Val Asp Tyr Gly Leu
        195                 200                 205

Thr Arg Phe Asp His Val Val Gly Asn Val Pro Glu Leu Ala Pro Ala
    210                 215                 220

Ala Ala Tyr Val Ala Gly Phe Ala Gly Phe His Glu Phe Ala Glu Phe
225                 230                 235                 240

Thr Thr Glu Asp Val Gly Thr Ala Glu Ser Gly Leu Asn Ser Met Val
                245                 250                 255

Leu Ala Asn Asn Ser Glu Gly Val Leu Leu Pro Leu Asn Glu Pro Val
            260                 265                 270

His Gly Thr Lys Arg Arg Ser Gln Ile Gln Thr Phe Leu Glu His His
        275                 280                 285

Gly Gly Ser Gly Val Gln His Ile Ala Val Ala Ser Ser Asp Val Leu
    290                 295                 300

Arg Thr Leu Arg Glu Met Arg Ala Arg Ser Ala Met Gly Gly Phe Asp
305                 310                 315                 320

Phe Leu Pro Pro Arg Cys Arg Lys Tyr Tyr Glu Gly Val Arg Arg Ile
                325                 330                 335

Ala Gly Asp Val Leu Ser Glu Ala Gln Ile Lys Glu Cys Gln Glu Leu
            340                 345                 350
```

-continued

Gly Val Leu Val Asp Arg Asp Gln Gly Val Leu Leu Gln Ile Phe
            355                 360                 365

Thr Lys Pro Val Gly Asp Arg Pro Thr Leu Phe Leu Glu Met Ile Gln
370                 375                 380

Arg Ile Gly Cys Met Glu Lys Asp Glu Arg Gly Glu Glu Tyr Gln Lys
385                 390                 395                 400

Gly Gly Cys Gly Gly Phe Gly Lys Gly Asn Phe Ser Glu Leu Phe Lys
                405                 410                 415

Ser Ile Glu Asp Tyr Glu Lys Ser Leu Glu Ala Lys Gln Ser Ala Ala
            420                 425                 430

Val Gln Gly Ser
    435

<210> SEQ ID NO 19
<211> LENGTH: 23
<212> TYPE: DNA
<213> ORGANISM: Oryza sativa
<220> FEATURE:
<223> OTHER INFORMATION: R1

<400> SEQUENCE: 19
cctacccggg cggcgcgtcc atg                                           23

<210> SEQ ID NO 20
<211> LENGTH: 23
<212> TYPE: DNA
<213> ORGANISM: Oryza sativa
<220> FEATURE:
<223> OTHER INFORMATION: R2

<400> SEQUENCE: 20
caggtccccc gccgcatgat cgg                                           23

<210> SEQ ID NO 21
<211> LENGTH: 23
<212> TYPE: DNA
<213> ORGANISM: Oryza sativa
<220> FEATURE:
<223> OTHER INFORMATION: R3

<400> SEQUENCE: 21
ccgcatgatc ggcaccgacg cct                                           23

<210> SEQ ID NO 22
<211> LENGTH: 23
<212> TYPE: DNA
<213> ORGANISM: Oryza sativa
<220> FEATURE:
<223> OTHER INFORMATION: R4

<400> SEQUENCE: 22
cctatgatcc caagtggggg cgc                                           23

<210> SEQ ID NO 23
<211> LENGTH: 23
<212> TYPE: DNA
<213> ORGANISM: Oryza sativa
<220> FEATURE:
<223> OTHER INFORMATION: R5

<400> SEQUENCE: 23
tattgattct gttgtgggca agg                                           23

-continued

```
<210> SEQ ID NO 24
<211> LENGTH: 23
<212> TYPE: DNA
<213> ORGANISM: Oryza sativa
<220> FEATURE:
<223> OTHER INFORMATION: R6

<400> SEQUENCE: 24
ccagtgctta ttctagggca tat                                              23

<210> SEQ ID NO 25
<211> LENGTH: 23
<212> TYPE: DNA
<213> ORGANISM: Oryza sativa
<220> FEATURE:
<223> OTHER INFORMATION: R7

<400> SEQUENCE: 25
ccggtgcata cagcgtcttg acc                                              23

<210> SEQ ID NO 26
<211> LENGTH: 23
<212> TYPE: DNA
<213> ORGANISM: Oryza sativa
<220> FEATURE:
<223> OTHER INFORMATION: R8

<400> SEQUENCE: 26
atcttgctcg acttggcatc cgg                                              23

<210> SEQ ID NO 27
<211> LENGTH: 23
<212> TYPE: DNA
<213> ORGANISM: Oryza sativa
<220> FEATURE:
<223> OTHER INFORMATION: R9

<400> SEQUENCE: 27
tctgcactga acaagcttct tgg                                              23

<210> SEQ ID NO 28
<211> LENGTH: 23
<212> TYPE: DNA
<213> ORGANISM: Oryza sativa
<220> FEATURE:
<223> OTHER INFORMATION: R10

<400> SEQUENCE: 28
ccacatgcag ttgggtggtc cca                                              23

<210> SEQ ID NO 29
<211> LENGTH: 23
<212> TYPE: DNA
<213> ORGANISM: Oryza sativa
<220> FEATURE:
<223> OTHER INFORMATION: R11

<400> SEQUENCE: 29
ccatcttact gtttcagatg acc                                              23

<210> SEQ ID NO 30
<211> LENGTH: 23
<212> TYPE: DNA
<213> ORGANISM: Oryza sativa
<220> FEATURE:
<223> OTHER INFORMATION: R12
```

<400> SEQUENCE: 30
ccctgctgac cctggtcagc ttg                                         23

<210> SEQ ID NO 31
<211> LENGTH: 23
<212> TYPE: DNA
<213> ORGANISM: Oryza sativa
<220> FEATURE:
<223> OTHER INFORMATION: R13

<400> SEQUENCE: 31
ttcctcgtgc tggacaagtg tgg                                         23

<210> SEQ ID NO 32
<211> LENGTH: 23
<212> TYPE: DNA
<213> ORGANISM: Oryza sativa
<220> FEATURE:
<223> OTHER INFORMATION: R14

<400> SEQUENCE: 32
ttctgcaacc aagactgcgc agg                                         23

<210> SEQ ID NO 33
<211> LENGTH: 23
<212> TYPE: DNA
<213> ORGANISM: Oryza sativa
<220> FEATURE:
<223> OTHER INFORMATION: R15

<400> SEQUENCE: 33
caagactgcg caggcattgc tgg                                         23

<210> SEQ ID NO 34
<211> LENGTH: 23
<212> TYPE: DNA
<213> ORGANISM: Oryza sativa
<220> FEATURE:
<223> OTHER INFORMATION: R16

<400> SEQUENCE: 34
cctcgctaac tggagaggct tct                                         23

<210> SEQ ID NO 35
<211> LENGTH: 23
<212> TYPE: DNA
<213> ORGANISM: Oryza sativa
<220> FEATURE:
<223> OTHER INFORMATION: R17

<400> SEQUENCE: 35
cgactattgt tgagaacctt agg                                         23

<210> SEQ ID NO 36
<211> LENGTH: 23
<212> TYPE: DNA
<213> ORGANISM: Oryza sativa
<220> FEATURE:
<223> OTHER INFORMATION: R18

<400> SEQUENCE: 36
ccatggctgc agagctacga gga                                         23

<210> SEQ ID NO 37
<211> LENGTH: 23

```
<212> TYPE: DNA
<213> ORGANISM: Oryza sativa
<220> FEATURE:
<223> OTHER INFORMATION: R19

<400> SEQUENCE: 37
ccgcattgag tgctatgctg aga                                        23

<210> SEQ ID NO 38
<211> LENGTH: 23
<212> TYPE: DNA
<213> ORGANISM: Oryza sativa
<220> FEATURE:
<223> OTHER INFORMATION: R20

<400> SEQUENCE: 38
tatgctgaga ggactgcaaa agg                                        23

<210> SEQ ID NO 39
<211> LENGTH: 23
<212> TYPE: DNA
<213> ORGANISM: Oryza sativa
<220> FEATURE:
<223> OTHER INFORMATION: R21

<400> SEQUENCE: 39
ccgcaagggt taattgagat caa                                        23

<210> SEQ ID NO 40
<211> LENGTH: 23
<212> TYPE: DNA
<213> ORGANISM: Oryza sativa
<220> FEATURE:
<223> OTHER INFORMATION: R22

<400> SEQUENCE: 40
gcaatgttct ggaaccgcaa ggg                                        23

<210> SEQ ID NO 41
<211> LENGTH: 23
<212> TYPE: DNA
<213> ORGANISM: Oryza sativa
<220> FEATURE:
<223> OTHER INFORMATION: R23

<400> SEQUENCE: 41
ccaggattgc atgagtcggc ttg                                        23

<210> SEQ ID NO 42
<211> LENGTH: 23
<212> TYPE: DNA
<213> ORGANISM: Oryza sativa
<220> FEATURE:
<223> OTHER INFORMATION: R24

<400> SEQUENCE: 42
ggagcttatc ttgctcgact tgg                                        23

<210> SEQ ID NO 43
<211> LENGTH: 46
<212> TYPE: DNA
<213> ORGANISM: Oryza sativa
<220> FEATURE:
<223> OTHER INFORMATION: R25

<400> SEQUENCE: 43
```

```
caggtccccc gccgcatgat cggcctaccc gggcggcgcg tccatg       46

<210> SEQ ID NO 44
<211> LENGTH: 46
<212> TYPE: DNA
<213> ORGANISM: Oryza sativa
<220> FEATURE:
<223> OTHER INFORMATION: R26

<400> SEQUENCE: 44
caggtccccc gccgcatgat cggccgcatg atcggcaccg acgcct       46

<210> SEQ ID NO 45
<211> LENGTH: 46
<212> TYPE: DNA
<213> ORGANISM: Oryza sativa
<220> FEATURE:
<223> OTHER INFORMATION: R27

<400> SEQUENCE: 45
caggtccccc gccgcatgat cggcctatga tcccaagtgg gggcgc       46

<210> SEQ ID NO 46
<211> LENGTH: 23
<212> TYPE: DNA
<213> ORGANISM: Oryza sativa
<220> FEATURE:
<223> OTHER INFORMATION: R28

<400> SEQUENCE: 46
gctgctgccg ctcaacgagc cgg                                23

<210> SEQ ID NO 47
<211> LENGTH: 23
<212> TYPE: DNA
<213> ORGANISM: Oryza sativa
<220> FEATURE:
<223> OTHER INFORMATION: R29

<400> SEQUENCE: 47
ccaggagctc ggggtgctcg tgg                                23

<210> SEQ ID NO 48
<211> LENGTH: 23
<212> TYPE: DNA
<213> ORGANISM: Oryza sativa
<220> FEATURE:
<223> OTHER INFORMATION: R30

<400> SEQUENCE: 48
ccagaagggc ggctgcggcg ggt                                23

<210> SEQ ID NO 49
<211> LENGTH: 23
<212> TYPE: DNA
<213> ORGANISM: Triticum aestivum
<220> FEATURE:
<223> OTHER INFORMATION: W1

<400> SEQUENCE: 49
caggtccccc gccgcatgat cgg                                23

<210> SEQ ID NO 50
<211> LENGTH: 23
<212> TYPE: DNA
<213> ORGANISM: Triticum aestivum
```

```
<220> FEATURE:
<223> OTHER INFORMATION: W2

<400> SEQUENCE: 50
ccgcatgatc ggcacggacg cgt                                              23

<210> SEQ ID NO 51
<211> LENGTH: 23
<212> TYPE: DNA
<213> ORGANISM: Triticum aestivum
<220> FEATURE:
<223> OTHER INFORMATION: W3

<400> SEQUENCE: 51
cctatgatcc caagcggtgg tgc                                              23

<210> SEQ ID NO 52
<211> LENGTH: 23
<212> TYPE: DNA
<213> ORGANISM: Triticum aestivum
<220> FEATURE:
<223> OTHER INFORMATION: W4

<400> SEQUENCE: 52
ccagtgccta ttctagggcc tat                                              23

<210> SEQ ID NO 53
<211> LENGTH: 23
<212> TYPE: DNA
<213> ORGANISM: Triticum aestivum
<220> FEATURE:
<223> OTHER INFORMATION: W5

<400> SEQUENCE: 53
cctattctag ggcctatgag gag                                              23

<210> SEQ ID NO 54
<211> LENGTH: 23
<212> TYPE: DNA
<213> ORGANISM: Triticum aestivum
<220> FEATURE:
<223> OTHER INFORMATION: W6

<400> SEQUENCE: 54
tttacgctta catttgtgac tgg                                              23

<210> SEQ ID NO 55
<211> LENGTH: 23
<212> TYPE: DNA
<213> ORGANISM: Triticum aestivum
<220> FEATURE:
<223> OTHER INFORMATION: W7

<400> SEQUENCE: 55
ggagcatatc ttgctcgact tgg                                              23

<210> SEQ ID NO 56
<211> LENGTH: 23
<212> TYPE: DNA
<213> ORGANISM: Triticum aestivum
<220> FEATURE:
<223> OTHER INFORMATION: W8

<400> SEQUENCE: 56
cccacatgca gttgggtggc ccc                                              23
```

```
<210> SEQ ID NO 57
<211> LENGTH: 23
<212> TYPE: DNA
<213> ORGANISM: Triticum aestivum
<220> FEATURE:
<223> OTHER INFORMATION: W9

<400> SEQUENCE: 57
agctcccaca tgcagttggg tgg                                              23

<210> SEQ ID NO 58
<211> LENGTH: 23
<212> TYPE: DNA
<213> ORGANISM: Triticum aestivum
<220> FEATURE:
<223> OTHER INFORMATION: W10

<400> SEQUENCE: 58
ccatctgaca gtttcagatg acc                                              23

<210> SEQ ID NO 59
<211> LENGTH: 23
<212> TYPE: DNA
<213> ORGANISM: Triticum aestivum
<220> FEATURE:
<223> OTHER INFORMATION: W11

<400> SEQUENCE: 59
ccttgctaac tggagaggct tct                                              23

<210> SEQ ID NO 60
<211> LENGTH: 23
<212> TYPE: DNA
<213> ORGANISM: Triticum aestivum
<220> FEATURE:
<223> OTHER INFORMATION: W12

<400> SEQUENCE: 60
ttcatccttg ctaactggag agg                                              23

<210> SEQ ID NO 61
<211> LENGTH: 23
<212> TYPE: DNA
<213> ORGANISM: Triticum aestivum
<220> FEATURE:
<223> OTHER INFORMATION: W13

<400> SEQUENCE: 61
caacaattgt tgagaacctt agg                                              23

<210> SEQ ID NO 62
<211> LENGTH: 23
<212> TYPE: DNA
<213> ORGANISM: Triticum aestivum
<220> FEATURE:
<223> OTHER INFORMATION: W14

<400> SEQUENCE: 62
agagctacgt ggaggggctt ggg                                              23

<210> SEQ ID NO 63
<211> LENGTH: 23
<212> TYPE: DNA
<213> ORGANISM: Triticum aestivum
<220> FEATURE:
<223> OTHER INFORMATION: W15
```

-continued

```
<400> SEQUENCE: 63
tatgctgaga ggactgcaaa ggg                                           23

<210> SEQ ID NO 64
<211> LENGTH: 23
<212> TYPE: DNA
<213> ORGANISM: Triticum aestivum
<220> FEATURE:
<223> OTHER INFORMATION: W16

<400> SEQUENCE: 64
cctaccctgg cggcgcgtcc atg                                           23

<210> SEQ ID NO 65
<211> LENGTH: 23
<212> TYPE: DNA
<213> ORGANISM: Triticum aestivum
<220> FEATURE:
<223> OTHER INFORMATION: W17

<400> SEQUENCE: 65
ccctgctgat ccaggccagc ttg                                           23

<210> SEQ ID NO 66
<211> LENGTH: 23
<212> TYPE: DNA
<213> ORGANISM: Triticum aestivum
<220> FEATURE:
<223> OTHER INFORMATION: W18

<400> SEQUENCE: 66
ccagcttgat tcccatgagc ggt                                           23

<210> SEQ ID NO 67
<211> LENGTH: 23
<212> TYPE: DNA
<213> ORGANISM: Triticum aestivum
<220> FEATURE:
<223> OTHER INFORMATION: W19

<400> SEQUENCE: 67
ttcctcgtgc tgggcaagtc tgg                                           23

<210> SEQ ID NO 68
<211> LENGTH: 23
<212> TYPE: DNA
<213> ORGANISM: Triticum aestivum
<220> FEATURE:
<223> OTHER INFORMATION: W20

<400> SEQUENCE: 68
taagacagcg caggcaatgc tgg                                           23

<210> SEQ ID NO 69
<211> LENGTH: 23
<212> TYPE: DNA
<213> ORGANISM: Triticum aestivum
<220> FEATURE:
<223> OTHER INFORMATION: W21

<400> SEQUENCE: 69
ttcagctact aagacagcgc agg                                           23

<210> SEQ ID NO 70
```

```
<211> LENGTH: 23
<212> TYPE: DNA
<213> ORGANISM: Triticum aestivum
<220> FEATURE:
<223> OTHER INFORMATION: W22

<400> SEQUENCE: 70
gtaatgttct tgaacctcaa ggg                                              23

<210> SEQ ID NO 71
<211> LENGTH: 23
<212> TYPE: DNA
<213> ORGANISM: Triticum aestivum
<220> FEATURE:
<223> OTHER INFORMATION: W23

<400> SEQUENCE: 71
cctcaagggt tgattgagat caa                                              23

<210> SEQ ID NO 72
<211> LENGTH: 23
<212> TYPE: DNA
<213> ORGANISM: Triticum aestivum
<220> FEATURE:
<223> OTHER INFORMATION: W24

<400> SEQUENCE: 72
ccaagagtgc atgggcaggc ttg                                              23

<210> SEQ ID NO 73
<211> LENGTH: 23
<212> TYPE: DNA
<213> ORGANISM: Triticum aestivum
<220> FEATURE:
<223> OTHER INFORMATION: W25

<400> SEQUENCE: 73
aactgcaatg cggccactga cgg                                              23

<210> SEQ ID NO 74
<211> LENGTH: 23
<212> TYPE: DNA
<213> ORGANISM: Triticum aestivum
<220> FEATURE:
<223> OTHER INFORMATION: W26

<400> SEQUENCE: 74
aactgcaatg cgtccattga cgg                                              23

<210> SEQ ID NO 75
<211> LENGTH: 23
<212> TYPE: DNA
<213> ORGANISM: Triticum aestivum
<220> FEATURE:
<223> OTHER INFORMATION: W27

<400> SEQUENCE: 75
aactgcaatg cggccattga cgg                                              23

<210> SEQ ID NO 76
<211> LENGTH: 23
<212> TYPE: DNA
<213> ORGANISM: Triticum aestivum
<220> FEATURE:
<223> OTHER INFORMATION: W28

<400> SEQUENCE: 76
```

```
gctgctgccg ctcaacgagc cgg                                              23
```

<210> SEQ ID NO 77
<211> LENGTH: 23
<212> TYPE: DNA
<213> ORGANISM: Triticum aestivum
<220> FEATURE:
<223> OTHER INFORMATION: W29

<400> SEQUENCE: 77

```
ccaggagctg ggggtgctcg tcg                                              23
```

<210> SEQ ID NO 78
<211> LENGTH: 23
<212> TYPE: DNA
<213> ORGANISM: Triticum aestivum
<220> FEATURE:
<223> OTHER INFORMATION: W30

<400> SEQUENCE: 78

```
ccagaagggt ggctgcggcg ggt                                              23
```

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Gly Gly Ser
1               5

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 82

Lys Lys Arg Lys Val
1               5

<210> SEQ ID NO 83
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aagaagagaa aggtc                                                     15

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Lys Lys Lys Arg Lys Val
1               5

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cccaagaaga agaggaaggt g                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccaaagaaga agaggaaggt t                                              21

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Gly Gly Ser Pro Lys Lys Lys Arg Lys Val
1               5                   10

<210> SEQ ID NO 88
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 88
tcggggggga gcccaaagaa gaagcggaag gtg                                    33

<210> SEQ ID NO 89
<211> LENGTH: 46
<212> TYPE: DNA
<213> ORGANISM: Triticum aestivum

<400> SEQUENCE: 89
caggtccccc gccgcatgat cggcctaccc tggcggcgcg tccatg                      46

<210> SEQ ID NO 90
<211> LENGTH: 46
<212> TYPE: DNA
<213> ORGANISM: Triticum aestivum

<400> SEQUENCE: 90
caggtccccc gccgcatgat cggccgcatg atcggcacgg acgcgt                      46

<210> SEQ ID NO 91
<211> LENGTH: 46
<212> TYPE: DNA
<213> ORGANISM: Triticum aestivum

<400> SEQUENCE: 91
caggtccccc gccgcatgat cggcctatga tcccaagcgg tggtgc                      46

<210> SEQ ID NO 92
<211> LENGTH: 46
<212> TYPE: DNA
<213> ORGANISM: Triticum aestivum

<400> SEQUENCE: 92
caggtccccc gccgcatgat cggttcagct actaagacag cgcagg                      46

<210> SEQ ID NO 93
<211> LENGTH: 23
<212> TYPE: DNA
<213> ORGANISM: Triticum aestivum

<400> SEQUENCE: 93
caggtccccc gccgcatgat cgg                                               23
```

CREATION OF HERBICIDE RESISTANT GENE AND USE THEREOF

CROSS REFERENCE TO RELATED APPLICATIONS

This application is a divisional of U.S. application Ser. No. 16/612,158, filed Nov. 8, 2019, which is a U.S. National Phase of International Patent Application No. PCT/CN2018/086501, filed May 11, 2018, which claims priority to Chinese Patent Application No. 201710329242.9, filed May 11, 2017, all of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Nov. 30, 2020, is named 245761_000090_SL.txt and is 184,980 bytes in size.

TECHNICAL FIELD

The present invention belongs to the field of plant genetic engineering. Specifically, the invention relates to a method for creating novel herbicide resistant plants by base editing techniques and a method for screening endogenous gene mutations capable of conferring herbicide resistance in plants. The invention also relates to the use of the identified endogenous gene mutantations in crop breeding.

BACKGROUND

Weeds are major threaten to crops, which not only affect the yield and quality of crops, but also transmit agricultural pests and diseases. Therefore, effective weed control is the prerequisite for achieving high yields in agriculture. Traditional manual weeding is inefficient and leads to high cost, and thus has been gradually replaced by spraying chemical herbicides during the growth of crops. At present, in China's agricultural production, the area and amount of herbicide applied have exceeded pesticides and fungicides.

The working mechanisms of herbicides can be divided into three categories: the first is to inhibit the enzymes involved in the plant photosynthesis system; the second is to inhibit cell metabolism, such as inhibition of synthesis of amino acid or fatty acid; the third is to inhibit cell growth/division, including inhibition of microtube assembly or interfering with plant hormone systems. The enzymes that herbicides inhibit are also sensitive in many crops; therefore, many herbicides can cause serious damage to the crop while controlling the weed. Therefore, it is of great significance to improve crop resistance to herbicides.

There are two main strategies to increase crop resistance to herbicides. One is target resistance, which means that the enzymes that are inhibited by herbicides have been mutated such that herbicides cannot effectively inhibit their physiological activities. This strategy generally involves resistance to imidazolinone, glyphosate, sulphonylurea, atrazine and the like. The second is detoxification, that is, to protect the physiological function of the target enzyme through the rapid degradation of herbicides. This strategy generally involves the plant endogenous P450 enzyme system and resistance to glufosinate, 2,4-D, dicamba and the like by transgenes.

There are currently two different technical approaches to achieving herbicide resistance in plants: i) traditional crop breeding, including chemical mutagenesis, radiation mutagenesis, etc.; and ii) transgenes, that is, incorporation of herbicide resistant genes into plants of interest. However, the probability of obtaining herbicide-resistant mutations (especially multiple mutations in a same gen) by traditional breeding produces is very low, and it is possible to produce linked undesired mutations. Transgenic technology can only introduce known herbicide-resistant genes into the plant of interest to confer the expected herbicide resistance.

There is still a need in the art for simpler and more efficient methods for obtaining herbicide-resistant plants and new herbicide-resistant genes.

DETAILED DESCRIPTION OF THE INVENTION

I. Definition

Figure 1:
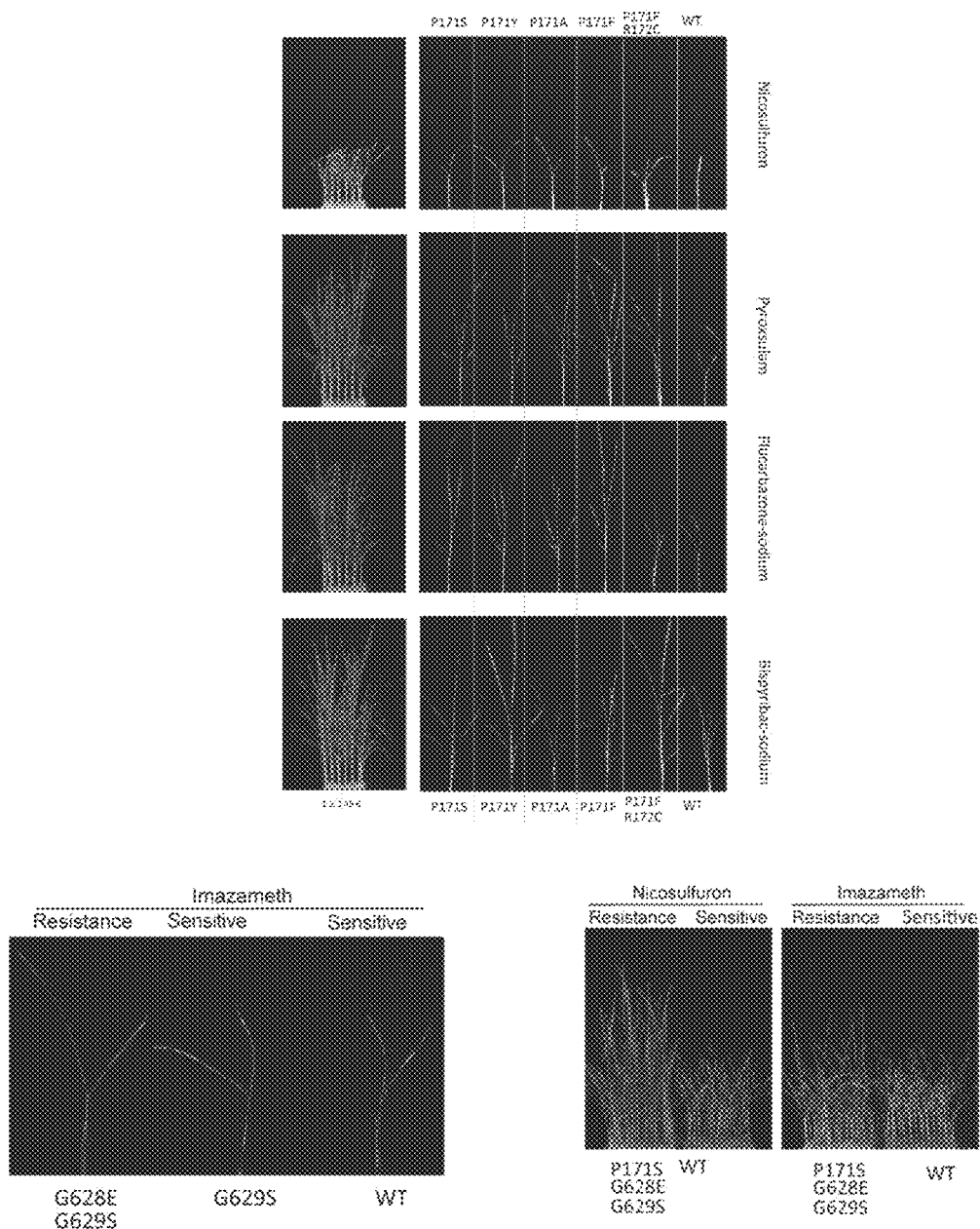
FIG. 1. shows the screening of resistant mutations in rice ALS.

In the present invention, unless indicated otherwise, the scientific and technological terminologies used herein refer to meanings commonly understood by a person skilled in the art. Also, the terminologies and experimental procedures used herein relating to protein and nucleotide chemistry, molecular biology, cell and tissue cultivation, microbiology, immunology, all belong to terminologies and conventional methods generally used in the art. For example, the standard DNA recombination and molecular cloning technology used herein are well known to a person skilled in the art, and are described in details in the following references: Sambrook, J., Fritsch, E. F. and Maniatis, T., Molecular Cloning: A Laboratory Manual; Cold Spring Harbor Laboratory Press: Cold Spring Harbor, 1989 (hereinafter refers to as "Sambrook et al"). In the meantime, in order to better understand the present invention, definitions and explanations for the relevant terminologies are provided below.

"Cas9 nuclease" and "Cas9" can be used interchangeably herein, which refer to a RNA directed nuclease, including the Cas9 protein or fragments thereof (such as a protein comprising an active DNA cleavage domain of Cas9 and/or a gRNA binding domain of Cas9). Cas9 is a component of the CRISPR/Cas (clustered regularly interspaced short palindromic repeats and its associated system) genome editing system, which targets and cleaves a DNA target sequence to form a DNA double strand breaks (DSB) under the guidance of a guide RNA.

"guide RNA" and "gRNA" can be used interchangeably herein, which typically are composed of crRNA and tracrRNA molecules forming complexes through partial complement, wherein crRNA comprises a sequence that is sufficiently complementary to a target sequence for hybridization and directs the CRISPR complex (Cas9+crRNA+tracrRNA) to specifically bind to the target sequence. However, it is known in the art that single guide RNA (sgRNA) can be designed, which comprises the characteristics of both crRNA and tracrRNA.

"Deaminase" refers to an enzyme that catalyzes the deamination reaction. In some embodiments of the present invention, the deaminase refers to a cytidine deaminase, which catalyzes the deamination of a cytidine or a deoxycytidine to a uracil or a deoxyuridine, respectively.

"Genome" as it applies to plant cells encompasses not only chromosomal DNA found within the nucleus, but organelle DNA found within subcellular components (e.g., mitochondrial, plastid) of the cell.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, and includes protoplast cells without a cell wall and plant cells with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast", as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

"Progeny" of a plant comprises any subsequent generation of the plant.

A "genetically modified plant" includes a plant which comprises within its genome an exogenous polynucleotide. For example, the exogenous polynucleotide is stably integrated within the genome such that the polynucleotide is passed on to successive generations. The exogenous polynucleotide may be integrated into the genome alone or as part of a recombinant DNA construct. The modified gene or expression regulatory sequence means that, in the plant genome, said sequence comprises one or more nucleotide substitution, deletion, or addition. For example, a genetically modified plant obtained by the present invention may contain one or more C to T substitutions relative to the wild type plant (corresponding plant that is not genetically modified).

The term "exogenous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

As used herein, an "expression construct" refers to a vector suitable for expression of a nucleotide sequence of interest in a plant, such as a recombinant vector. "Expression" refers to the production of a functional product. For example, the expression of a nucleotide sequence may refer to transcription of the nucleotide sequence (such as transcribe to produce an mRNA or a functional RNA) and/or translation of RNA into a protein precursor or a mature protein.

"Expression construct" of the invention may be a linear nucleic acid fragment, a circular plasmid, a viral vector, or, in some embodiments, an RNA that can be translated (such as an mRNA).

"Expression construct" of the invention may comprise regulatory sequences and nucleotide sequences of interest that are derived from different sources, or regulatory sequences and nucleotide sequences of interest derived from the same source, but arranged in a manner different than that normally found in nature.

"Regulatory sequence" or "regulatory element" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. A plant expression regulatory element refers to a nucleotide sequence capable of controlling the transcription, RNA processing or stability or translation of a nucleotide sequence of interest in a plant.

Regulatory sequences may include, but are not limited to, promoters, translation leader sequences, introns, and polyadenylation recognition sequences.

"Promoter" refers to a nucleic acid fragment capable of controlling transcription of another nucleic acid fragment. In some embodiments of the invention, the promoter is a promoter capable of controlling gene transcription in a plant cell whether or not its origin is from a plant cell. The promoter may be a constitutive promoter or a tissue-specific promoter or a developmentally regulated promoter or an inducible promoter.

"Constitutive promoter" refers to a promoter that generally causes gene expression in most cell types in most circumstances. "Tissue-specific promoter" and "tissue-preferred promoter" are used interchangeably, and refer to a promoter that is expressed predominantly but not necessarily exclusively in one tissue or organ, but that may also be expressed in one specific cell or cell type. "Developmentally regulated promoter" refers to a promoter whose activity is determined by developmental events. "Inducible promoter" selectively expresses a DNA sequence operably linked to it in response to an endogenous or exogenous stimulus (environment, hormones, or chemical signals, and so on).

As used herein, the term "operably linked" means that a regulatory element (for example but not limited to, a promoter sequence, a transcription termination sequence, and so on) is associated to a nucleic acid sequence (such as a coding sequence or an open reading frame), such that the transcription of the nucleotide sequence is controlled and regulated by the transcriptional regulatory element. Techniques for operably linking a regulatory element region to a nucleic acid molecule are known in the art.

"Introduction" of a nucleic acid molecule (such as a plasmid, a linear nucleic acid fragment, RNA, and so on) or protein into a plant means transforming the plant cell with the nucleic acid or protein so that the nucleic acid or protein can function in the plant cell. "Transformation" as used herein includes stable transformation and transient transformation.

"Stable transformation" refers to introducing an exogenous nucleotide sequence into a plant genome, resulting in genetically stable inheritance. Once stably transformed, the exogenous nucleic acid sequence is stably integrated into the genome of the plant and any successive generations thereof.

"Transient transformation" refers to introducing a nucleic acid molecule or protein into a plant cell, performing its function without stable inheritance. In transient transformation, the exogenous nucleic acid sequence is not integrated into the plant genome.

II. Base Editing System for Generating Herbicide-Resistant Plants

The present invention provides a system for base editing of a herbicide resistance related gene in the genome of a plant, comprising at least one of the following (i) to (v):

i) a base editing fusion protein, and a guide RNA;

ii) an expression construct comprising a nucleotide sequence encoding a base editing fusion protein, and a guide RNA;

iii) a base editing fusion protein, and an expression construction comprising a nucleotide sequence encoding a guide RNA;

iv) an expression construct comprising a nucleotide sequence encoding a base editing fusion protein, and an expression construct comprising a nucleotide sequence encoding a guide RNA;

v) an expression construct comprising a nucleotide sequence encoding base editing fusion protein and a nucleotide sequence encoding guide RNA;

wherein said base editing fusion protein contains a nuclease-inactivated CRISPR nuclease domain (such as nuclease-inactivated Cas9 domain) and a deaminase domain, said guide RNA can target said base editing fusion protein to a target sequence in the herbicide resistance related gene in the plant genome.

The herbicide resistance-related gene may be a gene encoding a protein having an important physiological activity in a plant, which may be inhibited by the herbicide. Mutation in such herbicide-resistance-related gene may reverse the inhibition of herbicide and retain its physiological activity. Alternatively, the herbicide resistance related gene may encode a protein that is capable of degrading herbicides. Increasing the expression of such herbicide-associated gene or enhancing its degradation activity can result in increased resistance to herbicides.

In some embodiments of the present invention, herbicide resistance-related genes include, but are not limited to, PsbA gene (resistant to atrazine, etc.), ALS (acetolactate synthase) gene (resistant to sulfonylurea, Imidazolidinone, etc.), EPSPS (5-enolpyruvate oxalate-3-phosphate synthase) gene (resistant to glyphosate), ACCase (acetyl-CoA carboxylase) gene (resistant to sethoxydim, etc.), PPO (protoporphyrinogen oxidase) gene (resistant to carfentrazone-ethyl etc.) and HPPD (p-hydroxyphenylpyruvate dioxygenase) gene (resistant to mesotrione etc.), PDS (Phytoene dehydrogenase) (resistant to diflufenican etc.), GS (glutamine synthetase) (target of herbicides such as glufosinate), DOXPS (target of herbicides such as clomazone), P450 (involved in the degradation of herbicides).

In some embodiments, the guide RNA targets one or more of SEQ ID NOs: 19-78.

There is no specific limitation to the nuclease-inactivated CRISPR nuclease that can be used in the present invention, provided that it retains the capability of targeting specific DNA under the guidance of gRNA, for example, those derived from Cas9, Cpf1 and the like can be used. Nuclease-inactivated Cas9 nuclease is preferred.

The DNA cleavage domain of Cas9 nuclease is known to contain two subdomains: the HNH nuclease subdomain and the RuvC subdomain. HNH subdomains cleave the chain that is complementary to gRNA, whereas the RuvC subdomain cleaves the non-complementary chain. Mutations in these subdomains can inactivate Cas9 nuclease to form "nuclease-inactivated Cas9". The nuclease-inactivated Cas9 retains DNA binding capacity directed by gRNA. Thus, in principle, when fused with an additional protein, the nuclease-inactivated Cas9 can simply target said additional protein to almost any DNA sequence through co-expression with appropriate guide RNA.

Cytidine deaminase can catalyze the deamination of cytidine (C) in DNA to form uracil (U). If nuclease-inactivated Cas9 is fused with Cytidine deaminase, the fusion protein can target a target sequence in the genome of a plant through the direction of a guide RNA. The DNA double strand is not cleaved due to the loss of Cas9 nuclease activity, whereas the deaminase domain in the fusion protein is capable of converting the cytidine of the single-strand DNA produced during the formation of the Cas9-guide RNA-DNA complex into a U, and then C to T substitution may be achieved by base mismatch repair.

Therefore, in some embodiments of the invention, the deaminase is a cytidine deaminase, such as an apolipoprotein B mRNA editing complex (APOBEC) family deaminase. Particularly, the deaminase described herein is a deaminase that can accept single-strand DNA as the substrate.

Examples of cytidine deaminase can be used in the present invention include but are not limited to APOBEC1 deaminase, activation-induced cytidine deaminase (AID), APOBEC3G, or CDA1.

In some specific embodiments of the present invention, the cytidine deaminase comprises an amino acid sequence shown in positions 9-235 of SEQ ID NO: 10 or 11.

The nuclease-inactivated Cas9 of the present invention can be derived from Cas9 of different species, for example, derived from S. pyogenes Cas9 (SpCas9, the amino acid sequence is shown in SEQ ID NO: 5). Mutations in both the HNH nuclease subdomain and the RuvC subdomain of the SpCas9 (includes, for example, D10A and H840A mutations) inactivate S. pyogenes Cas9 nuclease, resulting in a nuclease dead Cas9 (dCas9). Inactivation of one of the subdomains by mutation allows Cas9 to gain nickase activity, i.e., resulting in a Cas9 nickase (nCas9), for example, nCas9 with a D10A mutation only.

Therefore, in some embodiments of the invention, the nuclease-inactivated Cas9 of the invention comprises amino acid substitutions D10A and/or H840A relative to wild-type Cas9.

In some preferred embodiments of the invention, the nuclease-inactivated Cas9 of the invention has nickase activity. Without being bound by any theory, it is believed that Eukaryotic mismatch repair uses nicks on a DNA strand for the removal and repair of the mismatched base in the DNA strand. The U: G mismatch formed by cytidine deaminase may be repaired into C: G. Through the introduction of a nick on the chain containing unedited G, it will be possible to preferentially repair the U: G mismatch to the desired U:A or T:A. Therefore, preferably, the nuclease-inactivated Cas9 is a Cas9 nickase that retains the cleavage activity of the HNH subdomain of Cas9, whereas the cleavage activity of the RuvC subdomain is inactivated. For example, the nuclease-inactivated Cas9 contains an amino acid substitution D10A relative to wild-type Cas9.

In some embodiments of the present invention, the nuclease-inactivated Cas9 comprises the amino acid sequence of SEQ ID NO:6. In some preferred embodiments, the nuclease-inactivated Cas9 comprises the amino acid sequence of SEQ ID NO: 7.

In some embodiments of the invention, the deaminase domain is fused to the N-terminus of the nuclease-inactivated Cas9 domain. In some embodiments, the deaminase domain is fused to the C-terminus of the nuclease-inactivated Cas9 domain.

In some embodiments of the invention, the deaminase domain and the nuclease inactivated Cas9 domain are fused through a linker. The linker can be a non-functional amino acid sequence having no secondary or higher structure, which is 1 to 50 (for example, 1, 2, 3, 4, 5, 6, 7, 8, 9, 10, 11, 12, 13, 14, 15, 16, 17, 18, 19, 20, or 20-25, 25-50) or more amino acids in length. For example, the linker may be a flexible linker, such as GGGGS (SEQ ID NO: 79), GS, GAP, (GGGGS) x3 (SEQ ID NO: 80), GGS, (GGS) x7 (SEQ ID NO: 81), and the like. In some preferred embodiments, the linker is an XTEN linker as shown in SEQ ID NO: 8.

In cells, uracil DNA glycosylase catalyzes the removal of U from DNA and initiates base excision repair (BER), which results in the repair of U: G to C: G. Therefore, without any theoretical limitation, including uracil DNA glycosylase inhibitor in the base editing fusion protein of the invention or the system of the present invention will be able to increase the efficiency of base editing.

Accordingly, in some embodiments of the invention, the base editing fusion protein further comprises a uracil DNA glycosylase inhibitor (UGI). In some embodiments, the uracil DNA glycosylase inhibitor comprises the amino acid sequence set forth in SEQ ID NO: 9.

In some embodiments of the invention, the base editing fusion protein of the invention further comprises a nuclear localization sequence (NLS). In general, one or more NLSs in the base editing fusion protein should have sufficient strength to drive the accumulation of the base editing fusion protein in the nucleus of a plant cell in an amount sufficient for the base editing function. In general, the strength of the nuclear localization activity is determined by the number and position of NLSs, and one or more specific NLSs used in the base editing fusion protein, or a combination thereof.

In some embodiments of the present invention, the NLSs of the base editing fusion protein of the invention may be located at the N-terminus and/or the C-terminus. In some embodiments, the base editing fusion protein comprises about 1, 2, 3, 4, 5, 6, 7, 8, 9, 10, or more NLSs. In some embodiments, the base editing fusion protein comprises about 1, 2, 3, 4, 5, 6, 7, 8, 9, 10, or more NLSs at or near the N-terminus. In some embodiments, the base-editing fusion protein comprises about 1, 2, 3, 4, 5, 6, 7, 8, 9, 10, or more NLSs at or near the C-terminus. In some embodiments, the base editing fusion protein comprises a combination of these, such as one or more NLSs at the N-terminus and one or more NLSs at the C-terminus. Where there are more than one NLS, each NLS may be selected as independent from other NLSs. In some preferred embodiments of the invention, the base-editing fusion protein comprises two NLSs, for example, the two NLSs are located at the N-terminus and the C-terminus, respectively.

In general, NLS consists of one or more short sequences of positively charged lysine or arginine exposed on the surface of a protein, but other types of NLS are also known in the art. Non-limiting examples of NLSs include KKRKV (SEQ ID NO: 82) (nucleotide sequence 5'-AAGAAGAGAAAGGTC-3' (SEQ ID NO: 83)), PKKKRKV (SEQ ID NO: 84) (nucleotide sequence 5'-CCAAGAAGAAGAGGAAGGTG-3' (SEQ ID NO: 85) or CCAAAGAAGAAGAGGAAGGTT (SEQ ID NO: 86)), or SGGSPKKKRKV (SEQ ID NO: 87) (nucleotide sequence 5'-TCGGGGGGGAGCCCAAAGAAGAAGCG-GAAGGTG-3' (SEQ ID NO: 88)).

In some embodiments of the invention, the N-terminus of the base editing fusion protein comprises an NLS with an amino acid sequence shown by PKKKRKV (SEQ ID NO: 84). In some embodiments of the invention, the C-terminus of the base-editing fusion protein comprises an NLS with an amino acid sequence shown by SGGSPKKKRKV (SEQ ID NO: 87).

In addition, the base editing fusion protein of the present invention may also include other localization sequences, such as cytoplasmic localization sequences, chloroplast localization sequences, mitochondrial localization sequences, and the like, depending on the location of the DNA to be edited.

In some embodiments of the present invention, the base editing fusion protein comprises the amino acid sequence set forth in SEQ ID NO: 10 or 11.

In order to obtain efficient expression in plants, in some embodiments of the invention, the nucleotide sequence encoding the base editing fusion protein is codon optimized for the plant to be base edited.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000).

In some embodiments of the invention, the codon-optimized nucleotide sequence encoding the base editing fusion protein is set forth in SEQ ID NO: 12 or 13.

In some embodiments of the invention, the guide RNA is a single guide RNA (sgRNA). Methods of constructing suitable sgRNAs according to a given target sequence are known in the art. See e.g., Wang, Y. et al. Simultaneous editing of three homoeoalleles in hexaploid bread wheat confers heritable resistance to powdery mildew. *Nat. Biotechnol.* 32, 947-951 (2014); Shan, Q. et al. Targeted genome modification of crop plants using a CRISPR-Cas system. *Nat. Biotechnol.* 31, 686-688 (2013); Liang, Z. et al. Targeted mutagenesis in *Zea mays* using TALENs and the CRISPR/Cas system. *J Genet Genomics.* 41, 63-68 (2014).

In some embodiments of the invention, the nucleotide sequence encoding the base-editing fusion protein and/or the nucleotide sequence encoding the guide RNA is operably linked to a plant expression regulatory element, such as a promoter.

Examples of promoters that can be used in the present invention include but not limited to the cauliflower mosaic virus 35S promoter (Odell et al. (1985) *Nature* 313: 810-812), a maize Ubi-1 promoter, a wheat U6 promoter, a rice U3 promoter, a maize U3 promoter, a rice actin promoter, a TrpPro5 promoter (U.S. patent application Ser. No. 10/377, 318; filed on Mar. 16, 2005), a pEMU promoter (Last et al. *Theor. Appl. Genet.* 81: 581-588), a MAS promoter (Velten et al. (1984) *EMBO J.* 3: 2723-2730), a maize H3 histone promoter (Lepetit et al. *Mol. Gen. Genet.* 231: 276-285 and Atanassova et al. (1992) *Plant J.* 2 (3): 291-300), and a *Brassica napus* ALS3 (PCT Application WO 97/41228) promoters. Promoters that can be used in the present invention also include the commonly used tissue specific promoters as reviewed in Moore et al. (2006) *Plant J.* 45 (4): 651-683.

III. Method for Producing Herbicide-Resistant Plants by Base Editing

In another aspect, the present invention provides a method for producing a herbicide-resistant plant, comprising introducing into the plant a system of the present invention for base-editing a herbicide resistance-related gene in the plant genome, thereby the guide RNA targets the base-editing fusion protein to a target sequence of a herbicide resistance-related gene in the plant, resulting in one or more nucleotide substitutions in the target sequence.

In some embodiments, the method further comprises the step of screening the plants for herbicide resistance.

In some embodiments, the herbicide resistance-related gene encodes a herbicide resistance-related protein. In some embodiments of the present invention, herbicide resistance-related proteins include, but are not limited to, PsbA (resistant to atrazine, etc.), ALS (resistant to sulfonylurea, Imidazolidinone, etc.), EPSPS (resistant to glyphosate), ACCase (resistant to sethoxydim, etc.), PPO (resistant to carfentrazone-ethyl etc.) and HPPD (resistant to mesotrione etc.), PDS (resistant to diflufenican etc.), GS (target of herbicides such as glufosinate), DOXPS (target of herbicides such as clomazone), P450 (involved in the degradation of herbicides).

In some embodiments, the nucleotide substitution is a C to T substitution. In some embodiments, the nucleotide substitution is a C to A or C to G substitution. In some embodiments, the nucleotide substitution in located in the non-coding region in the herbicide resistance related gene, such as expression regulation regions. In some embodiments, the nucleotide substitution results in amino acid substitution in the herbicide resistance protein encoded by the gene. In some embodiments, the nucleotide substitution and/or amino acid substitution confer herbicide resistance to the plant.

In some embodiments of the present invention, the nucleotide substitution and/or amino acid substitution that confer herbicide resistance to a plant may be any known substitution that confers herbicide resistance to a plant in a herbicide resistance-related gene. By the method of the present invention, single mutations, double mutations or multiple mutations capable of conferring herbicide resistance can be created in situ in plants without the need of transgene. The mutations may be known in the art or may be newly identified by the methods of the present invention.

The present invention provides a method for producing a herbicide-resistant plant, comprising modifying the ALS gene in a plant by the base-editing method of the present invention, resulting in one or more amino acid mutations in the ALS which confer herbicide resistance to the plant. In some embodiments, the amino acid mutation is selected from A122T, P197S, P197L, P197F, R198C, D204N, A205T, D204N+A205T, G654K, G655D, G655S, G655N, G654K+G655D, G654K+G655S, G654K+G655N, G659N, P197S, P197L, P197F, D204N, A205T, D204N+A205T, G654D, G654S, G654N, G655D, G655S, G655N, G654D+G655D, G654D+G655S, G654D+G655N, G654S+G655D, G654S+G655S, G654S+G655N, G654N+G655D, G654N+G655S, G654N+G655N, A122T, or any combination thereof, wherein the amino acid position refers to SEQ ID No: 2 (amino acid sequence of ALS in *Arabidopsis thaliana*, Genbank accession NO: NP_190425). In some specific embodiments, the amino acid mutation is selected from P197A, P197F, P197S, P197Y, P197F+R198C, G654E+G655S, G654K+G655S, G654E+G659N, P197F+G654E+G655S, or any combination thereof, wherein wherein the amino acid position refers to SEQ ID No: 2 (amino acid sequence of ALS in *Arabidopsis thaliana*, Genbank accession NO: NP_190425).

Thus, in some embodiments, the guide RNA targets a target sequence comprising a sequence encoding amino acid(s) selected from the group consisting of A122, P197, R198, D204, A205, G654, G655, G659 or any combination thereof, wherein the amino acid position refers to SEQ. ID No: 2 (amino acid sequence of ALS in *Arabidopsis thaliana*, Genbank accession NO: NP_190425).

In some embodiments, the ALS is rice ALS and its wild-type sequence is shown in SEQ ID No:16. In some embodiments, the ALS is wheat ALS and the wild-type sequence thereof is shown in SEQ ID No: 17 (partial sequence, genbank ID: AAO53548.1).

The present invention provides a method for producing a herbicide-resistant plant, comprising modifying a PsbA gene in a plant by the base editing method of the present invention, resulting in one or more amino acid mutations in PsbA which confer herbicide resistance to the plant.

The present invention provides a method for producing a herbicide-resistant plant, comprising modifying the EPSPS gene in a plant by the base-editing method of the present invention, resulting in one or more amino acid mutaions in the EPSPS which confer herbicide resistance to the plant. In some embodiments, the amino acid mutation is selected from the group consisting of T102I, A103V, T102I+A103V, wherein the amino acid position refers to SEQ ID No: 4 (Wheat A genome EPSPS amino acid sequence, Genbank accession NO: ALK27163).

Therefore, in some embodiments, the guide RNA targets a target sequence comprising a sequence encoding amino acid(s) selected from the group consisting of T102 and/or A103, wherein the amino acid positions refer to SEQ ID No:4.

The present invention provides a method for producing a herbicide-resistant plant, comprising modifying a ACCase gene in a plant by the base editing method of the present invention, resulting in one or more amino acid mutaions in the ACCase which confer herbicide resistance to the plant. In some embodiments, the amino acid mutation is selected from S1768F, R1793K, A1794T, R1793K+A1794T, R1825H, D1827N, R1825H+D1827N, L1815F, A1816V, R1817Stop, L1815F+R1817Stop, A1816V+R1817Stop, L1815F+A1816V, L1815F, A1816V, +R1817Stop, A1837V, G1854D, G1855D, G1855S, G1854N, G1854D+G1855D, G1854D+G1855S, G1854D+G1855N, D1971N, D1972N, D1971N+D1972N, G1983D, P1993S, P1993L, P1993F, R1994C, P1993S+R1994C, P1993L+R1994C, P1993F+R1994C, S2003F, A2004V, T2005I, S2003F+A2004V, S2003F+T2005I, A2004V+T2005I, T2007I, A2008V, T2007I+A2008V, R2028K, W2027C, G2029D, G2029S, G2029N, R2028K+G2029D, R2028K+G2029S, R2028K+G2029N, T2047I, R2070Q, G2071R, R2070Q+G2071R, A2090T, E2091K, A2090T+E2091K, A2090V, E2106K, S2119N, R2220Q, S2119N+R2220Q, A1813V, R1793K, A1794T, R1793K+A1794T, E1796K, E1797K, E1796K+E1797K, T1800M, L1801F, T1800M+L1801F, A1813V, G1854D, G1854S, G1854N, G1855D, G1855S, G1855N, G1854D+G1855D, G1854D+G1855S, G1854D+G1855N, G1854S+G1855D, G1854S+G1855S, G1854S+G1855N, G1854N+G1855D, G1854N+G1855S, G1854N+G1855N, S1849F, H1850Y, S1849F+H1850Y, D1874N, D1875N, D1874N+D1875N, R2028K, G2029D, G2029S, G2029N, R2028K+G2029D, R2028K+G2029S, R2028K+G2029N, L2024F, T2047I, R2070C, A2090V, G1983D, E1989K, R1990Q, E1989K+R1990Q, P1993S, P1993L, P1993F, R1994C, P1993S+R1994C, P1993L+R1994C, P1993F+R1994C, T2007I, A2008V, T2007I+A2008V, S2003L, A2004V, T2005I, S2003L+A2004V, S2003L+T2005I, A2004V+T2005I, S2003L, A2004V+T2005I, L2099F, E2106K, R2220K, G2119D, R2220K+G2119D, or any combination thereof, wherein the amino acid position refers to SEQ ID NO:1 (Alopecurus myosuroides ACCase amino acid sequence, GenBank accession NO. CAC84161.1). In some embodiments, the amino acid mutation is selected from W2027C, W2027C+R2028K, wherein the amino acid position refers to SEQ ID NO:1 (Alopecurus myosuroides ACCase amino acid sequence, GenBank accession NO. CAC84161.1).

Therefore, in some embodiments, the guide RNA targets a target sequence comprising a sequence encoding amino acid(s) selected from the group consisting of S1768, R1793, A1794, R1825, D1827, L1815, A1816, R1817, A1837, G1854, G1855, D1971, D1972, G1983, P1993, R1994, S2003, A2004, T2005, T2007, A2008, R2028, G2029, T2047, R2070, G2071, A2090, E2091, E2106, S2119, R2220, A1813, E1796, E1797, T1800, L1801, S1849, H1850, D1874, D1875, L2024, E1989, R1990, L2099, or any combination thereof, wherein the amino acid position refers to SEQ ID No:1.

In some embodiments, the ACCase is rice ACCase and the wild-type sequence thereof is shown in SEQ ID No: 14 (genbank ID: B9FK36). In some embodiments, the ACCase is wheat ACCase and the wild-type sequence thereof is shown in SEQ ID No: 15 (genbank ID: ACD46684.1).

The present invention provides a method for producing a herbicide-resistant plant, comprising modifying a PPO gene in a plant by the base editing method of the present invention, resulting in one or more amino acid mutaions in the PPO which confer herbicide resistance to the plant.

The present invention provides a method for producing a herbicide-resistant plant, comprising modifying a HPPD gene in a plant by the base editing method of the present invention, resulting in one or more amino acid mutaions in HPPD which confer herbicide resistance to the plant. In some embodiments, the amino acid mutation is selected from P277S, P277L, V364M, C413Y, G414D, G414S, G414N, G415E, G415R, G415K, G414D+G415E, G414D+G415R, G414D+G415K, G414S+G415E, G414S+G415R, G414S+G415K, G414N+G415E, G414N+G415R, G414N+G415K, C413Y+G415E, C413Y+G415R, C413Y+G415K, C413Y+G414D, C413Y+G414S, C413Y+G414N, C413Y+G414D+G415E, C413Y+G414D+G415R, C413Y+G414D+G415K, C413Y+G414S+G415E, C413Y+G414S+G415R, C413Y+G414S+G415K, C413Y+G414N+G415E, C413Y+G414N+G415R, C413Y+G414N+G415K, P277S, P277L, V366I, C413Y, G414D, G414S, G414N, G415E, G415R, G415K, G414D+G415E, G414D+G415R, G414D+G415K, G414S+G415E, G414S+G415R, G414S+G415K, G414N+G415E, G414N+G415R, G414N+G415K, C413Y+G415E, C413Y+G415R, C413Y+G415K, C413Y+G414D, C413Y+G414S, C413Y+G414N, C413Y+G414D+G415E, C413Y+G414D+G415R, C413Y+G414D+G415K, C413Y+G414S+G415E, C413Y+G414S+G415R, C413Y+G414S+G415K, C413Y+G414N+G415E, C413Y+G414N+G415R, C413Y+G414N+G415K, or any combination thereof, wherein the amino acid position refers to SEQ ID NO:3 (Rice HPPD amino acid sequence, GenbankAccession NO: XP_015626163).

Thus, in some embodiments, the guide RNA targets a target sequence comprising a sequence coding amino acid(s) selected from the group consisting of P277, V364, C413, G414, G415, V366, or any combination thereof, wherein the amino acid positions refer to SEQ ID No: 3.

The design of the target sequence that can be recognized and targeted by a Cas9 and guide RNA complex is within the technical skills of one of ordinary skill in the art. In general, the target sequence is a sequence that is complementary to a leader sequence of about 20 nucleotides comprised in guide RNA, and the 3'-end of which is immediately adjacent to the protospacer adjacent motif (PAM) NGG.

For example, in some embodiments of the invention, the target sequence has the structure: 5'-$N_X$-NGG-3', wherein N is selected independently from A, G, C, and T; X is an integer of 14≤X≤30; $N_X$ represents X contiguous nucleotides, and NGG is a PAM sequence. In some specific embodiments of the invention, X is 20.

In some embodiments, the guide RNA targets one or more of SEQ ID NOs: 19-78.

The base editing system of the present invention has a broad deamination window in plants, for example, a deamination window with a length of 7 nucleotides. In some embodiments of the methods of the invention, one or more C bases within positions 3 to 9 of the target sequence are substituted with Ts. For example, if present, any one, two, three, four, five, six, or seven Cs within positions 3 to 9 in the target sequence can be replaced with Ts. For example, if there are four Cs within positions 3 to 9 of the target sequence, any one, two, three, four Cs can be replaced by Ts. The C bases may be contiguous or separated by other nucleotides. Therefore, if there are multiple Cs in the target sequence, a variety of mutation combinations can be obtained by the method of the present invention.

In some embodiments of the methods of the invention, further comprises screening plants having the desired nucleotide substitutions. Nucleotide substitutions in plants can be detected by T7EI, PCR/RE or sequencing methods, see e.g., Shan, Q., Wang, Y., Li, J. & Gao, C. Genome editing in rice and wheat using the CRISPR/Cas system. Nat. Protoc. 9, 2395-2410 (2014).

In the methods of the invention, the base editing system can be introduced into plants by various methods well known to people skilled in the art. Methods that can be used to introduce the base editing system of the present invention into plants include but not limited to particle bombardment, PEG-mediated protoplast transformation, *Agrobacterium*-mediated transformation, plant virus-mediated transformation, pollen tube approach, and ovary injection approach. In some embodiments, the base editing system is introduced into plants by transient transformation.

In the methods of the present invention, modification of the target sequence can be accomplished simply by introducing or producing the base editing fusion protein and guide RNA in plant cells, and the modification can be stably inherited without the need of stably transformation of plants with the base editing system. This avoids potential off-target effects of a stable base editing system, and also avoids the integration of exogenous nucleotide sequences into the plant genome, and thereby resulting in higher biosafety.

In some preferred embodiments, the introduction is performed in the absence of a selective pressure, thereby avoiding the integration of exogenous nucleotide sequences in the plant genome.

In some embodiments, the introduction comprises transforming the base editing system of the invention into isolated plant cells or tissues, and then regenerating the transformed plant cells or tissues into an intact plant. Preferably, the regeneration is performed in the absence of a selective pressure, i.e., no selective agent against the selective gene carried on the expression vector is used during the tissue culture. Without the use of a selective agent, the regeneration efficiency of the plant can be increased to obtain a modified plant that does not contain exogenous nucleotide sequences.

In other embodiments, the base editing system of the present invention can be transformed to a particular site on an intact plant, such as leaf, shoot tip, pollen tube, young ear, or hypocotyl. This is particularly suitable for the transformation of plants that are difficult to regenerate by tissue culture.

In some embodiments of the invention, proteins expressed in vitro and/or RNA molecules transcribed in vitro are directly transformed into the plant. The proteins and/or RNA molecules are capable of achieving base-editing in plant cells, and are subsequently degraded by the cells to avoid the integration of exogenous nucleotide sequences into the plant genome.

Thus, in some embodiments, the herbicide-resistant plant is transgene-free.

Plants that can be used in the methods of the invention include monocotyledons and dicotyledons. For example, the plant may be a crop plant such as wheat, rice, corn, soybean, sunflower, sorghum, canola, alfalfa, cotton, barley, millet, sugarcane, tomato, tobacco, tapioca, or potato. The plant may also be a vegetable crop including, but not limited to, cabbage, kale, cucumber, tomato. The plant may also be a flower crop including but not limited to carnations, peony, roses and the like. The plant may also be a fruit crop including but not limited to watermelon, melon, strawberry, blueberry, grape, apple, citrus, peach. The plant may also be a Chinese medical herbal, including but not limited to *Radix isatidis*, licorice, ginseng, and *Saposhnikovia divaricata*. The plant can also be *Arabidopsis thaliana*.

In some embodiments of the invention, the method further comprises obtaining progeny of the herbicide-resistant plant.

In another aspect, the present invention also provides a herbicide-resistant plant or progeny or parts thereof, wherein the plant is obtained by the above-described method of the present invention. In some embodiments, the herbicide-resistant plant is transgene-free.

In another aspect, the present invention also provides a plant breeding method, comprising crossing a first herbicide-resistant plant obtained by the above-described method of the present invention with a second plant having no herbicide resistance, and thereby introducing the herbicide resistance into the second plant.

The present invention also encompasses the herbicide-resistant plant or progeny thereof obtained by the method of the present invention.

IV. Identifying Variants of Herbicide Resistance Related Proteins

By the method of the present invention, a large number of mutants of herbicide resistance-related genes can be easily obtained by targeted base modification of herbicide resistance-related genes, and then novel herbicide resistance mutations can be identified through resistance screening.

Thus, the present invention also provides a method of identifying a variant of a herbicide resistance related protein that is capable of conferring herbicide resistance to a plant, said method comprising:

i) generating a herbicide-resistant plant by the method of the above Section III; and ii) determining the sequence of the herbicide resistance related gene and/or the encoded herbicide resistance related protein in the resulting herbicide resistant plant, thereby identifying the sequence of the variant.

V. Herbicide Resistance Related Protein Variants, Nucleic Acids, Expression Constructs and Uses Thereof The present invention also provides a variant of a herbicide resistance-related protein, which is identified by the method according to the above Section IV of the present invention.

The present invention also provides a plant ACCase variant, compared with wildtype ACCase, said ACCase variant comprises amino acid mutation at one of more positions selected from 1768, 1793, 1796, 1797, 1794, 1800, 1801, 1813, 1813, 1815, 1825, 1827, 1815, 1816, 1817, 1837, 1838, 1849, 1850, 1854, 1855, 1874, 1875, 1971, 1872, 1983, 1989, 1990, 1993, 1994, 2003, 2004, 2005, 2007, 2008, 2024, 2027, 2028, 2029, 2047, 2070, 2071, 2090, 2091, 2090, 2106, 2099, 2106, 2119, 2220, wherein the amino acid position refers to SEQ ID NO:1, said variant confers herbicide resistance to the plant. In some embodiments, the amino acid mutation is selected from S1768F, R1793K, A1794T, R1793K+A1794T, R1825H, D1827N, R1825H+D1827N, L1815F, A1816V, R1817Stop, L1815F+R1817Stop, A1816V+R1817Stop, L1815F+A1816V, L1815F, A1816V, +R1817Stop, A1837V, G1854D, G1855D, G1855S, G1854N, G1854D+G1855D, G1854D+G1855S, G1854D+G1855N, D1971N, D1972N, D1971N+D1972N, G1983D, P1993S, P1993L, P1993F, R1994C, P1993S+R1994C, P1993L+R1994C, P1993F+R1994C, S2003F, A2004V, T2005I, S2003F+A2004V, S2003F+T2005I, A2004V+T2005I, T2007I, A2008V, T2007I+A2008V, R2028K, G2029D, G2029S, G2029N, R2028K+G2029D, R2028K+G2029S, R2028K+G2029N, T2047I, R2070Q, G2071R, R2070Q+G2071R, A2090T, E2091K, A2090T+E2091K, A2090V, E2106K, S2119N, R2220Q, S2119N+R2220Q, A1813V, R1793K, A1794T, R1793K+A1794T, E1796K, E1797K, E1796K+E1797K, T1800M, L1801F, T1800M+L1801F, A1813V, G1854D, G1854S, G1854N, G1855D, G1855S, G1855N, G1854D+G1855D, G1854D+G1855S, G1854D+G1855N, G1854S+G1855D, G1854S+G1855S, G1854S+G1855N, G1854N+G1855D, G1854N+G1855S, G1854N+G1855N, S1849F, H1850Y, S1849F+H1850Y, D1874N, D1875N, D1874N+D1875N, W2027C, R2028K, W2027C+R2028K, G2029D, G2029S, G2029N, R2028K+G2029D, R2028K+G2029S, R2028K+G2029N, L2024F, T2047I, R2070C, A2090V, G1983D, E1989K, R1990Q, E1989K+R1990Q, P1993S, P1993L, P1993F, R1994C, P1993S+R1994C, P1993L+R1994C, P1993F+R1994C, T2007I, A2008V, T2007I+A2008V, S2003L, A2004V, T2005I, S2003L+A2004V, S2003L+T2005I, A2004V+T2005I, S2003L, A2004V+T2005I, L2099F, E2106K, R2220K, G2119D, R2220K+G2119D, or any combination thereof, wherein the amino acid position refers to SEQ ID NO:1. In some specific embodiments, the amino acid mutation is selected from W2027C, W2027C+R2028K, wherein the amino acid position refers to SEQ ID NO:1.

In some embodiments, the ACCase is rice ACCase and the wild-type sequence thereof is shown in SEQ ID No: 14 (genbank ID: B9FK36). In some embodiments, the ACCase is wheat ACCase and the wild-type sequence thereof is shown in SEQ ID No: 15 (genbank ID: ACD46684.1).

Expression of such variant enables plants (such as rice, maize, wheat and other monocotyledonous plants) to obtain single resistance (resistance to one herbicide) or cross-resistance (resistant to two or more herbicides) to cyclohexenone herbicides (such as clethodim), aryloxyphenoxypropionic acid herbicides (such as haloxyfop-P-methyl), phenylpyrazoline herbicides (such as oxazoline) and other ACCase inhibitor herbicides. The ACCase is a key enzyme in the plant's fatty acid synthetic pathway, and inhibition of its activity ultimately leads to plant death due to fatty acid deficiency.

The present invention also provides a plant ALS variant, compared with wildtype ALS, said ALSvariant comprises amino acid mutation at one of more positions selected from 122, 197, 204, 205, 653, 654, 655, 659, wherein the amino acid position refers to SEQ ID NO:2, said variant confers herbicide resistance to the plant. In some specific embodiments, the amino acid mutation is selected from A122T, P197A, P197Y, P197S, P197L, P197F, D204N, A205T, D204N+A205T, E654K, G655D, G655S, G655N, E654K+G655D, E654K+G655S, E654K+G655N, G659N, P197S, P197L, P197F, D204N, A205T, D204N+A205T, G654D, G654S, G654N, G655D, G655S, G655N, G654D+G655D, G654D+G655S, G654D+G655N, G654S+G655D, G654S+G655S, G654S+G655N, G654N+G655D, G654N+G655S, G654N+G655N, A122T, or any combination thereof, wherein the amino acid position refers to SEQ ID NO:2. In some specific embodiments, the amino acid mutation is selected from P197A, P197F, P197S, P197Y, P197F+R198C, G654E+G655S, G654K+G655S, G654E+G659N, P197F+G654E+G655S, or any combination thereof, wherein the amino acid position refers to SEQ ID NO:2.

In some embodiments, the ALS is rice ALS and its wild-type sequence is shown in SEQ ID No:16. In some embodiments, the ALS is wheat ALS and the wild-type sequence thereof is shown in SEQ ID No: 17 (partial sequence, genbank ID: AAO53548.1).

Expression of such variant can enable plants (eg, monocotyledonous plants such as rice, maize, wheat, etc., and dicots such as soybean, cotton, canola, and sunflower) to have higher levels of herbicide resistance to one or more of the following herbicides: imidazolinone herbicides (such as imazameth), sulfonylurea herbicides (such as nicosulfuron), triazolinone herbicides (such as, flucarbazone-sodium), triazolopyrimidine herbicides (eg, penoxsulam), pyrimidine salicylate herbicides (eg bispyribac-sodium). ALS is a key enzyme in the synthesis of branched-chain amino acids in plants, and inhibition of its activity ultimately results in the plant's death due to the lack of branched-chain amino acids.

The present invention also provides a plant HPPD variant, compared with wildtype HPPD, said HPPD comprises amino acid mutation at one of more positions selected from 277, 364, 366, 413, 414, 415, wherein the amino acid position refers to SEQ ID NO:3, said variant confers herbicide resistance to the plant. In some specific embodiments, the amino acid mutation is selected from P277S, P277L, V364M, C413Y, G414D, G414S, G414N, G415E, G415R, G415K, G414D+G415E, G414D+G415R, G414D+G415K, G414S+G415E, G414S+G415R, G414S+G415K, G414N+G415E, G414N+G415R, G414N+G415K, C413Y+G415E, C413Y+G415R, C413Y+G415K, C413Y+G414D, C413Y+G414S, C413Y+G414N, C413Y+G414D+G415E, C413Y+G414D+G415R, C413Y+G414D+G415K, C413Y+G414S+G415E, C413Y+G414S+G415R, C413Y+G414S+G415K, C413Y+G414N+G415E, C413Y+G414N+G415R, C413Y+G414N+G415K, P277S, P277L, V366I, C413Y, G414D, G414S, G414N, G415E, G415R, G415K, G414D+G415E, G414D+G415R, G414D+G415K, G414S+G415E, G414S+G415R, G414S+G415K, G414N+G415E, G414N+G415R, G414N+G415K, C413Y+G415E, C413Y+G415R, C413Y+G415K, C413Y+G414D, C413Y+G414S, C413Y+G414N, C413Y+G414D+G415E, C413Y+G414D+G415R, C413Y+G414D+G415K, C413Y+G414S+G415E, C413Y+G414S+G415R, C413Y+G414S+G415K, C413Y+G414N+G415E, C413Y+G414N+G415R, C413Y+G414N+G415K, or any combination thereof.

In some embodiments, the HPPD is rice HPPD, and the wild-type sequence thereof is shown in SEQ ID No:3. In some embodiments, the HPPD is wheat HPPD, and the wild-type sequence thereof is shown in SEQ ID No:18.

Expression of such variant can enable plants (eg, monocotyledonous plants such as rice, maize, wheat, etc., dicots such as soybean, cotton, rapeseed, sunflower, etc.) to obtain higher level of resistance to one or more HPPD inhibitor herbicides (eg, mesotrione, topramezone). HPPD is a key enzyme of chlorophyll synthesis pathway in plants. Inhibition of the activity of HPPD ultimately leads to the chlorosis and death of plants.

The present invention also provides a plant EPSPS variant, compared with wildtype EPSPS, said EPSPS comprises amino acid mutation at one of more positions selected from 102 and 103, wherein the amino acid position refers to SEQ ID NO:4, said variant confers herbicide resistance to the plant. In some embodiments, the amino acid mutation is selected from the group consisting of T102I, A103V, T102I+A103V. The EPSPS enzyme is a key enzyme in the synthesis of aromatic amino acids in plants, and inhibition of its activity ultimately leads to the plant's death due to the lack of aromatic amino acids.

In some embodiments, the EPSPS is wheat EPSPS, and its wild-type sequence is shown in SEQ ID No:4.

The expression of such variant can significantly increase the resistance to glyphosate in plants (eg, monocotyledons such as rice, maize, wheat, etc., and dicotyledons such as soybean, cotton, rapeseed, and sunflower).

In some embodiments, the variants of the present invention also comprise other amino acid mutations known in the art that are capable of conferring herbicide resistance to the plant.

The invention also provides an isolated nucleic acid comprising a nucleotide sequence encoding a variant of the invention.

The invention also provides an expression cassette comprising a nucleotide sequence encoding a variant of the invention operably linked to a regulatory sequence.

The invention also provides an expression construct comprising a nucleotide sequence encoding a variant of the invention, said nucleotide sequence operably linked to a regulatory sequence.

The invention also provides use of the variants, the isolated nucleic acids, expression cassettes and expression constructs of the invention in the generation of herbicide-resistant plants.

The present invention also provides a method of producing a herbicide-resistant plant, comprising introducing the isolated nucleic acid of the present invention, the expression cassette of the present invention, and/or the expression construct of the present invention into a plant.

The invention also provides a herbicide-resistant plant that comprises or is transformed by an expression cassette of the invention. The present invention also covers the progeny of the herbicide-resistant plants.

The plants include monocotyledons and dicotyledons. For example, the plant may be a crop plant such as wheat, rice, corn, soybean, sunflower, sorghum, canola, alfalfa, cotton, barley, millet, sugarcane, tomato, tobacco, tapioca, or potato. The plant may also be a vegetable crop including, but not limited to, cabbage, kale, cucumber, tomato. The plant may also be a flower crop including but not limited to carnations, peony, roses and the like. The plant may also be a fruit crop including but not limited to watermelon, melon, strawberry, blueberry, grape, apple, citrus, peach. The plant may also be a Chinese medical herbal, including but not limited to *Radix isatidis*, licorice, ginseng, and *Saposhnikovia divaricata*. The plant can also be *Arabidopsis thaliana*.

EXAMPLE

Example 1. Construction of Base Editing Vectors

In this example, base editing vectors for herbicide resistance-related genes such as ALS, ACCase, EPSPS, and HPPD for different crops were constructed.

Rice:

According to Yuan Zong (Zong, Y. et al. Precise base editing in rice, wheat and maize with a Cas9-cytidine deaminase fusion. Nat. Biotechnol. 2017, doi: 10.1038/nbt.3811), base editing vectors targeting OsALS, OsACCase, and OsHPPD genes were constructed using pH-nCas9-PBE construct. Among them, 4 target single sites in OsALS (R1-R4), 3 target double sites of OsALS gene (R25-R27), and 20 target single sites of OsACCase gene (R5-R24), 4 target single sites of OsHPPD (R28-R30). The sgRNA target sequences in the experiment are shown in Table 1. Potential resistance mutations are shown in Table 3.

TABLE 1

Rice ALS gene and sgRNA target sequences

| | Targeted gene | target sequence | SEQ ID NO: |
|---|---|---|---|
| R1 | OsALS | CCTACCCGGGCGGCGCGTCCATG | 19 |
| R2 | OsALS | CAGGTCCCCCGCCGCATGATCGG | 20 |
| R3 | OsALS | CCGCATGATCGGCACCGACGCCT | 21 |
| R4 | OsALS | CCTATGATCCCAAGTGGGGCGC | 22 |
| R5 | OsACCase | TATTGATTCTGTTGTGGGCAAGG | 23 |
| R6 | OsACCase | CCAGTGCTTATrCTAGGGCATAT | 24 |
| R7 | OsACCase | CCGGTGCATACAGCGTCTTGACC | 25 |
| R8 | OsACCase | ATCTTGCTCGACTTGGCATCCGG | 26 |
| R9 | OsACCase | TCTGCACTGAACAAGCTTCTTGG | 27 |
| R10 | OsACCase | CCACATGCAGTTGGGTGGTCCCA | 28 |
| R11 | OsACCase | CCATCTTACTGTTTCAGATGACC | 29 |
| R12 | OsACCase | CCCTGCTGACCCTGGTCAGCTTG | 30 |
| R13 | OsACCase | TTCCTCGTGCTGGACAAGTGTGG | 33 |
| R14 | OsACCase | TTCTGCAACCAAGACTGCGCAGG | 32 |
| R15 | OsACCase | CAAGACTGCGCAGGCATTGCTGG | 33 |
| R16 | OsACCase | CCTCGCTAACTGGAGAGGCTTCT | 34 |
| R17 | OsACCase | CGACTATTGTTGAGAACCTTAGG | 35 |
| R18 | OsACCase | CCATGGCTGCAGAGCTACGAGGA | 36 |
| R19 | OsACCase | CCGCATTGAGTGCTATGCTGAGA | 37 |
| R20 | OsACCase | TATGCTGAGAGGACTGCAAAAGG | 38 |
| R21 | OsACCase | CCGCAAGGGTTAATTGAGATCAA | 39 |
| R22 | OsACCase | GCAATGTTCTGGAACCGCAAGGG | 40 |
| R23 | OsACCase | CCAGGATTGCATGAGTCGGCTTG | 41 |
| R24 | OsACCase | GGAGCTTATCTTGCTCGACTTGG | 42 |
| R25 | OsALS | CAGGTCCCCCGCCGCATGATCGG CCTACCCGGGCGGCGCGTCCATG | 43 |

TABLE 1-continued

Rice ALS gene and sgRNA target sequences

| Targeted | gene | target sequence | SEQ ID NO: |
|---|---|---|---|
| R26 | OsALS | CAGGTCCCCCGCCGCATGATCGG CCGCATGATCGGCACCGACGCCT | 44 |
| R27 | OsALS | CAGGTCCCCCGCCGCATGATCGG CCTATGATCCCAAGTGGGGCGC | 45 |
| R28 | OsHPPD | GCTGCTGCCGCTCAACGAGCCGG | 46 |
| R29 | OsHPPD | CCAGGAGCTCGGGGTGCTCGTGG | 47 |
| R30 | OsHPPD | CCAGAAGGGCGGCTGCGGCGGGT | 48 |

PAM was underlined

Wheat:

According to Yuan Zong (Zong, Y. et al. Precise base editing in rice, wheat and maize with a Cas9-cytidine deaminase fusion. Nat. Biotechnol. 2017, doi:10.1038/nbt.3811), base editing vectors targeting TaALS, TaACCase, TaEPSPS and TaHPPD gene were constructed using pTaU6. Among them, 4 target single sites in TaALS gene (W1-W3, W16), 3 target double sites in TaALS gene (W31-W33), 20 target single sites of TaACCase gene (W4-W15, W17-W24), 3 target single sites of TaEPSPS gene (W25-W27) and 3 target single sites of TaHPPD gene (W28-W30), and 1 targets double-sites of TaALS and TaACCase genes simultaneously (W34). The sgRNA target sequences in the experiment are shown in Table 2. Potential resistance mutations are shown in Table 4.

TABLE 2

Wheat target genes and sgRNA target sequences

| Targeted | gene | target sequence | SEQ ID NO: |
|---|---|---|---|
| W1 | TaALS | CAGGTCCCCCGCCGCATGATCGG | 49 |
| W2 | TaALS | CCGCATGATCGGCACGGACGCGT | 50 |
| W3 | TAALSS | CCTATGATCCCAAGCGGTGGTGC | 51 |
| W4 | TaACCase | CCAGTGCCTATTCTAGGGCCTAT | 52 |
| W5 | TaACCase | CCTATTCTAGGGCCTATGAGGAG | 53 |
| W6 | TaACCase | TTTACGCTTACATTTGTGACTGG | 54 |
| W7 | TaACCase | GGAGCATATCTTGCTCGACTTGG | 55 |
| W8 | TaACCase | CCCACATGCAGTTGGGTGGCCCC | 56 |

TABLE 2-continued

Wheat target genes and sgRNA target sequences

| Targeted | gene | target sequence | SEQ ID NO: |
|---|---|---|---|
| W9 | TaACCase | AGCTCCCACATGCAGTTGGGTGG | 57 |
| W10 | TaACCase | CCATCTGACAGTTTCAGATGACC | 58 |
| W11 | TaACCase | CCTTGCTAACTGGAGAGGCTTCT | 59 |
| W12 | TaACCase | TTCATCCTTGCTAACTGGAGAGG | 60 |
| W13 | TaACCase | CAACAATTGTTGAGAACCTTAGG | 61 |
| W14 | TaACCase | AGAGCTACGTGGAGGGGCTTGGG | 62 |
| W15 | TaACCase | TATGCTGAGAGGACTGCAAAGGG | 63 |
| W16 | TaALS | CCTACCCTGGCGGCGCGTCCATG | 64 |
| W17 | TaACCase | CCCTGCTGATCCAGGCCAGCTTG | 65 |
| W18 | TaACCase | CCAGCTTGATTCCCATGAGCGGT | 66 |
| W19 | TaACCase | TTCCTCGTGCTGGGCAAGTCTGG | 67 |
| W20 | TaACCase | TAAGACAGCGCAGGCAATGCTGG | 68 |
| W21 | TaACCase | TTCAGCTACTAAGACAGCGCAGG | 69 |
| W22 | TaACCase | GTAATGTTCTTGAACCTCAAGGG | 70 |
| W23 | TaACCase | CCTCAAGGGTTGATTGAGATCAA | 71 |
| W24 | TaACCase | CCAAGAGTGCATGGGCAGGCTTG | 72 |
| W25 | TaEPSPS | AACTGCAATGCGGCCACTGACGG | 73 |
| W26 | TaEPSPS | AACTGCAATGCGTCCATTGACGG | 74 |
| W27 | TaEPSPS | AACTGCAATGCGGCCATTGACGG | 75 |
| W28 | TaHPPD | GCTGCTGCCGCTCAACGAGCCGG | 76 |
| W29 | TaHPPD | CCAGGAGCTGGGGGTGCTCGTCG | 77 |
| W30 | TaHPPD | CCAGAAGGGTGGCTGCGGCGGGT | 78 |
| W31 | TaALS | CAGGTCCCCCGCCGCATGATCGG CCTACCCTGGCGGCGCGTCCATG | 89 |
| W32 | TaALS | CAGGTCCCCCGCCGCATGATCGG CCGCATGATCGGCACGGACGCGT | 90 |
| W33 | TaALS | CAGGTCCCCCGCCGCATGATCGG CCTATGATCCCAAGCGGTGGTGC | 91 |
| W34 | TaALS TaACCase | CAGGTCCCCCGCCGCATGATCGG TTCAGCTACTAAGACAGCGCAGG | 92 |

PAM was underlined

TABLE 3

Potential herbicide resistance mutations in rice.

| Rice | Targeted gene | target sequence | SEQ ID NO: | mutations |
|---|---|---|---|---|
| R1 | OsALS | CCTACCCGGGCGGCGCGTCCATG | 19 | A122T |
| R2 | OsALS | CAGGTCCCCCGCCGCATGATCGG | 20 | P197S P197L P197F |

TABLE 3-continued

Potential herbicide resistance mutations in rice.

| Rice | Targeted gene | target sequence | SEQ ID NO: | mutations |
|---|---|---|---|---|
| R3 | OsALS | CCGCATGATCGGCACCGACGCCT | 21 | D204N A205T<br>D204N and A205T |
| R4 | OsALS | CCTATGATCCCAAGTGGGGCGC | 22 | G654K G655D<br>G655S G655N<br>G654K and G655D<br>G654K and G655S<br>G654K and G655N |
| R5 | OsACCase | TATTGATTCTGTTGTGGGCAAGG | 23 | S1768F |
| R6 | OsACCase | CCAGTGCTTATTCTAGGGCATAT | 24 | R1793K A1794T<br>R1793K and A1794T |
| R7 | OsACCase | CCGGTGCATACAGCGTCTTGACC | 25 | R1825H D1827N<br>R1825H and D1827N |
| R8 | OsACCase | ATCTTGCTCGACTTGGCATCCGG | 26 | L1815F A1816V<br>R1817Stop<br>L1815F and R1817Stop<br>A1816V and R1817Stop<br>L1815F and A1816V<br>L1815F, A1816V, and R1817Stop |
| R9 | OsACCase | TCTGCACTGAACAAGCTTCTTGG | 27 | A1837V |
| R10 | OsACCase | CCACATGCAGTTGGGTGGTCCCA | 28 | G1854D G1855D<br>G1855S G1854N<br>G1854D and G1855D<br>G1854D and G1855S<br>G1854D and G3855N |
| R11 | OsACCase | CCATCTTACTGTTTCAGATGACC | 29 | D1971N D1972N<br>D1971N and D1972N |
| R12 | OsACCase | CCCTGCTGACCCTGGTCAGCTTG | 30 | G1983D |
| R13 | OsACCase | TTCCTCGTGCTGGACAAGTGTGG | 31 | P1993S P1993L<br>P3993F R1994C<br>P1993S and R1994C<br>P1993L and R1994C<br>P1993F and R1994C |
| R14 | OsACCase | TTCTGCAACCAAGACTGCGCAGG | 32 | S2003F A2004V<br>T2005I<br>S2003F and A2004V<br>S2003F and T2005I<br>A2004V and T2005I |
| R15 | OsACCase | CAAGACTGCGCAGGCATTGCTGG | 33 | T2007I A2008V<br>T2007I and A2008V |
| R16 | OsACCase | CCTCGCTAACTGGAGAGGCTTCT | 34 | R2028K G2029D<br>G2029S G2029N<br>R2028K and G2029D<br>R2028K and G2029S<br>R2028K and G2029N |
| R17 | OsACCase | CGACTATTGTTGAGAACCTTAGG | 35 | T2047I |
| R18 | OsACCase | CCATGGCTGCAGAGCTACGAGGA | 36 | R2070Q G2071R<br>R2070Q and G2071R |
| R19 | OsACCase | CCGCATTGAGTGCTATGCTGAGA | 37 | A2090T E2091K<br>A2090T and E2091K |
| R20 | OsACCase | TATGCTGAGAGGACTGCAAAAGG | 38 | A2090V |
| R21 | OsACCase | CCGCAAGGGTTAATTGAGATCAA | 39 | E2106K |

TABLE 3-continued

Potential herbicide resistance mutations in rice.

| Rice | Targeted gene | target sequence | SEQ ID NO: | mutations |
|---|---|---|---|---|
| R22 | OsACCase | GCAATGTTCTGGAACCGCAAGGG | 40 | — |
| R23 | OsACCase | CCAGGATTGCATGAGTCGGCTTG | 41 | S2119N R2220Q<br>S2119N and R2220Q |
| R24 | OsACCase | GGAGCTTATCTTGCTCGACTTGG | 42 | A1813V |
| R25 | OsALS | CAGGTCCCCCGCCGCATGATCGG<br>CCTACCCGGGCGGCGCGTCCATG | 43 | R2 + R1 |
| R26 | OsALS | CAGGTCCCCCGCCGCATGATCGG<br>CCGCATGATCGGCACCGACGCCT | 44 | R2 + R3 |
| R27 | OsALS | CAGGTCCCCCGCCGCATGATCGG<br>CCTATGATCCCAAGTGGGGCGC | 45 | R2 + R4 |
| R28 | OsHPPD | GCTGCTGCCGCTCAACGAGCCGG | 46 | P277S P277L |
| R29 | OsHPPD | CCAGGAGCTCGGGGTGCTCGTGG | 47 | V364M |
| R30 | OsHPPD | CCAGAAGGGCGGCTGCGGCGGGT | 48 | C413Y G414D<br>G414S G414N<br>G415E G415R<br>G415K<br>G414D and G415E<br>G414D and G415R<br>G414D and G435K<br>G414S and G41SE<br>G414S and G415R<br>G414S and G415K<br>G414N and G415E<br>G414N and G415R<br>G414N and G415K<br>C413Y and G415E<br>C413Y and G415R<br>C413Y and G415K<br>C413Y and G414D<br>C413Y and G414S<br>C413Y and G414N<br>C413Y, G414D and G415E,<br>C413Y, G414D and G415R<br>C413Y, G414D and G415K,<br>C413Y, G414S and G415E<br>C413Y, G4I4S and G415R<br>C413Y, G414S and G415K<br>C413Y, G414N and G41SE<br>C413Y, G414N and G415R<br>C413Y, G414N and G415K |

TABLE 4

Potential herbicide resistance mutations in wheat.

| Wheatgene | Targeted gene | target sequence | SEQ ID NO: | mutations |
|---|---|---|---|---|
| W1 | TaALS | CAGGTCCCCCGCCGCATGATCGG | 93 | P197S P197L<br>P197F |
| W2 | TaALS | CCGCATGATCGGCACGGACGCGT | 50 | D204N A205T<br>D204N and A205T |

TABLE 4-continued

Potential herbicide resistance mutations in wheat.

| Wheat | Targeted gene | target sequence | SEQ ID NO: | mutations |
|---|---|---|---|---|
| W3 | TaALS | CCTATGATCCCAAGCGGTGGTGC | 51 | G654D G654S<br>G654N G655D<br>G655S G655N<br>G654D and G655D<br>G654D and G655S<br>G654D and G655N<br>G654S and G655D<br>G654S and G655S<br>G654S and G655N<br>G654N and G655D<br>G654N and G655S<br>G654N and G655N |
| W4 | TaACCase | CCAGTGCCTATTCTAGGGCCTAT | 52 | R1793K A3794T<br>R1793K and A1794T |
| W5 | TaACCase | CCTATTCTAGGGCCTATGAGGAG | 53 | E1796K E1797K<br>E1796K and E1797K |
| W6 | TaACCase | TTTACGCTTACATTTGTGACTGG | 54 | T1800M L1801F<br>T1800M and L1801F |
| W7 | TaACCase | GGAGCATATCTTGCTCGACTTGG | 55 | A1833V |
| W8 | TaACCase | CCCACATGCAGTTGGGTGGCCCC | 56 | G1854D G1854S<br>G1854N G1855D<br>G1855S G1855N<br>G1854D and G1855D<br>G1854D and G1855S<br>G1854D and G1855N<br>G1854S and G1855D<br>G3854S and G1855S<br>G3854S and G1855N<br>G1854N and G1855D<br>G1854N and G1855S<br>G1854N and G1855N |
| W9 | TaACCase | AGCTCCCACATGCAGTTGGGTGG | 57 | S1849F H1850Y<br>S1849F and H1850Y |
| W10 | TaACCase | CCATCTGACAGTTTCAGATGACC | 58 | D1874N D1875N<br>D3874N and D1875N |
| W11 | TaACCase | CCTTGCTAACTGGAGAGGCTTCT | 59 | R2028K G2029D<br>G2029S G2029N<br>R2028K and G2029D<br>R2028K and G2029S<br>R2028K and G2029N |
| W12 | TaACCase | TTCATCCTTGCTAACTGGAGAGG | 60 | L2024F |
| W13 | TaACCase | CAACAATTGTTGAGAACCTTAGG | 61 | T2047I |
| W14 | TaACCase | AGAGCTACGTGGAGGGGCTTGGG | 62 | R2070C |
| W15 | TaACCase | TATGCTGAGAGGACTGCAAAGGG | 63 | A2090V |
| W16 | TaALS | CCTACCCTGGCGGCGCGTCCATG | 64 | A122T |
| W17 | TaACCase | CCCTGCTGATCCAGGCCAGCTTG | 65 | G19830 |
| W18 | TaACCase | CCAGCTTGATTCCCATGAGCGGT | 66 | E1989K R1990Q<br>E1989K and R1990Q |
| W19 | TaACCase | TTCCTCGTGCTGGGCAAGTCTGG | 67 | P1993S P1993L<br>P1993F R1994C<br>P1993S and R1994C<br>P1993L and R1994C<br>P1993F and R1994C |
| W20 | TaACCase | TAAGACAGCGCAGGCAATGCTGG | 68 | T2007I A2008V<br>T2007I and A2008V |

TABLE 4-continued

Potential herbicide resistance mutations in wheat.

| Wheat | Targeted gene | target sequence | SEQ ID NO: | mutations |
|---|---|---|---|---|
| W21 | TaACCase | TTCAGCTACTAAGACAGCGCAGG | 69 | S2003E A2004V T2005I<br>S2003L and A2004V<br>S2003L and T2005I<br>A2004V and T2005I<br>S2003L, A2004V and T2005I |
| W22 | TaACCase | GTAATGTTCTTGAACCTCAAGGG | 70 | L2099F |
| W23 | TaACCase | CCTCAAGGGTTGATTGAGATCAA | 71 | E2106K |
| W24 | TaACCase | CCAAGAGTGCATGGGCAGGCTTG | 72 | R2220K G2119D<br>R2220K and G2119D |
| W25 | TaEPSPS | AACTGCAATGCGGCCACTGACGG | 73 | T102I A103V<br>T102I and A103V |
| W26 | TaEPSPS | AACTGCAATGCGTCCATTGACGG | 74 | T102I A103V<br>T102I and A103V |
| W27 | TaEPSPS | AACTGCAATGCGGCCATTGACGG | 75 | T102I A103V<br>T102I and A103V |
| W28 | TaHPPD | GCTGCTGCCGCTCAACGAGCCGG | 46 | P277S P277L |
| W29 | TaHPPD | CCAGGAGCTGGGGGTGCTCGTCG | 77 | V366I |
| W30 | TaHPPD | CCAGAAGGGTGGCTGCGGCGGGT | 78 | C413Y G414D<br>G414S G414N<br>G415E G415R<br>G415K<br>G414D and G415E<br>G414D and G415R<br>G414D and G415K<br>G414S and G415E<br>G414S and G415R<br>G414S and G415K<br>G414N and G415E<br>G414N and G415R<br>G414N and G415K<br>C413Y and G415E<br>C413Y and G415R<br>C413Y and G415K<br>C413Y and G414D<br>C413Y and G414S<br>C413Y and G414N<br>C413Y, G414D and G415E<br>C413Y, G414D and G415R<br>C413Y, G414D and G415K<br>C413Y, G414S and G415E<br>C413Y, G414S and G415R<br>C413Y, G414S and G415K<br>C413Y, G414N and G415E<br>C413Y, G414N and G415R<br>C413Y, G414N and G415K |
| W31 | TaALS | CAGGTCCCCCGCCGCATGATCGG CCTACCCTGGCGGCGCGTCCATG | 89 | W2 + W1 |
| W32 | TaALS | CAGGTCCCCCGCCGCATGATCGG CCGCATGATCGGCACGGACGCGT | 90 | W2 + W3 |
| W33 | TaALS | CAGGTCCCCCGCCGCATGATCGG CCTATGATCCCAAGCGGTGGTGC | 91 | W2 + W4 |

TABLE 4-continued

Potential herbicide resistance mutations in wheat.

| Wheatgene | Targeted target sequence | SEQ ID NO: | mutations |
|---|---|---|---|
| W34 | TaALS CAGGTCCCCCGCCGCATGATCGG<br>TaACCase TTCAGCTACTAAGACAGCGCAGG | 92 | W2 + W21 |

Example 2. Rice and Wheat Transformation

Rice (*Agrobacterium* Transformation):

The pH-nCas9-PBE vectors were transformed into *Agrobacterium* strain AGL1 by electroporation. *Agrobacterium*-mediated transformation, tissue culture and regeneration of Zhonghua 11 were performed according to Shan et al. (Shan, Q. et al. Targeted genome modification of crop plants using a CRISPR-Cas system. Nat. Biotechnol. 31, 686-688 (2013)). Hygromycin selection (50 μg/ml) was used during all subsequent tissue cultures.

Wheat (Particle Bombardment Transformation):

Plasmid DNA (pnCas9-PBE and pTaU6 vectors were mixed in equal, respectively) was used to bombard the embryos of Kenong 199, as previously described (Zhang, K., Liu, J., Zhang, Y., Yang, Z. & Gao, C. Biolistic genetic transformation of a wide range of Chinese elite wheat (*Triticum aestivum* L.) varieties. J. Genet Genomics. 42, 39-42 (2015)). After bombardment, embryos were processed according to Zhang, K. et. al., but no selective agent was used during tissue culture.

Example 3. Establishing Resistance Screening Conditions for Transformed Plants Herbicides listed in Table 5 were selected, and ½ MS medium containing different concentrations of herbicides was prepared for screening wild type rice and wheat tissue culture seedlings. After 7 days, the minimum herbicide concentrations inhibiting plant growth were selected for subsequent screen of transformed plants.

TABLE 5

Herbicides used for screen

| Herbicides | Inhibited gene | Selection concentration for rice (PPM) | Selection concentration for wheat (PPM) |
|---|---|---|---|
| Imazameth | ALS | | |
| Nicosulfuron | ALS | 0.012 | 0.13 |
| Pyroxsulam | ALS | | |
| Flucarbazone-sodium | ALS | | |
| Bispyribac-sodium | ALS | | |
| fenoxaprop-P-ethyl | ACCase | 4.5 | |
| cyhalofop-butyl | ACCase | 5.3 | |
| sethoxydim | ACCase | 0.33 | 0.33 |
| PINOXADEN | ACCase | | |
| Haloxyfop-R-methyl | ACCase | 0.036 | 0.036 |
| mesotrione | HPPD | | |
| Glyphosate | EPSPS | | |

Example 4. Screening and Identification of Resistant Plants

Figure 2:
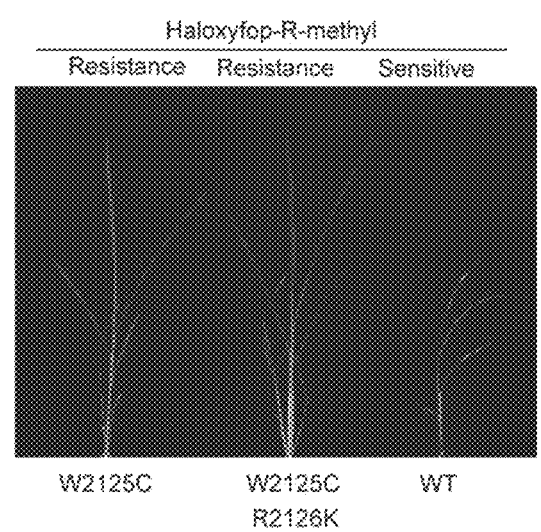
FIG. 2. shows the screening of resistant mutations in rice ACCase.
Figure 3:
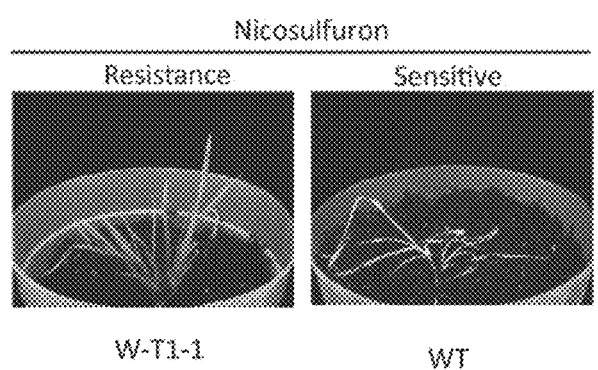
FIG. 3. shows the screening of resistant mutations in wheat ALS.

The transformed plants obtained in Example 3 were grown on the corresponding herbicide screening medium (Table 5) and the phenotypes were observed and the resistant plants were selected (FIGS. 1-3).

After extracting the DNA of resistant plants, T7EI and PCR/RE were perforemd. Finally, the mutations of the target genes were confirmed by Sanger sequencing.

As a result, the following mutations in plant-endogenous proteins ALS and ACCase were identified as herbicide-resistant mutations. In addition to C-T mutations, the base editing system of the present invention may also cause C-G/A mutations, so unexpected resistant mutations were screened out.

TABLE 6

Rice ALS resistant mutations.

| Amino acid position | resistant substitution | Nicosulfuron | Pyroxsulam | Flucarbazone-sodium | Bispyribac-sodium | Imazameth |
|---|---|---|---|---|---|---|
| OsALS-P171 | A | R | R | R | r | |
| (corresponding to AtALS-P197) | F | R | R | R | R | |
| | S | R | R | R | R | |
| | Y | R | R | R | R | |
| OsALS-P171, R172 (corresponding to AtALS-P197, R198) | F, C | R | R | R | R | |
| OsALS-G628, G629 (corresponding to AtALS-G654, G655) | E, S | | | | | R |
| OsALS-G628, G629 (corresponding to AtALS-G654, G655) | K, S | | | | | R |
| OsALS-G628, D633 (corresponding to AtALS-G654, D659) | E, N | | | | | R |
| OsALS-P171, G628, G629 (corresponding to AtALS-P197, G654, G655) | F, E, S | R | R | R | R | |

TABLE 7

Rice ACCase resistant mutations

| Amino acid position | resistant substitution | Haloxyfop-R-methyl |
|---|---|---|
| OsACCase-W2125 (corresponding to AtACCase-W2027) | C | R |
| OsACCase-W2125, R2126 (corresponding to AtACCase-W2027, R2028) | C, K | R |

TABLE 8

Nicosulfuron resistant mutations in wheat

| Amino acid position | A genome substitution | B genome substitution | D genome substitution |
|---|---|---|---|
| TaALS-P173 (corresponding to AtALS-P197) | F(homo) | S(homo) | S(homo) |
| | F(homo) | F(homo) | S(homo) |
| | S(homo) | F/S | F/S |
| | F(homo) | F/S | F/S |
| | F/S | F/S | F/S |
| | F/A | F(homo) | F/S |
| | F/S | F(homo) | F/S |

SEQUENCE LISTING

```
Alopecurus myosuroides ACCase amino acid sequence
                                                              SEQ ID NO: 1
MGSTHLPIVGFNASTTPSLSTLRQINSAAAAFQSSSPSRSSKKKSRRVKSIRDDGDGSVPDPAGHGQSIRQGLA
GIIDLPKEGASAPDVDISHGSEDHKASYQMNIGLNESHNGRHASLSKVYEFCTELGGKTPIHSVLVANNGMAAA
KFMRSVRTWANDTFGSEKAIQLIAMATPEDMRINAEHIRIADQFVEVPGGTNNNNYANVQLIVEIAERTGVSAV
WPGWGHASENPELPDALTAKGIVFLGPPASSMNALGDKVGSALIAQAAGVPTLAWSGSHVEIPLELCLDSIPEE
MYRKACVTTADEAVASCQMIGYPAMIKASWGGGGKGIRKVNNDDEVKALFKQVQGEVPGSPIFIMRLASQSRHL
EVQILCDEYGNVAALHSRDCSVQRRHQKIIEEGPVTVAPRETVKELEQAARRLAKAVGYVGAATVEYLYSMETG
EYYFLELNPRLQVEHPVTESINEVNLPAAQVAVGMGIPLWQIPEIRRFYGMDNGGGYDIWRKTAALATPFNFDE
VDSQWPKGHCVAVRITSENPDDGFKPTGGKVKEISFKSKPNVWGYFSVKSGGGIHEFADSQFGHVFAYGETRSA
AITSMSLALKEIQIRGEIHTNVDYTVDLLNAPDFRENTIHTGWLDTRIAMRVQAERPPWYISVVGGALYKTITT
NAETVSEYVSYLIKGQIPPKEISLVHSTISLNIFESKYTIFIVRSGQGSYRLRLNGSLIEANVQTLCDGGLLMQ
LDGNSHVIYAEEEAGGTRLLIDGKTCLLQNDHDPSRLLAETPCKLLRFLIADGAHVDADVPYAEVEVMKMCMPL
LSPAAGVINVLLSEGQAMQAGDLIARLDLDDPSAVKPAFPFEGSFPFMSLPIAASGQWlKRCAASLNAARMVLA
GYDHAANKVVQDLVWCLDTPALPFLQWEFLMSVLATRLPRRLKSELEGKYNEYKLNVDHVKIKDFPTEMLRETI
EENLACVSEKEMVTIERLVDPLMSLLKSYEGGRESHAHFIVKSLFEEYLSVEELFSDGIQSDVIERLRLQYSKD
LQKVVDIVLSHQGVRNKTKLILALMEKINYPNPAAYRDQLIRFSSLNHKRYYKLALKASELLEQTKLSELRTSI
ARNLSALDMFTEEKADFSLQDRKLAINESMGDLVTAPLPVEDALVSLFDCTDQTLQQRVIQTYISRLYQPQINK
DSIQLKYQDSGVIALWEFTEGNHEKRLGAMVILKSLESVSTAIGAALKDASHYASSAGNTVHIALLDADTQLNT
TEDSGDNDQAQDKMDKLSFVLKQDVVMADLRAADVKVVSCIVQRDGAIMPMRRTFLLSEEKLCYEEEPILRHVE
PPLSALLELDKLKVKGYNEMKYTPSRDRQWHIYTLRNTENPKMLHRVFFRTLVRQPSAGNRFTSDHITDVEVGH
AEEPLSFTSSSILKSLKIAKEELELHAIRTGHSHMYLCILKEQKLLDLVPVSGNTVVDVGQDFATACSLLKEMA
LKIHELVGARMHHLSVCQWEVKLKLVSDGPASGSWRVVTTNVTGHTCTVDIYREVEDTESQKLVYHSTALSSGP
LHGVALNTSYQPLSVIDLKRCSARNNKTTYCYDFPLTFEAAVQKSWSNISSENNQCYVKATELVFAEKNGSWGT
PIIPMQRAAGLNDIGMVAWILDMSTPEFPSGRQIIVIANDITFRAGSFGPREDAFFEAVTNLACEKKLPLIYLA
ANSGARIGIADEVKSCFRVGWTDDSSPERGFRYIYMTDEDHDRIGSSVIAEKMQLDSGEIRWVIDSVVGKEDGL
GVENIHGSAAIASAYSRAYEETFTLTFVTGRTVGIGAYLARLGIRCIQRIDQPIILTGFSALNKLLGREVYSSH
MQLGGPKIMATNGVVHLTVPDDLEGVSNILRWLSYVPANIGGPLPITKSLDPIDRPVAYIPENTCDPRAAISGI
DDSQGKWLGGMFDKDSFVETFEGWAKTVVTGRAKLGGIPVGVIAVETQTMMQLVPADPGQPDSHERSVPRAGQV
WFPDSATKTAQAMLDFNREGLPLFILANWRGFSGGQRDLFEGILQAGSTIVENLRTYNQPAFVYTPKAAELRGG
AWVVIDSKINPDRIECYAERTAKGNVLEPQGLIEIKERSEELKECMGRLDPELIDLKARLQGANGSLSDGESLQ
KSIEARKKQLLPLYTQIAVRFAELHDTSLRMAAKGVIRKVVDWEDSRSFFYKRLRRRLSEDVLAKEIRGVIGEK
```

```
FPHKSAIELIKKWYLASEAAAAGSTDWDDDDAEVAWRENPENYKEYIKELRAQRVSRLLSDVAGSSSDLQALPQ

GLSMLLDKMDPSKRAQFIEEVMKVLK
```

*Arobidopsis* ALS amino acid sequence

SEQ ID NO: 2

```
MAAATTTTTSSSISFSTKPSPSSSKSPLPISRFSLPFSLNPNKSSSSSRRRGIKSSSPSSISAVLNTTTNVTT

TPSPTKPTKPETFISRFAPDQPRKGADILVEALERQGVETVFAYPGGASMEIHQALTRSSSIRNVLPRHEQGGV

FAAEGYARSSGKPGICIATSGPGATNLVSGLADALLDSVPLVAITGQVPRRMIGTDAFQETPIVEVTRSITKHN

YTLMDVEDIPRIIEFAFFLATSGRPGPVLVDVPKDIQQQLAIPNWEQAMRLPGYMSRMPKPPFDSHLEQIVRLI

SESKKPVLYVGGGCLNSSDELGRFVELTGIPVASTLMGLGSYPCDDELSHMLGMHGTVYANYAVEHSDLLLAF

GVRFDDRVTGKLEAFASRAKIVHIDIDSAEIGKNKTPHVSVCGDVKLALQGMNKVLENRAEELKLDFGVWRNEL

NVQKQKFPLSFKTFGEAIPPQYAIKVLDELTDGKAIISTGVGQHQMWAAQFYNYKKPRQWLSSGGLGAMGFGLP

AAIGASVANPDAIVVDIDGDGSFIMNVQELATIRVENLPVKVLLLNNQHLGMVMQWEDRFYKANRASTFLGDPA

QEDEIFPNMLLFAAACGIPAARVTKKADLR.EAIQTMLDTPGPYLLDVICPHQEHVLPMIPSGGTFNDVITEGD

GRIKY
``` rice HPPD amino acid sequence

SEQ ID NO: 3

```
MPPTPTPTATTGAVSAAAAAGENAGFRLVGHRRFVRANPRSDRFQALAFHHVELWCADAASAAGRFAFALGAPL

AARSDLSTGNSAHASLLLRSASVAFLFTAPYGGDHGVGADAATTASIPSFSPGAARRFAADHGLAVHAVALRVA

DAADAFRASVAAGARPAFQPADLGGGFGLAEVELYGDVVLRFVSHPDGADAPFLPGFEGVSNPGAVDYGLRRED

HVVGNVPELAPVAAYISGFTGFHEFAEFTAEDVGTAESGLNSVVLANNAETVLLPLNEPVHGTKRRSQIQTYLD

HHGGPGVQHIALASDDVLGTLREMRARSAMGGFEFLAPPPPNYYDGVRRRAGDVLSEEQINECQELGVLVDRDD

QGVLLQIFTKPVGDRPTFFLEMIQRIGCMEKDESGQEYQKGGCGGFGKGNESELFKSIEEYEKSLEAKQAPTVQ

GS
``` wheat A genome EPSPS amino acid sequence

SEQ ID NO: 4

```
MAMAAAATVAASASSSAVSLDRAAPAHPRRLRMPAARAAHGAVRLWGPRGAAAARATSVAAPAAPAGAEEVVLQ

PIREISGAVQLPGSKSLSNRILLLSALSEGTTVVDNLLNSEDVHYMLEALEALGLSVEADKVAKRAVVVGCGGR

FPVEKDAKEEVKLFLGNAGTAMRPLTAAVVAAGGNATYVLDGVPRMRERPIGDLVVGLQQLGADVDCFLGTNCP

PVRINGKGGLPGGKVKLSGSISSQYLSSLLMAAPLALEDVEIEIIDKLISVPYVEMTLKLMEHFGVTAEHSDSW

DRFYIKGGQKYKSPGNAYVEGDASSASYFLAGAAITGGTVTVEGCGTTSLQGDVKFAEVLEMMGAKVTWTDTSV

TVTGPPRQPFGRKHLKAVDVNMNKMPDVAMTLAVVALFADGPTAIRDVASWRVKETERMVAIRTELTKLGATVE

EGPDYCIITPPEKLNITAIDTYDDHRMAMAFSLAACAEVPVTIRDPGCTRKTFPNYFDVLSTFVKN
``` wild type spCas9

>SEQ ID NO: 5

```
MDKKYSIGLDIGTNSVGWAVITDEYKVPSKKFKVLGNTDRHSIKKNLIGALLFDSGETAEATRLKRTARRRYTR

RKNRICYLQEIFSNEMAKVDDSFFHRLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGYIDGGASQE

EFYKFIKPILEKMDGTEELLVKLNREDLLRKQRTFDNGSIPHQIHLGELHAILRRQEDFYPFLKDNREKIEKIL

TFRIPYYVGPLARGNSRFAWMTRKSEETITPWNFEEVVDKGASAQSFIERMTNFDKNLPNEKVLPKESLLYEYF

TVYNELTKVKYVTEGMRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLKRRRYTGWGRLSRKL

INGIRDKQSGKTILDFLKSDGFANRNFMQLIHDDSLTFKEDIQKAQVSGQGDSLHEHIANLAGSPAIKKGILQT
```

-continued

VKVVDELVKVMGRHKPENTVIEMARENQTTQKGQKNSRERMKRIEEGIKELGSQILKEHPVENTQLQNEKLYLY

YLQNGRDMYVDQELDINRLSDYDVDHIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSRMNTKYDENDKLIREVKVITLKSKL

VSDFRKDFQFYKVREINNYHHAHDAYLNAVVGTALIKKYPKLESEFVYGDYKVYDVRKMIAKSEQEIGKATAKY

FFYSNIMNFEKTEITLANGEIRKRPLIETNGETGEIVWDKGRDFATVRKVLSMPQVNIVKKTEVQTGGFSKESI

LPKRNSDKLIARKKDWDPKKYGGFDSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVNFLYLASHYEKLKGSPEDNEQKQLF

VEQHKHYLDEIIEQISEFSKRVILADANLDKVLSAYNKHRDKPIREQAENIIHLFTLTNLGARAAFKYFDTTID

RKRYTSTKEVLDATLIHQSITGLYETRIDLSQLGGD dCas9
>SEQ ID NO: 6

MDKKYSIGLAIGTNSVGWAVITDEYKVPSKKFKVLGNTDRHSIKKNLIGALLFDSGETAEATRLKRTARRRYTR

RKNRICYLQEIFSNEMAKVDDSFEHRLEESELVEEDKKEERHPIFGNIVDEVAYHEKYPTIYHLRKKLVDSTDK

ADLRLIYLALAHMIKFRGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGYIDGGASQE

EFYKFIKPILEKMDGTEELLVKLNREDLLRKQRTFDNGSIPHQIHLGELHAILRRQEDFYPFLKDNREKIEKIL

TFRIPYYVGPLARGNSRFAWMTRKSEETITPWNFEEVVDKGASAQSFIERMTNFDKNLPNEKVLPKESLLYEYF

TVYNELTKVKYVTEGMRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLKRRRYTGWGRLSRKL

INGIRDKQSGKTILDELKSDGFANRNFMQLIHDDSLTFKEDIQKAQVSGQGDSLHEHIANLAGSPAIKKGILQT

VKVVDELVKVMGRHKPENIVIEMARENQTTQKGQKNSRERMKRIEEGIKELGSQILKEHPVENTQLQNEKLYLY

YLQNGRDMYVDQELDINRLSDYDVDAIVPQSFLKEDSIDNKVLTRSDKNRGKSDNVPSEEVVKKMKNYWRQLLN

AKLITQRKFDNLTKAERGGLSELDKAGFIKRQLVETRQITKHVAQILDSRMNTKYDENDKLIREVKVITLKSKL

VSDERKDFQFYKVREINNYHHAHDAYLNAVVGTALIKKYPKLESEFVYGDYKVYDVRMIAICSEQEIGKATAKY

FFYSNIMNFFKTEITLANGEIRKRPLIETNGETGEIVWDKGRDFATVRKVLSMPQVNIVKKTEVQTGGFSKESI

LPKRNSDKLIARKKDWDPKKYGGFDSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVNFLYLASHYEKLKGSPEDNEQKQLF

VEQHKHYLDEIIEQISEFSKRVILADANLDKVLSAYNKHRDKPIREQAENIIHLFTLTNLGARAAFKYFDTTID

RKRYTSTKEVLDATLIHQSITGLYETRIDLSQLGGDKRPAATKKAGQAKKKK nCas9(D10A)
>SEQ ID NO: 7

MDKKYSIGLAIGTNSVGWAVITDEYKVPSKKFKVLGNTDRESIKKNLIGALLFDSGETAEATRLKRTARRRYTR

RKNRICYLQEIFSNEMAKVDDSFFHRLEESFLVEEDKKEERHPIFGNIVDEVAYHEKYPTIYHLRKKLVDSTDK

ADLRLIYLALAHMIKFRGHFLIEGDLNPDNSDVDKLFIQLVQTYNQLFEENPINASGVDAKAILSARLSKSRRL

ENLIAQLPGEKKNGLFGNLIALSLGLTPNEKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGYIDGGASQE

EFYKFIKPILEKMDGTEELLVKLNREDLLRKQRTFDNGSIPHQIHLGELHAILRRQEDFYPFLKDNREKIEKIL

TERIPYYVGPLARGNSRFAWMTRKSEETITPWNFEEVVDKGASAQSFIERMTNFDKNLPNEKVLPKESLLYEYF

TVYNELTKVKYVTEGMRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLKRRRYTGWGRLSRKL

INGIRDKQSGKTILDFLKSDGFANRNFMQLIHDDSLTEKEDIQKAQVSGQGDSLHEHIANLAGSPAIKKGILQT

VKVVDELVKVMGRHKPENIVIEMARENQTTQKGQKNSRERMKRIEEGIKELGSQILKEHPVENTQLQNEKLYLY

-continued

```
YLQNGRDMYVDQELDINRLSDYDVDHIVPQSFLKDDSIDNKVLTRSDKNRGKSDNVPSEEVVKKMKNYWRQLLN
AKLITQRKFDNLTKAERGGLSELDKAGFIKRQLVETRQITKHVAQILDSRMNTKYDENDKLIREVKVITLKSKL
VSDFRKDFQFYKVREINNYHHAHDAYLNAVVGTALIKKYPKLESEFVYGDYKVYDVRKMIAKSEQEIGKATAKY
FFYSNIMNFFKTEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIMERSSFEKNPIDFLEA
KGYKEVKKDLIIKLPKYSLFELENGRKRMLASAGELQKGNELALPSKYVNFLYLASHYEKLKGSPEDNEQKQLF
VEQHKHYLDEIIEQISEFSKRVILADANLDKVLSAYNKHRDKPIREQAENIIHLFTLTNLGAPAAFKYFDTTID
RKRYTSTKEVLDATLIHQSITGLYETRIDLSQLGGDKRPAATKKAGQAKKKK
```

XTEN
>SEQ ID NO: 8
```
KSGSETPGTSESATPE
```

UGI
>SEQ ID NO: 9
```
TNLSDIIEKETGKQLVIQESILMLPEEVEEVIGNKPESDILVHTAYDESTDENVMLLTSDAPEYKPWALVIQDS
NGENKIKML
``` fusion protein NLS-APOBEC1-XTEN-nCas9-UGI-NLS
>SEQ ID NO: 10
```
MPKKKRKVSSETGPVAVDPTLRRRIEPHEFEVFFDPRELRKETCLLYEINWGGRHSIWRHTSQNTNKHVEVNFI
EKFTTERYFCPNTRCSITWFLSWSPCGECSRAITEFLSRYPHVTLFIYIARLYHHADPRNRQGLRDLISSGVTI
QIMTEQESGYCWRNFVNYSPSNEAHWPRYPHLWVRLYVLELYCIILGLPPCLNILRRKQPQLTFFTIALQSCHY
QRLPPHILWATGLKSGSETPGTSESATPELKDKKYSIGLAIGTNSVGWAVITDEYKVPSKKFKVLGNTDRHSIK
KNLIGALLFDSGETAEATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNFDLAEDAKLQL
SKDTYDDDLDNLLAQIGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLLRKQRTFDNGSIPHQI
HLGELHAILRRQEDFYPFLKDNREKIEKILTFRIPYYVGPLARGNSRFAWMTRKSEETITPWNFEEVVDKGASA
QSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQK
AQVSGQGDSLHEHIANLAGSPAIKKGILQTVKVVDELVKVMGRHKPENIVIEMARENQTTQKGQKNSRERMKRI
EEGIKELGSQILKEHPVENTQLQNEKLYLYYLQNGRDMYVDQELDINRLSDYDVDHIVPQSFLKDDSIDNKVLT
RSDKNRGKSDNVP3EEVVKKMKYYWRQLLNAKLITQRKFDNLTKAERGGLSELDKAGFIKRQLVETRQITKHVA
QILDSRMNTKYDENDKLIREVKVITLKSKLVSDFRKDFQFYKVREINNYHHAHDAYLNAVVGTALIKKYPKLES
EFVYGDYKVYDVRKMIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELAL
PSKYVNFLYLASHYEKLKGSPEDNEQKQLFVEQHKHYLDEIIEQISEFSKRVILADANLDKVLSAYNKHRDKPI
REQAENIIHLFTLTNLGAPAAFKYFDTTIDRKRYTSTKEVLDATLIHQSITGLYETRIDLSQLGGDKRPAATKK
AGQAKKKKTRDSGGSTNLSDIIEKETGKQLVIQESILMLPEEVEEVIGNKPESDILVHTAYDESTDENVMLLTS
DAPEYKPWALVIQDSNGENKIKMLSGGSPKKKRKV
```

-continued fusion protein NLS-APOBEC1-XTEN-dCas9-UGI-NLS
>SEQ ID NO: 11

MPKKKRKVSSETGPVAVDPTLRRRIEPHEFEVFFDPRELRKETCLLYEINWGGRHSIWRHTSQNTNKHVEVNFI
EKFTTERYFCPNTRCSITWFLSWSPCGECSRAITEFLSRYPHVTLFIYIARLYHHADPRNRQGLRDLISSGVTI
QIMTEQESGYCWRNFVNYSPSNEAHWPRYPHLWVRLYVLELYCIILGLPPCLNILRRKQPQLTFFTIALQSCHY
QRLPPHILWATGLKSGSETPGTSESATPELKDKKYSIGLAIGTNSVGWAVITDEYKVPSKKFKVLGNTDRHSIK
KNLIGALLFDSGETAEATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNFDLAEDAKLQL
SKDTYDDDLDNLLAQIGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILKEMDGTEELLVKLNREDLLRKQRTEDNGSIPHQI
ELGELHAILRRQEDFYPFLKDNREKIEKILTFRIPYYVGPLARGNSRFAWMTRKSEETITPWNFEEVVDKGASA
QSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTEKEDIQK
AQVSGQGDSLHEHIANLAGSPAIKKGILQTVKVVDELVKVMGRHKPENIVIEMARENQTTQKGQKNSRERMKRI
EEGIKELGSQILKEHPVENTQLQNEKLYLYYLQNGRDMYVDQELDINRLSDYDVDAIVPQSFLKDDSIDNKVLT
RSDKNRGKSDNVPSEEVVKKMKNYWRQLLNAKLITQRKFDNLTKAERGGLSELDKAGFIKRQLVETRQITKHVA
QILDSRMNTKYDENDKLIREVKVITLKSKLVSDFRKDFQFYKVREINNYHHAHDAYLNAVVGTALIKKYPKLES
EFVYGDYKVYDVRKMIAKSEQEIGKATAKYFFYSNDINEFKTEITLANGEIRKRPLIETNGETGEIVWDKGRDF
ATVRKVLSMPQVNIVKKTEVQTGGESKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELAL
PSKYVNFLYLASHYEKLKGSPEDNEQKQLFVEQHKHYLDEIIEQISEFSKRWILADANLDKVLSAYNKHRDKPI
REQAENIIELFTLTNLGAPAAFKYFDTTIDRKRYTSTKEVLDATLIHQSITGLYETRIDLSQLGGDKRPAATKK
AGQAKKKKTRDSGGSTNLSDIIEKETGKQLVIQESILMLPEEVEEVIGNKPESDILVHTAYDESTDENVMLLTS
DAPEYKPWALVIQDSNGENKIKMLSGGSPKKKRKV nucleotide sequence of fusion protein
NLS-APOBEC1-XTEN-nCas9-UGI-NLS
>SEQ ID NO: 12

ATGccaaagaagaagaggaaggttTCATCGGAGACCGGCCCTGTTGCTGTTGACCCCACCCTGCGGCGGAGAAT
CGAGCCACACGAGTTCGAGGTGTTCTTCGACCCAAGGGAGCTCCGCAAGGAGACGTGCCTCCTGTACGAGATCA
ACTGGGGCGGCAGGCACTCCATCTGGAGGCACACCAGCCAAAACACCAACAAGCACGTGGAGGTCAACTTCATC
GAGAAGTTCACCACCGAGAGGTACTTCTGCCCAAACACCCGCTGCTCCATCACCTGGTTCCTGTCCTGGAGCCC
ATGCGGCGAGTGCTCCAGGGCCATCACCGAGTTCCTCAGCCGCTACCCACACGTCACCCTGTTCATCTACATCG
CCAGGCTCTACCACCACGCCGACCCAAGGAACAGGCAGGGCCTCCGCGACCTGATCTCCAGCGGCGTGACCATC
CAAATCATGACCGAGCAGGAGTCCGGCTACTGCTGGAGGAACTTCGTCAACTACTCCCCAAGCAACGAGGCCCA
CTGG+32AGGTACCCACACCTCTGGGTGCGCCTCTACGTGCTCGAGCTGTACTGCATCATCCTCGGCCTGCCAC
CATGCCTCAACATCCTGAGGCGCAAGCAACCACAGCTGACCTTCTTCACCATCGCCCTCCAAAGCTGCCACTAC
CAGAGGCTCCCACCACACATCCTGTGGGCTACCGGCCTCAAGTCCGGCAGCGAGACGCCAGGCACCTCCGAGAG
CGCTACGCCTGAACTTAAGGACAAGAAGTACTCGATCGGCCTCGCCATCGGGACGAACTCAGTTGGCTGGGCCG
TGATCACCGACGAGTACAAGGTGCCCTCTAAGAAGTTCAAGGTCCTGGGGAACACCGACCGCCATTCCATCAAG
AAGAACCTCATCGGCGCTCTCCTGTTCGACAGCGGGGAGACCGCTGAGGCTACGAGGCTCAAGAGAACCGCTAG
GCGCCGGTACACGAGAAGGAAGAACAGGATCTGCTACCTCCAAGAGATTTTCTCCAACGAGATGGCCAAGGTTG -continued

```
ACGATTCATTCTTCCACCGCCTGGAGGAGTCTTTCCTCGTGGAGGAGGATAAGAAGCACGAGCGGCATCCCATC

TTCGGCAACATCGTGGACGAGGTTGCCTACCACGAGAAGTACCCTACGATCTACCATCTGCGGAAGAAGCTCGT

GGACTCCACCGATAAGGCGGACCTCAGACTGATCTACCTCGCTCTGGCCCACATGATCAAGTTCCGCGGCCATT

TCCTGATCGAGGGGGATCTCAACCCAGACAACAGCGATGTTGACAAGCTGTTCATCCAACTCGTGCAGACCTAC

AACCAACTCTTCGAGGAGAACCCGATCAACGCCTCTGGCGTGGACGCGAAGGCTATCCTGTCCGCGAGGCTCTC

GAAGTCCAGGAGGCTGGAGAACCTGATCGCTCAGCTCCCAGGCGAGAAGAAGAACGGCCTGTTCGGGAACCTCA

TCGCTCTCAGCCTGGGGCTCACCCCGAACTTCAAGTCGAACTTCGATCTCGCTGAGGACGCCAAGCTGC1ACTC

TCCAAGGACACCTACGACGATGACCTCGATAACCTCCTGGCCCAGATCGGCGATCAATACGCGGACCTGTTCCT

CGCTGCCAAGAACCTGTCGGACGCCATCCTCCTGTCAGATATCCTCCGCGTGAACACCGAGATCACGAAGGCTC

CACTCTCTGCCTCCATGATCAAGCGCTACGACGAGCACCATCAGGATCTGACCCTCCTGAAGGCGCTGGTCCGC

CAACAGCTCCCGGAGAAGTACAAGGAGATTTTCTTCGATCAGTCGAAGAACGGCTACGCTGGGTACATCGACGG

CGGGGCCTCACAAGAGGAGTTCTACAAGTTCATCAAGCCAATCCTGGAGAAGATGGACGGCACGGAGGAGCTCC

TGGTGAAGCTCAACAGGGAGGACCTCCTGCGGAAGCAGAGAACCTTCGATAACGGCAGCATCCCCCACCAAATC

CATCTCGGGGAGCTGCACGCCATCCTGAGAAGGCAAGAGGACTTCTACCCTTTCCTCAAGGATAACCGGGAGAA

GATCGAGAAGATCCTGACCTTCAGAATCCCATACTACGTCGGCCCTCTCGCGCGGGGGAACTCAAGATTCGCTT

GGATGACCCGCAAGTCTGAGGAGACCATCACGCCGTGGAACTTCGAGGAGGTGGTGGACAAGGGCGCTAGCGCT

CAGTCGTTCATCGAGAGGATGACCAACTTCGACAAGAACCTGCCCAACGAGAAGGTGCTCCCTAAGCACTCGCT

CCTGTACGAGTACTTCACCGTCTACAACGAGCTCACGAAGGTGAAGTACGTCACCGAGGGCATGCGCAAGCCAG

CGTTCCTGTCCGGGGAGCAGAAGAAGGCTATCGTGGACCTCCTGTTCAAGACCAACCGGAAGGTCACGGTTAAG

CAACTCAAGGAGGACTACTTCAAGAAGATCGAGTGCTTCGATTCGGTCGAGATCAGCGGCGTTGAGGACCGCTT

CAACGCCAGCCTCGGGACCTACCACGATCTCCTGAAGATCATCAAGGATAAGGACTTCCTGGACAACGAGGAGA

ACGAGGATATCCTGGAGGACATCGTGCTGACCCTCACGCTGTTCGAGGACAGGGAGATGATCGAGGAGCGCCTG

AAGACGTACGCCCATCTCTTCGATGACAAGGTCATGAAGCAACTCAAGCGCCGGAGATACACCGGCTGGGGGAG

GCTGTCCCGCAAGCTCATCAACGGCATCCGGGACAAGCAGTCCGGGAAGACCATCCTCGACTTCCTCAAGAGCG

ATGGCTTCGCCAACAGGAACTTCATGCAACTGATCCACGATGACAGCCTCACCTTCAAGGAGGATATCCAAAAG

GCTCAAGTGAGCGGCCAGGGGACTCGCTGCACGAGCATATCGCGAACCTCGCTGGCTCCCCCGCGATCAAGAA

GGGCATCCTCCAGACCGTGAAGGTTGTGGACGAGCTCGTGAAGGTCATGGGCCGGCACAAGCCTGAGAACATCG

TCATCGAGATGGCCAGAGAGAACCAAACCACGCAGAAGGGGCAAAAGAACTCTAGGGAGCGCATGAAGCGCATC

GAGGAGGGCATCAAGGAGCTGGGGTCCCAAATCCTCAAGGAGCACCCAGTGGAGAACACCCAACTGCAGAACGA

GAAGCTCTACCTGTACTACCTCCAGAACGGCAGGGATATGTACGTGGACCAAGAGCTGGATATCAACCGCCTCA

GCGATTACGACGTCGATCATATCGTTCCCCAGTCTTTCCTGAAGGATGACTCCATCGACAACAAGGTCCTCACC

AGGTCGGACAAGAACCGCGGCAAGTCAGATAACGTTCCATCTGAGGAGGTCGTTAAGAAGATGAAGAACTACTG

GAGGCAGCTCCTGAACGCCAAGCTGATCACGCAAAGGAAGTTCGACAACCTCACCAAGGCTGAGAGAGGCGGGC

TCTCAGAGCTGGACAAGGCCGG+32CATCAAGCGGCAGCTGGTCGAGACCAGACAAATCACGAAGCACGTTGCG

CAAATCCTCGACTCTCGGATGAACACGAAGTACGATGAGAACGACAAGCTGATCAGGGAGGTTAAGGTGATCAC

CCTGAAGTCTAAGCTCGTCTCCGACTTCAGGAAGGATTTCCAGTTCTACAAGGTTCGCGAGATCAACAACTACC

ACCATGCCCATGACGCTTACCTCAACGCTGTGGTCGGCACCGCTCTGATCAAGAAGTACCCAAAGCTGGAGTCC

GAGTTCGTGTACGGGGACTACAAGGTTTACGATGTGCGCAAGATGATCGCCAAGTCGGAGCAAGAGATCGGCAA

GGCTACCGCCAAGTACTTCTTCTACTCAAACATCATGAACTTCTTCAAGACCGAGATCACGCTGGCCAACGGCG

AGATCCGGAAGAGACCGCTCATCGAGACCAACGGCGAGACGGGGGAGATCGTGTGGGACAAGGGCAGGGAT7TC
```

-continued

```
GCGACCGTCCGCAAGGTTCTCTCCATGCCCCAGGTGAACATCGTCAAGAAGACCGAGGTCCAAACGGGCGGGTT
CTCAAAGGAGTCTATCCTGCCTAAGCGGAACAGCGACAAGCTCATCGCCAGAAAGAAGGACTGGGACCCAAAGA
AGTACGGCGGGTTCGACAGCCCTACCGTGGCCTACTCGGTCCTGGTTGTGGCGAAGGTTGAGAAGGGCAAGTCC
AAGAAGCTCAAGAGCGTGAAGGAGCTCCTGGGGATCACCATCATGGAGAGGTCCAGCTTCGAGAAGAACCCAAT
CGACTTCCTGGAGGCCAAGGGCTACAAGGAGGTGAAGAAGGACCTGATCATCAAGCTCCCGAAGTACTCTCTCT
TCGAGCTGGAGAACGGCAGGAAGAGAATGCTGGCTTCCGCTGGCGAGCTCCAGAAGGGGAACGAGCTCGCGCTG
CCAAGCAAGTACGTGAACTTCCTCTACCTGGCTTCCCACTACGAGAAGCTCAAGGGCAGCCCGGAGGACAACGA
GCAAAAGCAGCTGTTCGTCGAGCAGCACAAGCATTACCTCGACGAGATCATCGAGCAAATCTCCGAGTTCAGCA
AGCGCGTGATCCTCGCCGACGCGAACCTGGATAAGGTCCTCTCCGCCTACAACAAGCACGGGACAAGCCCATC
AGAGAGCAAGCGGAGAACATCATCCATCTCTTCACCCTGACGAACCTCGGCGCTCCTGCTGC+32CAAGTACTT
CGACACCACGATCGATCGGAAGAGATACACCTCCACGAAGGAGGTCCTGGACGCGACCCTCATCCACCAGTCGA
TCACCGGCCTGTACGACGAGGATCGACCTCTCACAACTCGGCGGGGATAAGAGACCCGCAGCAACCAAGAAG
GCAGGGCAAGCAAAGAAGAAGAAGACGCGTGACTCCGGCGGCAGCACCAACCTGTCCGACATCATCGAGAAGGA
GACGGGCAAGCAACTCGTGATCCAGGAGAGCATCCTCATGCTGCCAGAGGAGGTGGAGGAGGTCATCGGCAACA
AGCCAGAGTCCGACATCCTGGTGCACACCGCCTACGACGAGTCCACCGACGAGAACGTCATGCTCCTGACCAGC
GACGCCCCAGAGTACAAGCCATGGGCCCTCGTCATCCAGGACAGCAACGGGGAGAACAAGATCAAGATGCTGtc
gggggggagcccaaagaagaagcggaaggtgTAG
``` nucleotide sequence of fusion protein
NLS-APOBEC1-XTEN-dCas9-UGI-NLS

>SEQ ID NO: 13

```
ATGccaaagaagaagaggaaggttTCATCGGAGACCGGCCCTGTTGCTGTTGACCCCACCCTGCGGCGGAGAAT
CGAGCCACACGAGTTCGAGGTGTTCTTCGACCCAAGGGAGCTCCGCAAGGAGACGTGCCTCCTGTACGAGATCA
ACTGGGGCGGCAGGCACTCCATCTGGAGGCACACCAGCCAAAACACCAACAAGCACGTGGAGGTCAACTTCATC
GAGAAGTTCACCACCGAGAGGTACTTCTGCCCAAACACCCGCTGCTCCATCACCTGGTTCCTGTCCTGGAGCCC
ATGCGGCGAGTGCTCCAGGGCCATCACCGAGTTCCTCAGCCGCTACCCACACGTCACCCTGTTCATCTACATCG
CCAGGCTCTACCACCACGCCGACCCAAGGAACAGGCAGGGCCTCCGCGACCTGATCTCCAGCGGCGTGACCATC
CAAATCATGACCGAGCAGGAGTCCGGCTACTGCTGGAGGAACTTCGTCAACTACTCCCCAAGCAACGAGGCCCA
CTGGCCAAGGTACCCACACCTCTGGGTGCGCCTCTACGTGCTCGAGCTGTACTGCATCATCCTCGGCCTGCCAC
CATGCCTCAACATCCTGAGGCGCAAGCAACCACAGCTGACCTTCTTCACCATCGCCCTCCAAAGCTGCCACTAC
CAGAGGCTCCCACCACACATCCTGTGGGCTACCGGCCTCAAGTCCGGCAGCGAGACGCCAGGCACCTCCGAGAG
CGCTACGCCTGAACTTAAGGACAAGAAGTACTCGATCGGCCTCGCCATCGGGACGAACTCAGTTGGCTGGGCCG
TGATCACCGACGAGTACAAGGTGCCCTCTAAGAAGTTCAAGGTCCTGGGGAACACCGACCGCCATTCCATCAAG
AAGAACCTCATCGGCGCTCTCCTGTTCGACAGCGGGGAGACCGCTGAGGCTACGAGGCTCAAGAGAACCGCTAG
GCGCCGGTACACGAGAAGGAAGAACAGGATCTGCTACCTCCAAGAGATTTTCTCCAACGAGATGGCCAAGGTTG
ACGATTCATTCTTCCACCGCCTGGAGGAGTCTTTCCTCGTGGAGGAGGATAAGAAGCACGAGCGGCATCCCATC
TTCGGCAACATCGTGGACGAGGTTGCCTACCACGAGAAGTACCCTACGATCTACCATCTGCGGAAGAAGCTCGT
GGACTCCACCGATAAGGCGGACCTCAGACTGATCTACCTCGCTCTGGCCCACATGATCAAGTTCCGCGGCCATT
TCCTGATCGAGGGGGATCTCAACCCAGACAACAGCGATGTTGACAAGCTGTTCATCCAACTCGTGCAGACCTAC
AACCAACTCTTCGAGGAGAACCCCGATCAACGCCTCTGGCGTGGACGCGAAGGCTATCCTGTCCGCGAGGCTCTC
GAAGTCCAGGAGGCTGGAGAACCTGATCGCTCAGCTCCCAGGCGAGAAGAAGAACGGCCTGTTCGGGAACCTCA
TCGCTCTCAGCCTGGGGCTCACCCCGAACTTCAAGTCGAACTTCGATCTCGCTGAGGACGCCAAGCTGCAACTC
TCCAAGGACACCTACGACGATGACCTCGATAACCTCCTGGCCCAGATCGGCGATCAATACGCGGACCTGTTCCT
```

-continued

```
CGCTGCCAAGAACCTGTCGGACGCCATCCTCCTGTCAGATATCCTCCGCGTGAACACCGAGATCACGAAGGCTC

CACTCTCTGCCTCCATGATCAAGCGCTACGACGAGCACCATCAGGATCTGACCCTCCTGAAGGCGCTGGTCCGC

CAACAGCTCCCGGAGAAGTACAAGGAGATTTTCTTCGATCAGTCGAAGAACGGCTACGCTGGGTACATCGACGG

CGGGGCCTCACAAGAGGAGTTCTACAAGTTCATCAAGCCAATCCTGGAGAAGATGGACGGCACGGAGGAGCTCC

TGGTGAAGCTCAACAGGGAGGACCTCCTGCGGAAGCAGAGAACCTTCGATAACGGCAGCATCCCCCACCAAATC

CATCTCGGGGAGCTGCACGCCATCCTGAGAAGGCAAGAGGACTTCTACCCTTTCCTCAAGGATAACCGGGAGAA

GATCGAGAAGATCCTGACCTTCAGAATCCCATACTACGTCGGCCCTCTCGCGCGGGGGAACTCAAGATTCGCTT

GGATGACCCGCAAGTCTGAGGAGACCATCACGCCGTGGAACTTCGAGGAGGTGGTGGACAAGGGCGCTAGCGCT

CAGTCGTTCATCGAGAGGATGACCAACTTCGACAAGAACCTGCCCAACGAGAAGGTGCTCCCTAAGCACTCGCT

CCTGTACGAGTACTTCACCGTCTACAACGAGCTCACGAAGGTGAAGTACGTCACCGAGGGCMTGCGCAAGCCAG

CGTTCCTGTCCGGGGAGCAGAAGAAGGCTATCGTGGACCTCCTGTTCAAGACCAACCGGAAGGTCACGGTTAAG

CAACTCAAGGAGGACTACTTCAAGAAGATCGAGTGCTTCGATTCGGTCGAGATCAGCGGCGTTGAGGACCGCTT

CAACGCCAGCCTCGGGACCTACCACGATCTCCTGAAGATCATCAAGGATAAGGACTTCCTGGACAACGAGGAGA

ACGAGGATATCCTGGAGGACATCGTGCTGACCCTCACGCTGTTCGAGGACAGGGAGATGATCGAGGAGCGCCTG

AAGACGTACGCCCATCTCTTCGATGACAAGGTCATGAAGCAACTCAAGCGCCGGAGATACACCGGCTGGGGGAG

GCTGTCCCGCAAGCTCATCAACGGCATCCGGGACAAGCAGTCCGGGAAGACCATCCTCGACTTCCTCAAGAGCG

ATGGCTTCGCCAACAGGAACTTCATGCAACTGATCCACGATGACAGCCTCACCTTCAAGGAGGATATCCAAAAG

GCTCAAGTGAGCGGCCAGGGGGACTCGCTGCACGAGCATATCGCGAACCTCGCTGGCTCCCCCGCGATCAAGAA

GGGCATCCTCCAGACCGTGAAGGTTGTGGACGAGCTCGTGAAGGTCATGGGCCGGCACAAGCCTGAGAACATCG

TCATCGAGATGGCCAGAGAGAACCAAACCACGCAGAAGGGGCAAAAGAACTCTAGGGAGCGCATGAAGCGCATC

GAGGAGGGCATCAAGGAGCTGGGGTCCCAAATCCTCAAGGAGCACCCAGTGGAGAACACCCAACTGCAGAACGA

GAAGCTCTACCTGTACTACCTCCAGAACGGCAGGGATATGTACGTGGACCAAGAGCTGGATATCAACCGCCTCA

GCGATTACGACGTCGATGCTATCGTTCCCCAGTCTTTCCTGAAGGATGACTCCATCGACAACAAGGTCCTCACC

AGGTCGGACAAGAACCGCGGCAAGTCAGATAACGTTCCATCTGAGGAGGTCGTTAAGAAGATGAAGAACTACTG

GAGGCAGCTCCTGAACGCCAAGCTGATCACGCAAAGGAAGTTCGACAACCTCACCAAGGCTGAGAGAGGCGGGC

TCTCAGAGCTGGACAAGGCCGGCTTCATCAAGCGGCAGCTGGTCGAGACCAGACAAATCACGAAGCACGTTGCG

CAAATCCTCGACTCTCGGATGAACACGAAGTACGATGAGAACGACAAGCTGATCAGGGAGGTTAAGGTGATCAC

CCTGAAGTCTAAGCTCGTCTCCGACTTCAGGAAGGATTTCCAGTTCTACAAGGTTCGCGAGATCAACAACTACC

ACCATGCCCATGACGCTTACCTCAACGCTGTGGTCGGCACCGCTCTGATCAAGAAGTACCCAAAGCTGGAGTCC

GAGTTCGTGTACGGGGACTACAAGGTTTACGATGTGCGCAAGATGATCGCCAAGTCGGAGCAAGAGATCGGCAA

GGCTACCGCCAAGTACTTCTTCTACTCAAACATCATGAACTTCTTCAAGACCGAGATCACGCTGGCCAACGGCG

AGATCCGGAAGAGACCGCTCATCGAGACCAACGGCGAGACGGGGGAGATCGTGTGGGACAAGGGCAGGGATTTC

GCGACCGTCCGCAAGGTTCTCTCCATGCCCCAGGTGAACATCGTCAAGAAGACCGAGGTCCAAACGGGCGGGTT

CTCAAAGGAGTCTATCCTGCCTAAGCGGAACAGCGACAAGCTCATCGCCAGAAAGAAGGACTGGGACCCAAAGA

AGTACGGCGGGTTCGACAGCCCTACCGTGGCCTACTCGGTCCTGGTTGTGGCGAAGGTTGAGAAGGGCAAGTCC

AAGAAGCTCAAGAGCGTGAAGGAGCTCCTGGGGATCACCATCATGGAGAGGTCCAGCTTCGAGAAGAACCCAAT

CGACTTCCTGGAGGCCAAGGGCTACAAGGAGGTGAAGAAGGACCTGATCATCAAGCTCCCGAAGTACTCTCTCT

TCGAGCTGGAGAACGGCAGGAAGAGAATGCTGGCTTCCGCTGGCGAGCTCCAGAAGGGGAACGAGCTCGCGCTG

CCAAGCAAGTACGTGAACTTCCTCTACCTGGCTTCCCACTACGAGAAGCTCAAGGGCAGCCCGGAGGACAACGA

GCAAAAGCAGCTGTTCGTCGAGCAGCACAAGCATTACCTCGACGAGATCATCGAGCAAATCTCCGAGTTCAGCA

AGCGCGTGATCCTCGCCGACGCGAACCTGGATAAGGTCCTCTCCGCCTACAACAAGCACCGGGACAAGCCCATC
```

-continued

```
AGAGAGCAAGCGGAGAACATCATCCATCTCTTCACCCTGACGAACCTCGGCGCTCCTGCTGCTTTCAAGTACTT
CGACACCACGATCGATCGGAAGAGATACACCTCCACGAAGGAGGTCCTGGACGCGACCCTCATCCACCAGTCGA
TCACCGGCCTGTACGAGACGAGGATCGACCTCTCACAACTCGGCGGGGATAAGAGACCCGCAGCAACCAAGAAG
GCAGGGCAAGCAAAGAAGAAGAAGACGCGTGACTCCGGCGGCAGCACCAACCTGTCCGACATCATCGAGAAGGA
GACGGGCAAGCAACTCGTGATCCAGGAGAGCATCCTCATGCTGCCAGAGGAGGTGGAGGAGGTCATCGGCAACA
AGCCAGAGTCCGACATCCTGGTGCACACCGCCTACGACGAGTCCACCGACGAGAACGTCATGCTCCTGACCAGC
GACGCCCCAGAGTACAAGCCATGGGCCCTCGTCATCCAGGACAGCAACGGGGAGAACAAGATCAAGATGCTGtc
gggggggagcccaaagaagaagcggaaggtgTAG
``` rice ACCase amino acid sequence

SEQ ID NO: 14

```
MTSTHVATLGVGAQAPPRHQKKSAGTAFVSSGSSRPSYRKNGQRTRSLREESNGGVSDSKKLNHSIRQGLAGII
DLPNDAASEVDISHGSEDPRGPTVPGSYQMNGIINETHNGRHASVSKVVEFCTALGGKTPIHSVLVANNGMAAA
KFMRSVRTWANDTFGSEKAIQLIAMATPEDLRINAEHIRIADQFVEVPGGTNNNNYANVQLIVEIAERTGVSAV
WPGWGHASENPELPDALTAKGIVFLGPPASSMHALGDKVGSALIAQAAGVPTLAWSGSHVEVPLECCLDSIPDE
MYRKACVTTTEEAVASCQVVGYPAMIKASWGGGGKGIRKVHNDDEVRTLFKQVQGEVPGSPIFIMRLAAQSRHL
EVQLLCDQYGNVAALHSRDCSVQRRHQKIIEEGPVTVAPRETVKELEQAARRLAKAVGYVGAATVEYLYSMETG
EYYFLELNPRLQVEHPVTEWIAEVNLPAAQVAVGMGIPLWQIPEIRRFYGMNHGGGYDLWRKTAALATPFNFDE
VDSKWPKGPKVAVRITSEDPDDGFKPTGGKVKEISFKSKPNVWAYFSVKSGGGIHEFADSQFGHVFAYGTTRSA
AITTMALALKEVQIRGEIHSNVDYTVDLLNASDFRENKIHTGWLDTRIAMRVQAERPPWYISVVGGALYKTVTA
NTATVSDYVGYLTKGQIPPKHISLVYTTVALNIDGKKYTIDTVRSGHGSYRLRMNGSTVDANVQILCDGGLLMQ
LDGNSHVIYAEEEASGTRLLIDGKTCMLQNDHDPSKLLAETPCKLLRFLVADGAHVDADVPYAEVEVMKMCMPL
LSPASGVIHVVMSEGQAMQAGDLIARLDLDDPSAVKRAEPFEDTFPQMGLPIAASGQVHKLCAASLNACRMILA
GYEHDIDKVVPELVYCLDTPELPFLQWEELMSVLATRLPRNLKSELEGKYEEYKVKFDSGIINDEPANMLRVII
EENLACGSEKEKATNERLVEPLMSLLKSYEGGRESHAUFVVKSLFEEYLYVEELFSDGIQSDVIERLRLQHSKD
LQKVVDIVLSHQSVRNKTKLILKLMESLVYPNPAAYRDQLIRF3SLNHKAYYKLALKASELLEQTKLSELRARI
ARSLSELEMFTEESKGLSMHKRETATKESMEDLVTAPLPVEDALISLEDCSDTTVQQRVIETYIARLYQPHLVK
DSIKMKWIESGVIALWEFPEGHFDARNGGAVLGDKRWGAMVIVKSLESLSMAIRFALKETSHYTSSEGNMMHIA
LLGADNKIMHIIQESGDDADRIAKLPLILKDNVTDLHASGVKTISFIVQRDEARMTMRRTELMSDEKLSYEEPI
LRHVEPPLSALLELDKLKVKGYNEMKYTPSRDRQWHIYTLRNTENPKMLHRVFFRTLVRQPSVSNKFSSGQIGD
MEVGSAEEPLSFTSTSILRSLMTAIEELELHAIRTGHSHMYLHVLKEQKLLDLVPVSGNTVLDVGQDEATAYSL
LKEMAMKIHELVGARMHHLSVCQWEVKLKLDCDGPASGTWRIVTTNVTSHTCTVDIYREMEDKESRKLVYHPAT
PAAGPLHGVALNNPYQPLSVIDLKRCSARNNRTTYCYDFPLAFETAVRKSWSSSTSGASKGVENAQCYVKATEL
VFADKHGSWGTPLVQMDRPAGLNDIGMVAWTLKMSTPEFPSGREIIVVANDITFRAGSFGPREDAFFEAVTNLA
CEKKLPLIYLAANSGARIGIADEVKSCFRVGWSDDGSPERGFQYIYLSEEDYARIGTSVIAHKMQLDSGEIRWV
IDSVVGKEDGLGVENIHGSAAIASAYSRAYKETFTLTFVTGRTVGIGAYLARLGIRCIQRLDQPIILTGYSALM
KLLGREVYSSHMQLGGPKIMATNGVVHLTVSDDLEGVSNILRWLSYVPAYIGGPLPVTTPLDPPDRPVAYIPEN
SCDPRAAIRGVDDSQGKWLGGMFDKDSFVETFEGWAKTVVTGRAKLGGIPVGVIAVETQTMMQTIPADPGQLDS
REQSVPRAGQVWFPDSATKTAQALLDENREGLPLFILANWRGFSGGQRDLFEGILQAGSTIVENLRTYNQPAFV
YIPMAAELRGGAWVVVDSKINPDRIECYAERTAKGNVLEPQGLIEIKERSEELQDCMSRLDPTLIDLYAKLEVA
NKNGSADTKSLQENIEARTKQLMPLYTQIAIRFAELHDTSLRMAAKGVIKKVVDWEESRSFFYKRLRRRISEDV
LAKEIPAVAGEQFSHQPAIELIKKWYSASHAAEWDDDDAFVAWMDNPENYKDYIQYLKAQRVSQSLSSLSDSSS
```

-continued

DLQALPQGLSMLLDKMDPSRRAQLVEEIRKVLG wheat ACCase amino acid sequence
SEQ ID NO: 15
MGSTHLPIVGFNASTTPSLSTIRPVNSAGAAFQPSAPSRTSKKKSRRVQSLRDGGDGGVSDPNQSIRQGLAGII

DLPKEGTSAPEVDISHGSEEPRGSYQMNGILNEAHNGRHASLSKVVEFCVALGGKTPIHSVLVANNGMAAAKFM

RSVRTWANETFGSEKAIQLIAMATPEDMRINAEHIRIADQFVEVPGGTNNNNYANVQLIVEIAVRTGVSAVWPG

WGHASENPELPDALNANGIVFLGPPSSSMNALGDKVGSALIAQAAGVPTLPWSGSQVEIPLEVCLDSIPAEMYR

KACVSTTEEALASCQMIGYPAMIKASWGGGGKGIRKVNNDDDVRALFRQVQGEVPGSPIFIMRLASQSRHLEVQ

LLCDQYGNVAALHSRDCSVQRRHQKIIEEGPVTVAPRETVKELEQAARRLAKAVGYVGAATVEYLYSMETGEYY

FLELNPRLQVEHPVTEWIAEVNLPAAQVAVGMGIPLWQVPEIRRFYGMDNGGGYDIWRKTAALATPFNFDEVDS

QWPKGHCVAVRITSEDPDDGFKPTGGKVKEISFKSKPNVWAYFSVKSGGGIHEFADSQFGHVFAYGVSRAAAIT

NMSLALKEIQIRGEIHSNVDYTVDLLNASDFKENRIHTGWLDNRIAMRVQAERPPWYISVVGGALYKTITSNTD

TVSEYVSYLVKGQIPPKHISLVHSTVSLNIEESKYTIETIRSGQGSYRLRMNGSVIEANVQTLCDGGLLMQLDG

NSHVIYAEEEAGGTRLLIDGKTCLLQNDHDPSRLLAETPCKLLRFLVADGAHVEADVPYAEVEVMKMCMPLLSP

AAGVINVLLSEGQPMQAGDLIARLDLDDPSAVKRAEPFNGSFPEMSLPIAASGQVHKRCATSLNAARMVLAGYD

HPINKVVQDLVSCLDAPELPFLQWEELMSVLATRLPRLLKSELEGKYSEYKLNVGHGKSKDFPSKMLREIIEEN

LAHGSEKEIATNERLVEPLMSLLKSYEGGRESHAHFIVKSLFEDYLSVEELFSDGIQSDVIERLRQQHSKDLQK

VVDIVLSHQGVRNKTKLILTLMEKLVYPNPAAYKDQLTRFSSLNHKRYYKLALKASELLEQTKLSELRTSIARS

LSELEMFTEERTAISEIMGDLVTAPLPVEDALVSLFDCSDQTLQQRVIETYISRLYQPHLVKDSIQLKYQESGV

IALWEFAEAHSEKRLGAMVIVKSLESVSAAIGAALKDTSRYASSEGNIMHIALLGADNQMHGTEDSGDNDQAQV

RIDKLSATLEQNTVTADLRAAGVKVISCIVQRDGALMPMRHTFLLSDEKLCYEEEPVLRHVEPPLSALLELGKL

KVKGYNEVKYTPSRDRQWNIYTLRNTENPKMLHRVFFRTLVRQPGASNKFTSGHISDVEVGGAEESLSFTSSSI

LRSLMTAIEELELHAIRTGHSHMFLCILKEQKLLDLVPVSGNTVVDIGQDEATACSLLKEMALQIHELVGARMH

HLSVCQWEVKLKLDSDGPASGTWRVVTTNVTSHTCTYDIYREVEDTESQKLVYHSAPSSSGPLHGVALNTPYQP

LSVIDLKRCSARNNRTTYCYDFPLAFETAVQKSWSNISSDNNRCYVKATELVFAHKNGSWGTPVIPMERPAGLN

DIGMVAWILDMSTPEYPNGRQIVVIANDITFRAGSFGPREDAFFETVTNLACERKLPLIYLAANSGARIGIADE

VKSCFRVGWSDDGSPERGFQYIYLTEEDHARISTSVIAHKMQLDNGEIRWVIDSVVGKEDGLGVENIHGSAAIA

SAYSRAYEETFTFLTFVTGRTVGIGAYLARLGIRCIQRTDQPIILTGFSALNKLLGREVYSSHMQLGGPKIMAT

NGVVHLTVSDDLEGVSNILRWLSYVPANIGGPLPITKSLDPPDRPVAYIPENTCDPRAAISGIDDSQGKWLGGM

FDKDSFVETFEGWAKSWTGRAKLGGIPVGVIAVETQTMMQLIPADPGQLDSHERSVPRAGQVWFPDSATKTAQA

MLDFNREGLPLFILANWRGFSGGQRDLFEGILQAGSTIVENLRTYNQPAFVYIPKAAELRGGAWWIDSKINPDR

IEFYAERTAKGNVLEPQGLIEIKFRSEELQECMGRLDPELINLKAKLQGVKHENGSLPESESLQKSIEARKKQL

LPLYTQIAVRFAELHDTSLRMAAKGVIKKVVDWEDSRSFFYKRLRRRISEDVLAKEIRGVSGKQFSHQSAIELI

QKWYLASKGAETGSTEWDDDDAFVAWRENPENYQEYIKELRAQRVSQLLSDVADSSPDLEALPQGLSMLLEKMD

PSRRAQFVEEVKKVLK rice ALS amino acid sequence
SEQ ID NO: 16
MATTAAAAATLSAAATAKTGRKNHQRHHVLPARGRVGAAAVRCSAVSPVTPPSPAPPATPLRPWGPAEPRKGA

DILVEALERCGVSDVEAYPGGASMEIHQALTRSPVITNHLFRHEQGEAFAASGYARASGRVGVCVATSGPGATN

LVSALADALLDSVPMVAITGQVPRRMIGTDAFQETPIVEVTRSITKHNYLVLDVEDIPRVIQEAFFLASSGRPG

PVLVDIPKDIQQQMAVPVWDTSMNLPGYIARLPKPPATELLEQVLRLVGESRRPILYVGGGCSASGDELRRFVE

LTGIPVTTTLMGLGNFPSDDPLSLRMLGMEGTVYANYAVDKADLLLAFGVEFDDRVTGKIEAFASRAKIVHIDI

DPAEIGKNKQPHVSICADVKLALQGLNALLDQSTTKTSSDFSAWHNELDQQKREFPLGYKTFGEEIPPQYAIQV

-continued

LDELTKGEAIIATGVGQHQMWAAQYYTYKRPRQWLSSAGLGAMGFGLPAAAGASVANPGVTVVDIDGDGSFLMN

IQELALIRIENLPVKVMVLNNQHLGMVVQWEDRFYKANRAHTYLGNPECESEIYPDFVTIAKGFNIPAVRVTKK

SEVRAAIKKMLETPGPYLLDIIVPHQEHVLPMIPSEGAFKDMILDGDGRTMY wheat ALS amino acid sequence (partial)

SEQ ID NO: 17

AASPAATSAAPPATALRPWGPSEPRKGADILVEALERCGIVDVFAYPGGASMEIHQALTRSPVITNHLFREEQG

EAFAASGYARASGRVGVCVATSGPGATNLVSALADALLDSIPMVAITGQVPRRMIGTDAFQETPIVEVTRSITK

HNYLVLDVEDIPRVIQEAFFLASSGRPGPVLVDIPKDIQQQMAVPVWDTPMSLPGYIARLPKPPSTESLEQVLR

LVGESRRPILYVGGGCAASGEELRRFVELTGIPVTTTLMGLGNFPSDDPLSRMLGMHGTVYANYAVDKADLLL

AFGVRFDDRVTGKIEAFASRSKIVHIDIDPAEIGKNKQPHVSICADVKLALQGLNDLLNGSKAQQGLDFGPWHK

ELDQQKREFPLGEKTFGEAIPPQYAIQVLDELTKGEAIIATGVGQHQMWAAQYYTYKRPRQWLSSSGLGAMGFG

LPAAAGAAVANPGVTVVDIDGDGSFLMNIQELALIRIENLPVKVMILNNQHLGMVVQWEDREYKANRAHTYLGN

PENESEIYPDFVTIAKGENVPAVRVTKKSEVTAAIKKMLETPGPYLLDIIVPHQEHVLPMIPSGGAFKDMIMEG

DGRTSY wheat HPPD amino acid sequence

SEQ ID NO: 18

MPPTPTTPAATGAGAAAAVITEHARPRRMVRFNPRSDRFHTLSFHHVEFWCADAASAAGRFAFALGAPLAARSD

LSTGNSVHASQLLRSGNLAFLFTAPYANGCDAATASLPSFSADAARRFSADHGLAVRSIALRVADAAEAFRASV

DGGARPAFSPVDLGRGFGFAEVELYGDVVLRFVSHPDDTDVPFLPGFEGVSNPDAVDYGLTREDEVVGNVPELA

PAAAYVAGFAGFHEFAEFTTEDVGTAESGLNSMVLANNSEGVLLPLNEPVHGTKRRSQIQTFLEHHGGSGVQHI

AVASSDVLRTLREMRARSAMGGFDFLPPRCRKYYEGVRRIAGDVLSEAQIKECQELGVLVDRDDQGVLLQIFTK

PVGDRPTLFLEMIQRIGCMEKDERGEEYQKGGCGGFGKGNESELFKSIEDYEKSLEAKQSAAVQGS

The invention claimed is:

1. A nucleotide sequence encoding an ACCase mutant, the nucleotide sequence comprising at least one nucleotide substitution resulting in at least one amino acid mutation selected from the group consisting of S1768F, Q1828*, P1829F, and A2025T, and combinations thereof,
    wherein the amino acid position refers to SEQ ID NO: 1,
    wherein said ACCase mutant confers herbicide resistance to a plant.

2. The nucleotide sequence of claim 1, wherein the plant is a rice plant.

3. The nucleotide sequence of claim 1, wherein the herbicide is an aryloxyphenoxypropionic acid herbicide.

4. The nucleotide sequence of claim 3, wherein the aryloxyphenoxypropionic acid herbicide is haloxyfop.

5. A method of conferring herbicide resistance on a plant, comprising:
    introducing into the plant a nucleotide sequence according to claim 1.

6. The method of claim 5, wherein the plant is a rice plant.

7. The method of claim 5, wherein the herbicide is an aryloxyphenoxypropionic acid herbicide.

8. The method of claim 7, wherein the aryloxyphenoxy-propionic acid herbicide is haloxyfop.

9. A nucleotide sequence encoding an ALS mutant, the nucleotide sequence comprising at least one nucleotide substitution resulting in an amino acid mutation at one or more positions selected from 655, 659, and combinations thereof, wherein the amino acid position refers to SEQ ID NO: 2,
  wherein said mutant confers herbicide resistance to a plant, and wherein the amino acid mutation at position 655 is selected from the group consisting of G655D, G655S, and G655N.

10. The nucleotide sequence of claim 9, wherein the amino acid mutation is G655S.

11. The nucleotide sequence of claim 9, wherein the plant is a rice plant or a wheat plant.

12. The nucleotide sequence of claim 9, wherein the herbicide is an imidazoline herbicide.

13. A method of conferring herbicide resistance on a plant, comprising:

introducing into the plant a nucleotide sequence according to claim 9.

14. The method of claim 13, wherein the amino acid mutation is G655S.

15. The method of claim 13, wherein the plant is a rice plant or a wheat plant.

16. The method of claim 13, wherein the herbicide is an imidazoline herbicide.

* * * * *